(12) United States Patent
Mizuki et al.

(10) Patent No.: US 9,306,171 B2
(45) Date of Patent: Apr. 5, 2016

(54) MATERIAL FOR ORGANIC ELECTROLUMINESCENCE DEVICE AND ORGANIC ELECTROLUMINESCENCE DEVICE

(71) Applicants: Yumiko Mizuki, Chiba (JP); Mitsunori Ito, Chiba (JP); Tetsuya Inoue, Chiba (JP); Kumiko Hibino, Chiba (JP); Kazuki Nishimura, Chiba (JP); Kei Yoshida, Chiba (JP)

(72) Inventors: Yumiko Mizuki, Chiba (JP); Mitsunori Ito, Chiba (JP); Tetsuya Inoue, Chiba (JP); Kumiko Hibino, Chiba (JP); Kazuki Nishimura, Chiba (JP); Kei Yoshida, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 404 days.

(21) Appl. No.: 13/705,742

(22) Filed: Dec. 5, 2012

(65) Prior Publication Data

US 2014/0001446 A1  Jan. 2, 2014

Related U.S. Application Data

(60) Provisional application No. 61/582,694, filed on Jan. 3, 2012.

(30) Foreign Application Priority Data

Dec. 5, 2011 (JP) .................................. 2011-266238
Mar. 30, 2012 (JP) .................................. 2012-083146

(51) Int. Cl.
*C07D 209/86* (2006.01)
*H01L 51/00* (2006.01)
(Continued)

(52) U.S. Cl.
CPC .......... *H01L 51/0052* (2013.01); *C07D 209/86* (2013.01); *C09K 11/06* (2013.01); *H01L 51/0071* (2013.01); *H01L 51/0072* (2013.01); *H01L 51/5072* (2013.01);
(Continued)

(58) Field of Classification Search
None
See application file for complete search history.

(56) References Cited

U.S. PATENT DOCUMENTS 6,458,475 B1   10/2002   Adachi et al.
6,902,830 B2   6/2005    Thompson et al.
(Continued)

FOREIGN PATENT DOCUMENTS

CN   102372694   3/2012
CN   102516230   6/2012
(Continued)

OTHER PUBLICATIONS

Machine generated English language translation of JP-2009-120582, translation generated Mar. 2015, 103 pages.*

(Continued)

*Primary Examiner* — Robert S Loewe
(74) *Attorney, Agent, or Firm* — Oblon, McClelland, Maier & Neustadt, L.L.P.

(57) ABSTRACT

A material for organic electroluminescence device having a specific central skeleton to which a cyano-substituted aromatic hydrocarbon group or a cyano-substituted heterocyclic group is bonded at its specific position is described. Further described is an organic electroluminescence device including an organic thin film layer between an anode and a cathode. The organic thin film layer include an light emitting layer and at least one layer of the organic thin film layer contains the material for organic electroluminescence device. The material for organic electroluminescence device realizes an organic electroluminescence device with good emission efficiency.

25 Claims, 4 Drawing Sheets

(51) Int. Cl.
*C09K 11/06* (2006.01)
*H01L 51/50* (2006.01)
*H05B 33/10* (2006.01)

(52) U.S. Cl.
CPC ....... *H05B 33/10* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01)

(56) References Cited

U.S. PATENT DOCUMENTS

| | | | |
|---|---|---|---|
| 7,227,027 B2 * | 6/2007 | Qiu et al. | 548/440 |
| 7,291,406 B2 | 11/2007 | Thompson et al. | |
| 7,695,828 B2 | 4/2010 | Seo et al. | |
| 8,003,230 B2 | 8/2011 | Seo et al. | |
| 8,420,227 B2 | 4/2013 | Iwaki et al. | |
| 8,557,399 B2 | 10/2013 | D'Andrade et al. | |
| 8,748,013 B2 | 6/2014 | Seo et al. | |
| 2002/0034656 A1 | 3/2002 | Thompson et al. | |
| 2002/0107405 A1 * | 8/2002 | Lin et al. | 548/439 |
| 2004/0086745 A1 * | 5/2004 | Iwakuma et al. | 428/690 |
| 2007/0231503 A1 * | 10/2007 | Hwang et al. | 428/1.1 |
| 2008/0169755 A1 * | 7/2008 | Kim et al. | 313/504 |
| 2008/0174237 A1 | 7/2008 | Kim et al. | |
| 2008/0254318 A1 * | 10/2008 | Nakashima et al. | 428/690 |
| 2009/0072727 A1 | 3/2009 | Takeda | |
| 2010/0230660 A1 * | 9/2010 | Yokoyama et al. | 257/40 |
| 2011/0278555 A1 * | 11/2011 | Inoue et al. | 257/40 |
| 2012/0126205 A1 | 5/2012 | Kawamura et al. | |
| 2012/0126208 A1 | 5/2012 | Kawamura et al. | |
| 2012/0175599 A1 * | 7/2012 | Yokoyama et al. | 257/40 |
| 2012/0205642 A1 | 8/2012 | Yokoyama et al. | |
| 2012/0211736 A1 * | 8/2012 | Kim et al. | 257/40 |
| 2012/0223295 A1 | 9/2012 | Inoue et al. | |
| 2012/0273767 A1 | 11/2012 | Yokoyama et al. | |
| 2012/0305900 A1 | 12/2012 | Kim et al. | |
| 2013/0009139 A1 | 1/2013 | Ohsawa et al. | |
| 2013/0020558 A1 | 1/2013 | Ogiwara | |
| 2013/0056720 A1 | 3/2013 | Kim et al. | |
| 2013/0075716 A1 | 3/2013 | Nishimura et al. | |
| 2013/0092913 A1 | 4/2013 | Nishimura et al. | |
| 2013/0112950 A1 | 5/2013 | Yokoyama et al. | |
| 2013/0270540 A1 | 10/2013 | Numata | |
| 2013/0292664 A1 | 11/2013 | Nishimura et al. | |
| 2013/0306959 A1 | 11/2013 | Ikeda et al. | |
| 2013/0306962 A1 | 11/2013 | Yamamoto et al. | |
| 2013/0306963 A1 | 11/2013 | Yamamoto et al. | |
| 2013/0341612 A1 | 12/2013 | Oohisa et al. | |
| 2014/0001449 A1 * | 1/2014 | Maunoury et al. | 257/40 |
| 2014/0008633 A1 | 1/2014 | Kato et al. | |
| 2014/0027750 A1 | 1/2014 | Yu et al. | |
| 2014/0034940 A1 | 2/2014 | Yu et al. | |
| 2014/0048784 A1 | 2/2014 | Inoue et al. | |
| 2014/0070204 A1 | 3/2014 | Nagan et al. | |
| 2014/0084271 A1 | 3/2014 | Lee et al. | |
| 2014/0110692 A1 | 4/2014 | Kato et al. | |
| 2014/0159023 A1 | 6/2014 | Matsumoto et al. | |
| 2014/0167026 A1 | 6/2014 | Kato et al. | |
| 2014/0203251 A1 | 7/2014 | Jung et al. | |
| 2014/0217393 A1 | 8/2014 | Kato et al. | |

FOREIGN PATENT DOCUMENTS

| | | | | |
|---|---|---|---|---|
| CN | 102702132 | | 10/2012 | |
| EP | 1 798 804 | | 6/2007 | |
| EP | 2 471 771 | | 7/2012 | |
| EP | 2 762 478 | | 8/2014 | |
| JP | 2009120582 | * | 6/2009 | ........... C07D 209/80 |
| JP | 2010-195708 | | 9/2010 | |
| JP | 2011-176258 | | 9/2011 | |
| JP | 2012-175025 | | 9/2012 | |
| JP | 2012-216801 | | 11/2012 | |
| JP | 2013-089928 | | 5/2013 | |
| KR | 10-2010-0021367 | | 2/2010 | |
| KR | 10-2011-0041727 | | 4/2011 | |
| KR | 10-2011-0102055 | | 9/2011 | |
| KR | 10-1072817 | | 10/2011 | |
| KR | 10-2012-0112277 | | 10/2012 | |
| KR | 10-2012-0122812 | | 11/2012 | |
| KR | 10-2012-0122813 | | 11/2012 | |
| WO | 01/41512 | | 6/2001 | |
| WO | 2010/114264 | | 10/2010 | |
| WO | 2010/134350 A1 | | 11/2010 | |
| WO | 2010/140482 | | 12/2010 | |
| WO | 2011/019156 | | 10/2011 | |
| WO | 2011/132684 A1 | | 10/2011 | |
| WO | 2011/162162 | | 12/2011 | |
| WO | 2013/022419 | | 2/2013 | |
| WO | 2013/027906 | | 2/2013 | |
| WO | 2013/057908 | | 4/2013 | |
| WO | 2013/057922 | | 4/2013 | |
| WO | 2013/058343 | | 4/2013 | |
| WO | 2013/062075 | | 5/2013 | |

OTHER PUBLICATIONS

Thomas et al. "Cyanocarbazole Derivatives for High-Performance Electroluminescent Devices" Adv. Funct. Mater. 2004, 14(4), 387-392.*
U.S. Appl. No. 13/705,686, filed Dec. 5, 2012, Mizuki, et al.
U.S. Appl. No. 13/760,928, filed Feb. 6, 2013, Mizuki, et al.
U.S. Appl. No. 14/318,738, Jun. 30, 2014, Inoue, et al.
Supplementary European Search Report issued Jun. 5, 2015 in connection with corresponding European Patent Application No. 12 85 5216, filed Dec. 4, 2012.
International Search Report issued Mar. 12, 2013 in connection with PCT/JP2012/081382.
International Search Report issued Mar. 5, 2013 in connection with PCT/JP2012/081375.
James F. Ambrose, et al. "Electrochemical and Spectroscopic Properties of Cation Radicals", J. Electrochem. Soc.; Electrochemical Science and Technology, vol. 122, No. 7, pp. 876-894. (Jun. 1975).

* cited by examiner

HOMO

LUMO

HOMO

LUMO

HOMO

LUMO

MATERIAL FOR ORGANIC ELECTROLUMINESCENCE DEVICE AND ORGANIC ELECTROLUMINESCENCE DEVICE

TECHNICAL FIELD

The present invention relates to materials for organic electroluminescence devices and organic electroluminescence devices employing the materials.

BACKGROUND ART

By applying voltage to an organic electroluminescence device (also referred to as "organic EL device"), holes from an anode and electrons from a cathode are injected into a light emitting layer. The holes and electrons injected into the light emitting layer recombine to form excitons. The singlet exciton and the triplet exciton are formed at a ratio of 25%:75% according to spin-statistics theorem. Since the fluorescence utilizes the emission from singlet excitons, it has been known that the internal quantum efficiency of a fluorescent organic EL device is limited to 25%. In contrast, since the phosphorescence utilizes the emission from triplet excitons, it has been known that the internal quantum efficiency of a phosphorescent organic EL device can be increased to 100% if the intersystem crossing occurs efficiently.

In the development of known organic EL devices, an optimum device design has been made depending upon the emission mechanism such as fluorescence and phosphorescence. It has been known in the art that a high-performance phosphorescent organic EL device cannot be obtained by a mere application of the fluorescent technique to the phosphorescent device, because the emission mechanisms are different from each other. This may be generally because the following reasons.

Since the phosphorescence utilizes the emission from triplet excitons, a compound with larger energy gap is required to be used in the light emitting layer. This is because that the singlet energy (energy difference between the lowest excited singlet state and the ground state) of a compound is generally larger than its triplet energy (energy difference between the lowest excited triplet state and the ground state).

Therefore, to effectively confine the triplet energy of a phosphorescent dopant material within a device, a host material having triplet energy larger than that of the phosphorescent dopant material should be used in the light emitting layer. In addition, if an electron transporting layer and a hole transporting layer is formed adjacent to the light emitting layer, a compound having triplet energy larger than that of the phosphorescent dopant material should be used also in the electron transporting layer and the hole transporting layer. Thus, the device design conventionally employed for developing a phosphorescent organic EL device results in the use of a compound having an energy gap larger than that of a compound for use in a fluorescent organic EL device, thereby increasing the voltage for driving an organic EL device.

A hydrocarbon compound highly resistant to oxidation and reduction, which has been known as a useful compound for a fluorescent device, has a small energy gap because of a broad distribution of π-electron cloud. Therefore, such a hydrocarbon compound is not suitable for use in a phosphorescent organic EL device and, instead, an organic compound having a heteroatom, such as oxygen and nitrogen, has been selected. However, a phosphorescent organic EL device employing such an organic compound having a heteroatom has a shorter lifetime as compared with a fluorescent organic EL device.

In addition, a phosphorescent dopant material has an extremely longer relaxation time of triplet excitons as compared with that of its singlet excitons, this largely affecting the device performance. Namely, in the emission from singlet excitons, since the relaxation speed which leads to emission is high, the diffusion of excitons into a layer adjacent to the light emitting layer (for example, a hole transporting layer and an electron transporting layer) is difficult to occur and efficient emission is expected. In contrast, the emission from triplet excitons is a spin-forbidden transition and the relaxation speed is low. Therefore, the diffusion of excitons into adjacent layers occurs easily and the thermal energy deactivation occurs in most compounds other than the specific phosphorescent compound. Thus, as compared with a fluorescent organic EL device, it is more important for a phosphorescent organic EL device to control the region for recombining electrons and holes.

For the above reasons, the development of a high performance phosphorescent organic EL device requires the selection of materials and the consideration of device design which are different from those for a fluorescent organic EL device.

A carbazole derivative having a high triplet energy and a carbazole skeleton known as a principal skeleton of hole transporting materials has been conventionally used as a useful phosphorescent host material.

Patent Document 1 describes, as a material for organic EL device, a compound in which a nitrogen-containing heterocyclic group is introduced into a biscarbazole skeleton which includes two carbazole structures connected to each other. The compound described in Patent Document 1 is molecularly designed to balance the charge transport by introducing an electron-deficient nitrogen-containing heterocyclic group to a hole transporting carbazole skeleton. Patent Document 2 describes that the charge injecting ability of a N,N-biscarbazole compound wherein two carbazole structures are bonded to each other via a biphenyl group is improved by introducing an electron-withdrawing group into the intervening biphenyl group between two carbazole structures.

However, the improvement of the emission efficiency of organic EL device is still required and the development of a new material for organic EL device which realizes higher emission efficiency has been demanded.

PRIOR ART

Patent Documents

Patent Document 1: WO 2011/132684
Patent Document 2: JP 2011-176258

SUMMARY OF THE INVENTION

Problem to be Solved by the Invention

An object of the invention is to provide a material for organic electroluminescence device capable of realizing an organic electroluminescence device with good emission efficiency and an organic electroluminescence device employing the material.

Means for Solving Problem

As a result of extensive research, the inventors have found that a material for organic EL device represented by formula (I) realizes an organic EL device with excellent emission efficiency and made the invention based on this finding. The material for organic EL device represented by formula (I) has a central skeleton to which a cyano-substituted aromatic hydrocarbon group or a cyano-substituted heterocyclic group is bonded at a specific position.

The present invention provides:

1. A material for organic electroluminescence device represented by formula (I):

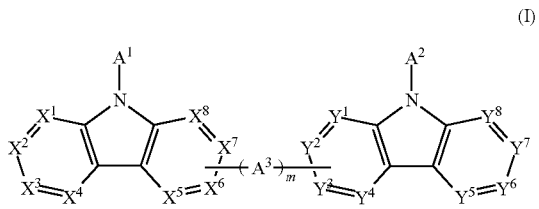

wherein:

each of $A^1$ and $A^2$ independently represents a substituted or unsubstituted aromatic hydrocarbon group having 6 to 30 ring carbon atoms or a substituted or unsubstituted heterocyclic group having 5 to 30 ring atoms;

$A^3$ represents a substituted or unsubstituted monocyclic hydrocarbon group having 6 or less ring carbon atoms or a substituted or unsubstituted monocyclic heterocyclic group having 6 or less ring atoms;

m represents an integer of 0 to 3;

each of $X^1$ to $X^8$ and $Y^1$ to $Y^8$ independently represents N or $CR^a$;

each of $R^a$ independently represents a hydrogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group, or a halogen atom, provided that one of $X^5$ to $X^8$ and one of $Y^1$ to $Y^4$ are bonded to each other via $A^3$ or directly; and the formula (I) satisfies at least one of the following requirements (i) and (ii):

(i) at least one of $A^1$ and $A^2$ represents a cyano-substituted aromatic hydrocarbon group having 6 to 30 ring carbon atoms or a cyano-substituted heterocyclic group having 5 to 30 ring atoms; and (ii) at least one of $X^1$ to $X^4$ and $Y^5$ to $Y^8$ represents $CR^a$, and at least one of $R^a$ in $X^1$ to $X^4$ and $Y^5$ to $Y^8$ represents a cyano-substituted aromatic hydrocarbon group having 6 to 30 ring carbon atoms or a cyano-substituted heterocyclic group having 5 to 30 ring atoms, provided that when two or more $R^a$ groups exist, the $R^a$ groups may be the same or different;

2. The material for organic electroluminescence device according to item 1, wherein an optional substituent of the aromatic hydrocarbon group having 6 to 30 ring carbon atoms or the heterocyclic group having 5 to 30 ring atoms of $A^1$ and $A^2$ is at least one group selected from a cyano group, a halogen atom, an alkyl group having 1 to 20 carbon atoms, a cycloalkyl group having 3 to 20 carbon atoms, an alkoxyl group having 1 to 20 carbon atoms, a haloalkyl group having 1 to 20 carbon atoms, a haloalkoxyl group having 1 to 20 carbon atoms, an alkylsilyl group having 1 to 10 carbon atoms, an aryl group having 6 to 30 ring carbon atoms, an aryloxy group having 6 to 30 ring carbon atoms, an aralkyl group having 6 to 30 carbon atoms, and a heteroaryl group having 5 to 30 ring atoms;

3. The material for organic electroluminescence device according to item 1 or 2, which satisfies the requirement (i) but does not satisfy the requirement (ii);

4. The material for organic electroluminescence device according to item 1 or 2, which satisfies the requirement (ii) but does not satisfy the requirement (i);

5. The material for organic electroluminescence device according to item 1 or 2, which satisfies both the requirements (i) and (ii);

6. The material for organic electroluminescence device according to any one of items 1 to 3 and 5, wherein at least one of $A^1$ and $A^2$ represents a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group;

7. The material for organic electroluminescence device according to any one of items 1 to 3, 5 and 6, wherein $A^1$ is substituted by a cyano group and $A^2$ is not substituted by a cyano group;

8. The material for organic electroluminescence device according to any one of items 1, 4 and 5, wherein at least one of $X^1$ to $X^4$ and $Y^5$ to $Y^8$ represents $CR^a$, and at least one of $R^a$ in $X^1$ to $X^4$ and $Y^5$ to $Y^8$ represents a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group;

9. The material for organic electroluminescence device according to any one of items 1 to 8, wherein $X^6$ and $Y^3$ are bonded to each other via $A^3$ or directly;

10. The material for organic electroluminescence device according to any one of items 1 to 8, wherein $X^6$ and $Y^2$ are bonded to each other via $A^3$ or directly;

11. The material for organic electroluminescence device according to any one of items 1 to 8, wherein $X^7$ and $Y^3$ are bonded to each other via $A^3$ or directly;

12. The material for organic electroluminescence device according to any one of items 1 to 11, wherein m represents 0;

13. The material for organic electroluminescence device according to any one of items 1 to 11, wherein m represents 1;

14. An organic electroluminescence device comprising an organic thin film layer comprising one or more layers between a cathode and an anode, wherein the organic thin film layer comprises a light emitting layer, and at least one layer of the organic thin film layer comprises the material for organic electroluminescence device according to any one of items 1 to 13;

15. The organic electroluminescence device according to item 14, wherein the light emitting layer comprises the material for organic electroluminescence device;

16. The organic electroluminescence device according to item 14 or 15, wherein the light emitting layer comprises a phosphorescent material selected from ortho metallated complexes of a metal selected from iridium (Ir), osmium (Os), and platinum (Pt);

17. The organic electroluminescence device according to any one of items 14 to 16, which further comprises a layer adjacent to the light emitting layer between the cathode and the light emitting layer, and the layer adjacent to the light emitting layer comprises the material for organic electroluminescence device; and 18. The organic electroluminescence device according to any one of items 14 to 16, which further comprises a blocking layer adjacent to the light emitting layer between the cathode and the light emitting layer, and the blocking layer comprises the material for organic electroluminescence device according to any one of items 1 to 13.

Effect of the Invention

According to the present invention, an organic electroluminescence device with good emission efficiency and a material for organic electroluminescence device which realizes such organic electroluminescence device are provided.

MODE FOR CARRYING OUT THE INVENTION

Figure 1:
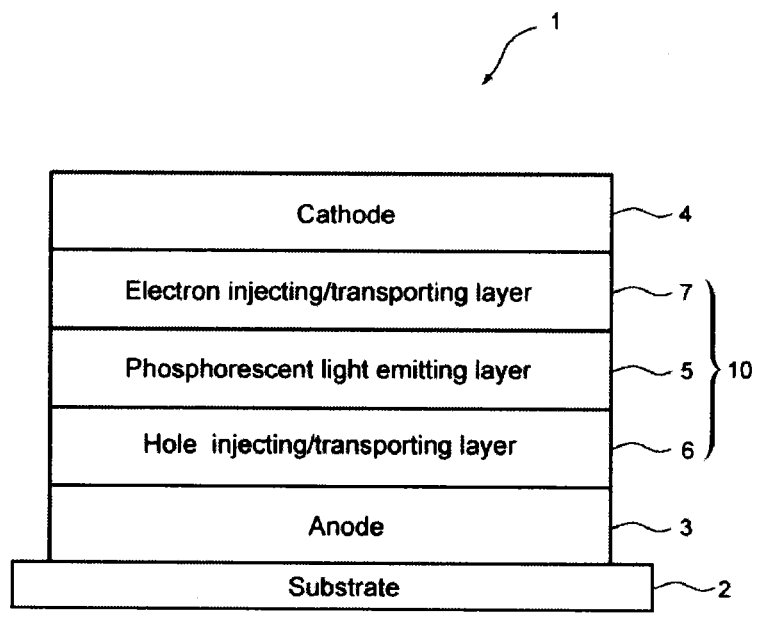
FIG. 1 is a schematic cross-sectional view of an example of the organic EL device of the invention.

Material for Organic Electroluminescence Device
The material for organic electroluminescence device (hereinafter also referred to as "material for organic EL device") of the invention is represented by formula (I):

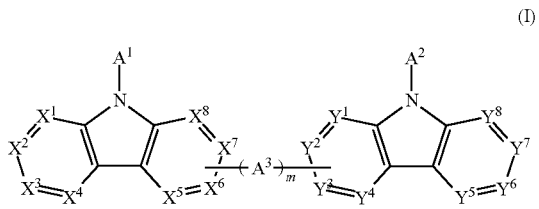

wherein:
each of $A^1$ and $A^2$ independently represents a substituted or unsubstituted aromatic hydrocarbon group having 6 to 30 ring carbon atoms or a substituted or unsubstituted heterocyclic group having 5 to 30 ring atoms;
$A^3$ represents a substituted or unsubstituted monocyclic hydrocarbon group having 6 or less ring carbon atoms or a substituted or unsubstituted monocyclic heterocyclic group having 6 or less ring atoms;
m represents an integer of 0 to 3;
each of $X^1$ to $X^8$ and $Y^1$ to $Y^8$ independently represents N or $CR^a$;
each of $R^a$ independently represents a hydrogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group, or a halogen atom, provided that one of $X^5$ to $X^8$ and one of $Y^1$ to $Y^4$ are bonded to each other via $A^3$ or directly; and
the formula (I) satisfies at least one of the following requirements (i) and (ii):
(i) at least one of $A^1$ and $A^2$ represents a cyano-substituted aromatic hydrocarbon group having 6 to 30 ring carbon atoms or a cyano-substituted heterocyclic group having 5 to 30 ring atoms; and (ii) at least one of $X^1$ to $X^4$ and $Y^5$ to $Y^8$ represents $CR^a$, and at least one of $R^a$ in $X^1$ to $X^4$ and $Y^5$ to $Y^8$ represents a cyano-substituted aromatic hydrocarbon group having 6 to 30 ring carbon atoms or a cyano-substituted heterocyclic group having 5 to 30 ring atoms, provided that when two or more $R^a$ groups exist, the $R^a$ groups may be the same or different.

The cyano-substituted aromatic hydrocarbon group having 6 to 30 ring carbon atoms and the cyano-substituted heterocyclic group having 5 to 30 ring atoms of formula (I) may be further substituted by a group other than the cyano group.
The subscript m is preferably 0 to 2 and more preferably 0 or 1. When m is 0, one of $X^5$ to $X^8$ and one of $Y^1$ to $Y^4$ are bonded to each other via a single bond.

The aromatic hydrocarbon group having 6 to 30 ring carbon atoms represented by $A^1$, $A^2$ and $R^a$ may be a non-condensed aromatic hydrocarbon group or a condensed aromatic hydrocarbon group. Specific examples thereof include phenyl group, naphthyl group, phenanthryl group, biphenyl group, terphenyl group, quaterphenyl group, fluoranthenyl group, triphenylenyl group, phenanthrenyl group, fluorenyl group, spirofluorenyl group, 9,9-diphenylfluorenyl group, 9,9'-spirobi[9H-fluorene]-2-yl group, 9,9-dimethylfluorenyl group, benzo[c]phenanthrenyl group, benzo[a]triphenylenyl group, naphtho[1,2-c]phenanthrenyl group, naphtho[1,2-a]triphenylenyl group, dibenzo[a,c]triphenylenyl group, and benzo[b]fluoranthenyl group, with phenyl group, naphthyl group, biphenyl group, terphenyl group, phenanthryl group, triphenylenyl group, fluorenyl group, spirobifluorenyl group, and fluoranthenyl group being preferred, and phenyl group, 1-naphthyl group, 2-naphthyl group, biphenyl-2-yl group, biphenyl-3-yl group, biphenyl-4-yl group, phenanthrene-9-yl group, phenanthrene-3-yl group, phenanthrene-2-yl group, triphenylene-2-yl group, 9,9-dimethylfluorene-2-yl group, fluoranthene-3-yl group being more preferred.

The heterocyclic group having 5 to 30 ring atoms represented by $A^1$, $A^2$ and $R^a$ may be a non-condensed heterocyclic group or a condensed heterocyclic group. Specific examples thereof include the residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazole ring, thiadiazole ring, benzothiazole ring, triazole ring, imidazole ring, benzimidazole ring, pyran ring, dibenzofuran ring, and benzo[c]dibenzofuran ring, and the residues of derivatives of these rings, with the residues of dibenzofuran ring, carbazole ring, dibenzothiophene ring, and derivatives of these rings being preferred, and the residues of dibenzofuran-2-yl group, dibenzofuran-4-yl group, 9-phenylcarbazole-3-yl group, 9-phenylcarbazole-2-yl group, dibenzothiophene-2-yl group, and dibenzothiophene-4-yl group being more preferred.

Examples of the monocyclic hydrocarbon group having 6 or less ring carbon atoms represented by $A^3$ include phenylene group, cyclopentenylene group, cyclopentadienylene group, cyclohexylene group, and cyclopentylene group, with phenylene group being preferred.

Examples of the monocyclic heterocyclic group having 6 or less ring atoms represented by $A^3$ include pyrrolylene group, pyrazinylene group, pyridinylene group, furylene group, and thiophenylene group.

Examples of the alkyl group having 1 to 30 carbon atoms represented by $R^a$ include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, cyclopropyl group, cyclobutyl group, cyclopentyl group, cyclohexyl group, cyclooctyl group, and adamantyl group, with methyl group, ethyl group, n-propyl group, isopropyl group, n-butyl group, s-butyl group, isobutyl group, t-butyl group, cyclopentyl group, and cyclohexyl group being preferred.

Examples of the substituted or unsubstituted silyl group represented by $R^a$ include trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, diethylisopropylsilyl group, phenyldimethylsilyl group, diphenylmethylsilyl group, diphenyltertiarybutylsilyl group, and triphenylsilyl group, with trimethylsilyl group, triethylsilyl group, t-butyldimethylsilyl group, vinyldimethylsilyl group, and propyldimethylsilyl group being preferred.

Examples of the halogen atom represented by $R^a$ include fluorine, chlorine, bromine, and iodine, with fluorine being preferred.

Also preferred as $R^a$ is a hydrogen atom or a substituted or unsubstituted aromatic hydrocarbon group having 6 to 30 ring carbon atoms.

Examples of the optional substituent indicated by "substituted or unsubstituted" and "may be substituted" referred to above or hereinafter include a halogen atom (fluorine, chlorine, bromine, iodine), a cyano group, an alkyl group having 1 to 20, preferably 1 to 6 carbon atoms, a cycloalkyl group having 3 to 20, preferably 5 to 12 carbon atoms, an alkoxyl group having 1 to 20, preferably 1 to 5 carbon atoms, a haloalkyl group having 1 to 20, preferably 1 to 5 carbon atoms, a haloalkoxyl group having 1 to 20, preferably 1 to 5 carbon atoms, an alkylsilyl group having 1 to 10, preferably 1 to 5 carbon atoms, an aryl group having 6 to 30, preferably 6 to 18 ring carbon atoms, an aryloxy group having 6 to 30, preferably 6 to 18 ring carbon atoms, an arylsilyl group having 6 to 30, preferably 6 to 18 carbon atoms, an aralkyl group having 7 to 30, preferably 7 to 20 carbon atoms, and a heteroaryl group having 5 to 30, preferably 5 to 18 ring atoms.

Examples of the optional alkyl group having 1 to 20 carbon atoms include methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, and 1-methylpentyl group.

Examples of the optional cycloalkyl group having 3 to 20 carbon atoms include cyclopropyl group, cyclobutyl group, cyclopentyl group, cyclohexyl group, cyclooctyl group, and adamantyl group.

Examples of the optional alkoxyl group having 1 to 20 carbon atoms include those having an alkyl portion selected from the alkyl groups mentioned above.

Examples of the optional haloalkyl group having 1 to 20 carbon atoms include the alkyl groups mentioned above wherein the hydrogen atoms thereof are partly or entirely substituted by halogen atoms.

Examples of the optional haloalkoxyl group having 1 to 20 carbon atoms include the alkoxyl group mentioned above wherein the hydrogen atoms thereof are partly or entirely substituted by halogen atoms.

Examples of the optional alkylsilyl group having 1 to 10 carbon atoms include trimethylsilyl group, triethylsilyl group, tributylsilyl group, dimethylethylsilyl group, t-butyldimethylsilyl group, vinyldimethylsilyl group, propyldimethylsilyl group, dimethylisopropylsilyl group, dimethylpropylsilyl group, dimethylbutylsilyl group, dimethyltertiarybutylsilyl group, and diethylisopropylsilyl group.

Examples of the optional aromatic hydrocarbon group having 6 to 30 ring carbon atoms include those selected from the aromatic hydrocarbon groups mentioned above with respect to $A^1$, $A^2$ and $R^a$.

Examples of the optional aryloxy group having 6 to 30 ring carbon atoms include those having an aryl portion selected from the aromatic hydrocarbon groups mentioned above.

Examples of the optional arylsilyl group having 6 to 30 carbon atoms include phenyldimethylsilyl group, diphenylmethylsilyl group, diphenyltertiarybutylsilyl group, and triphenylsilyl group.

Examples of the optional aralkyl group having 7 to 30 carbon atoms include benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

Examples of the optional heteroaryl group having 5 to 30 ring atoms include those selected from the heterocyclic groups mentioned above with respect to $A^1$, $A^2$ and $R^a$.

The optional substituent is preferably fluorine atom, cyano group, the alkyl group having 1 to 20 carbon atoms, the aromatic hydrocarbon group having 6 to 30 ring carbon atoms, and the heteroaryl group having 5 to 30 ring atoms, more preferably fluorine atom, phenyl group, naphthyl group, biphenyl group, terphenyl group, phenanthryl group, triphenylenyl group, fluorenyl group, spirobifluorenyl group, fluoranthenyl group, residues of dibenzofuran ring, carbazole ring, dibenzothiophene ring, and their derivatives, methyl group, ethyl group, n-propyl group, isopropyl group, n-butyl group, s-butyl group, isobutyl group, t-butyl group, cyclopentyl group, and cyclohexyl group.

The optional substituent mentioned above may be further substituted by the optional group mentioned above.

In formula (I), the optional substituent of the aromatic hydrocarbon group having 6 to 30 ring carbon atoms or the heterocyclic group having 5 to 30 ring atoms represented by $A^1$ and $A^2$ is preferably at least one group selected from a cyano group, a halogen atom, an alkyl group having 1 to 20 carbon atoms, a cycloalkyl group having 3 to 20 carbon atoms, an alkoxyl group having 1 to 20 carbon atoms, a haloalkyl group having 1 to 20 carbon atoms, a haloalkoxyl group having 1 to 20 carbon atoms, an alkylsilyl group having 1 to 10 carbon atoms, an aryl group having 6 to 30 ring carbon atoms, an aryloxy group having 6 to 30 ring carbon atoms, an aralkyl group having 6 to 30 carbon atoms, and a heteroaryl group having 5 to 30 ring atoms. Examples of such substituents of $A^1$ and $A^2$ are the same as those described with respect to the optional substituents mentioned above.

In formula (I), at least one of $A^1$ and $A^2$ is preferably the cyano-substituted aromatic hydrocarbon group having 6 to 30 ring carbon atoms or the cyano-substituted heterocyclic group having 5 to 30 ring atoms, at least one of $X^1$ to $X^4$ and $Y^5$ to $Y^8$ is preferably $CR^a$, and at least one of $R^a$ in $X^1$ to $X^4$ and $Y^5$ to $Y^8$ is preferably the cyano-substituted aromatic hydrocarbon group having 6 to 30 ring carbon atoms or the cyano-substituted heterocyclic group having 5 to 30 ring atoms.

The "carbon number of a to b" in the expression of "substituted or unsubstituted X group having carbon number of a to b" is the carbon number of the unsubstituted X group and does not include the carbon atom of the optional substituent.

The hydrogen atom referred to herein includes isotopes different from neutron numbers, i.e., light hydrogen (protium), heavy hydrogen (deuterium) and tritium.

In the material for organic EL device of the invention, the groups represented by formulae (a) and (b) are bonded to each other via $-(A^3)_m-$ at one of $X^5$ to $X^8$ and one of $Y^1$ to $Y^4$. Specific examples of the bonding manner between formulae (a) and (b) are represented by $X^6-(A^3)_m-Y^3$, $X^6-(A^3)_m-Y^2$, $X^6-(A^3)_m-Y^4$, $X^6-(A^3)_m-Y^1$, $X^7-(A^3)_m-Y^3$, $X^5-(A^3)_m-Y^3$, $X^8-(A^3)_m-Y^3$, $X^7-(A^3)_m-Y^2$, $X^7-(A^3)_m-Y^4$, $X^7-(A^3)_m-Y^1$, $X^5-(A^3)_m-Y^2$, $X^8-(A^3)_m-Y^2$, $X^8-(A^3)_m-Y^4$, $X^8-(A^3)_m-Y^1$, $X^5-(A^3)_m-Y^1$, and $X^5-(A^3)_m-Y^4$.

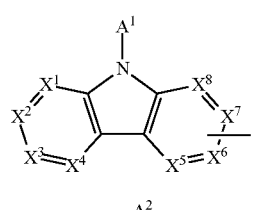

(a)

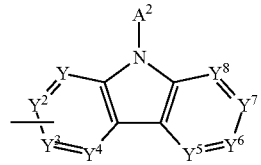

(b)

In preferred embodiments of the material for organic electroluminescence device of the invention, the bonding manner between formulae (a) and (b) are represented by $X^6-(A^3)_m-Y^3$, $X^6-(A^3)_m-Y^2$, or $X^7-(A^3)_m-Y^3$, namely the material for organic electroluminescence device is preferably represented by formula (II), (III), or (IV):

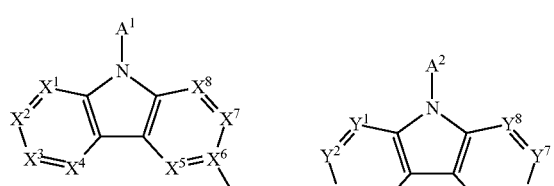

(II)

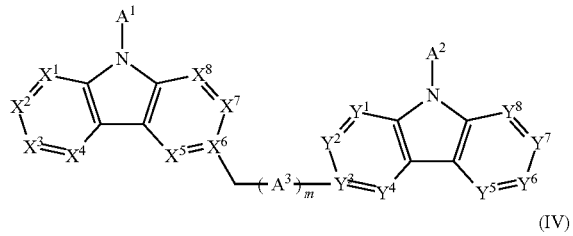

(III)

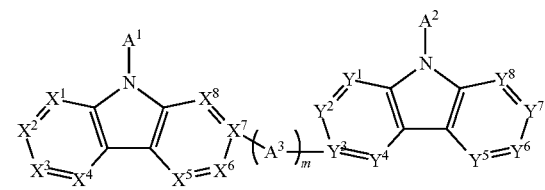

(IV)

wherein $X^1$ to $X^8$, $Y^1$ to $Y^8$, $A^1$ to $A^3$, and m are the same as $X^1$ to $X^8$, $Y^1$ to $Y^8$, $A^1$ to $A^3$, m in formula (I), and each of formulae (II), (III), and (IV) satisfies at least one requirement (i) and (ii) as specified in the definition of formula (I).

$A^3$ in formulae (I) to (IV) represents a single bond, a substituted or unsubstituted monocyclic hydrocarbon group having 6 or less ring carbon atoms, or a substituted or unsubstituted monocyclic heterocyclic group having 6 or less ring atoms. $A^3$ minimizes the distortion of the ring (for example, carbazole ring) represented by formula (a) or (b) to make it easy to retain the conjugation of π-electrons. This allows HOMO (highest occupied molecular orbital) to extend throughout the whole carbazole skeleton, thereby to retain the hole injecting/transporting ability of the carbazole skeleton. $A^3$ is preferably a single bond or a substituted or unsubstituted phenylene group.

In formulae (I) to (IV), m is preferably 0 or 1. When m is 1, $A^3$ is preferably a substituted or unsubstituted phenylene group.

The material for organic EL device of the invention satisfies at least one of the requirements (i) and (ii):
(i) at least one of $A^1$ and $A^2$ is substituted by a cyano group; and
(ii) at least one of $X^1$ to $X^4$ and $Y^5$ to $Y^8$ represents $CR^a$, and at least one of $R^a$ in $X^1$ to $X^4$ and $Y^5$ to $Y^8$ represents the cyano-substituted aromatic hydrocarbon group having 6 to 30 ring carbon atoms or the cyano-substituted heterocyclic group having 5 to 30 ring atoms.

Namely, the material for organic EL device of the invention is any one of the compounds:
(1) satisfying the requirement (i), but not satisfying the requirement (ii);
(2) satisfying the requirement (ii), but not satisfying the requirement (i); and
(3) satisfying both the requirements (i) and (ii).

In the material for organic EL device of the invention, by introducing the cyano-substituted aromatic hydrocarbon group or the cyano-substituted heterocyclic group into the terminal end of the central skeleton comprising formulae (a) and (b), for example, a carbazolyl group, the hole injecting/transporting ability of the carbazolyl skeleton and the electron injecting/transporting ability of the cyano group are prevented from counteracting to each other, thereby making the carrier balance in the molecule good.

The electron injecting/transporting cyano-substituted aromatic hydrocarbon group and cyano-substituted heterocyclic group are more resistant to holes as compared with a nitrogen-containing heterocycle, such as a pyrimidine ring and a triazine ring, as described in Patent Document 1. Therefore, an organic EL device employing the material for organic EL device of the invention has a longer lifetime as compared with the device employing the compound described in Patent Document 1.

When the material for organic EL device of the invention satisfies the requirement (i), at least one of $A^1$ and $A^2$ is preferably a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9'-dimethylfluorenyl group, or a cyano-substituted triphenylenyl group, and more preferably 3'-cyanobiphenyl-2-yl group, 3'-cyanobiphenyl-3-yl group, 3'-cyanobiphenyl-4-yl group, 4'-cyanobiphenyl-3-yl group, 4'-cyanobiphenyl-4-yl group, 4'-cyanobiphenyl-2-yl group, 6-cyanonaphthalene-2-yl group, 4-cyanonaphthalene-1-yl group, 7-cyanonaphthalene-2-yl group, 8-cyanodibenzofuran2-yl group, 6-cyanodibenzofuran4-yl group, 8-cyanodibenzothiophene-2-yl group, 6-cyanodibenzothiophene-4-yl group, 7-cyano9-phenylcarbazole-2-yl group, 6-cyano9-phenylcarbazole-3-yl group, 7-cyano9,9-dimethylfluorene-2-yl group, or 7-cyanotriphenylene-2-yl group.

The material for organic EL device of the invention wherein $A^1$ is substituted by a cyano group and $A^2$ is not substituted by a cyano group is preferred. In this case, the material for organic EL device of the invention which does not satisfy the requirement (ii) is more preferred.

When the material for organic EL device of the invention satisfies the requirement (ii), at least one of $X^1$ to $X^4$ and $Y^5$ to $Y^8$ is preferably $CR^a$, and one of $R^a$ in $X^1$ to $X^4$ and $Y^5$ to $Y^8$ is preferably a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9'-dimethylfluorenyl group, or a cyano-substituted triphenylenyl group, and more preferably 3'-cyanobiphenyl-2-yl group, 3'-cyanobiphenyl-3-yl group, 3'-cyanobiphenyl-4-yl group, 4'-cyanobiphenyl-3-yl group, 4'-cyanobiphenyl-4-yl group, 4'-cyanobiphenyl-2-yl group, 6-cyanonaphthalene-2-yl group, 4-cyanonaphthalene-1-yl group, 7-cyanonaphthalene-2-yl group, 8-cyanodibenzofuran2-yl group, 6-cyanodibenzofuran4-yl group, 8-cyanodibenzothiophene-2-yl group, 6-cyanodibenzothiophene-4-yl group, 7-cyano9-phenylcarbazole-2-yl group, 6-cyano9-phenylcarbazole-3-yl group, 7-cyano9,9-dimethylfluorene-2-yl group, or 7-cyanotriphenylene-2-yl group.

It is preferred for the material for organic EL device of the invention to satisfy the requirement (ii), but not satisfy the requirement (i).

In the formulae (I) to (IV), $A^1$ and $A^2$ are preferably different from each other, and more preferably, $A^1$ is substituted by a cyano group but $A^2$ is not substituted by a cyano group. Namely, the material for organic EL device of the invention is preferably structurally asymmetric. If being asymmetric, the crystallinity and non-crystallinity are good. This enhances the quality of the films of an organic EL device employing the material for organic EL device, thereby achieving high performance, for example, organic EL properties, such as current efficiency.

The material for organic EL device of the invention is characterized by the central skeleton comprising the groups represented by formulae (a) and (b), to the terminal end of which a cyano group-containing aromatic hydrocarbon group or a cyano group-containing heterocyclic group is introduced.

The central skeleton comprising the groups represented by formulae (a) and (b) acts as a hole injecting/transporting unit, and each of the cyano group-containing aromatic hydrocarbon group and the cyano group-containing heterocyclic group acts as an electron injecting/transporting unit. Since the material for organic EL device of the invention has the cyano group-containing group which acts as an electron injecting/transporting unit outside the central skeleton, the distribution of the electron cloud of HOMO (highest occupied molecular orbital) is retained within the central skeleton, to maintain the hole injecting/transporting ability of the central skeleton good while retaining the electron injecting/transporting ability of the cyano group-containing group. Therefore, the carrier balance in the molecule of the material for organic EL device of the invention is good to realize an organic EL device with excellent emission efficiency.

Figure 2:
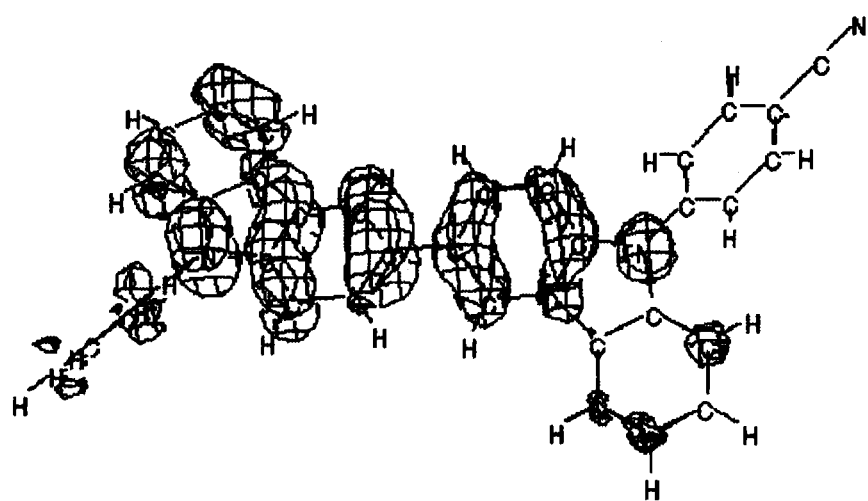
FIG. 2 is a diagram showing the result of molecular orbital calculation of HOMO and LUMO of the compound 1 within the material for organic EL device of the invention.
Figure 2:
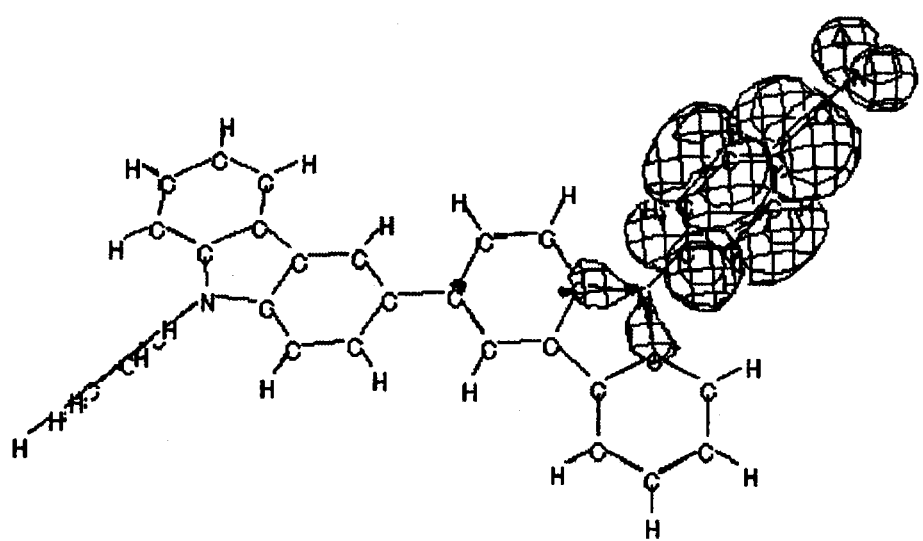

As an example, the result of molecular orbital calculation on the compound 1 of the invention is shown in FIG. 2. As seen from FIG. 2, HOMO of the compound 1 is distributed through the central skeleton having two carbazolyl groups, to show a good hole injecting/transporting ability. LUMO (lowest unoccupied molecular orbital) of the compound 1 is distributed mainly though the cyano group-containing aromatic hydrocarbon group (4-cyanophenyl group). Since the electron distributions of HOMO and LUMO are separated, the carrier balance between the hole injecting/transporting ability and the electron injecting/transporting ability in the molecule of the compound 1 is well, to make it possible to realize an organic EL device with high emission efficiency.

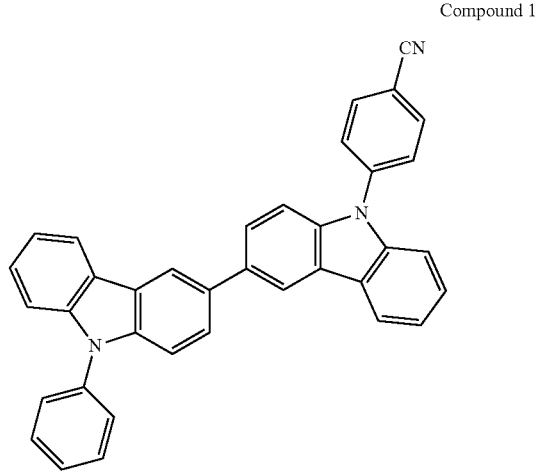 [SMILES: N#Cc1ccc(-n2c3ccccc3c3cc(-c4ccc5c(c4)c4ccccc4n5-c4ccccc4)ccc32)cc1]

Compound 1

Figure 3:
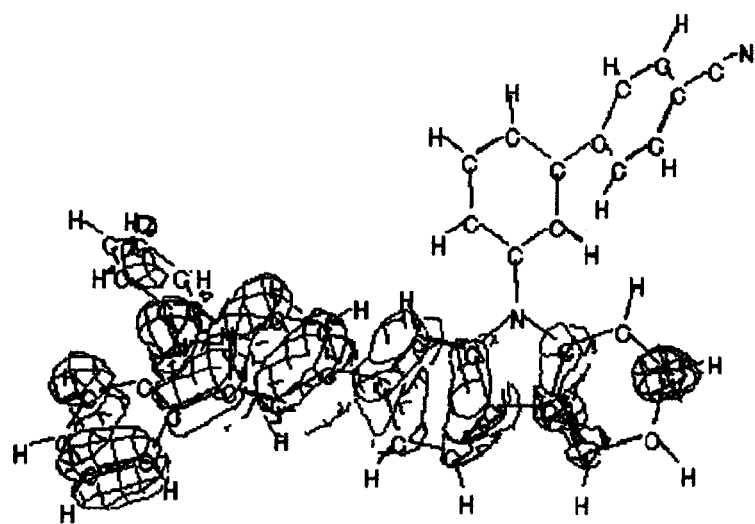
FIG. 3 is a diagram showing the result of molecular orbital calculation of HOMO and LUMO of the compound 2 within the material for organic EL device of the invention.
Figure 3:
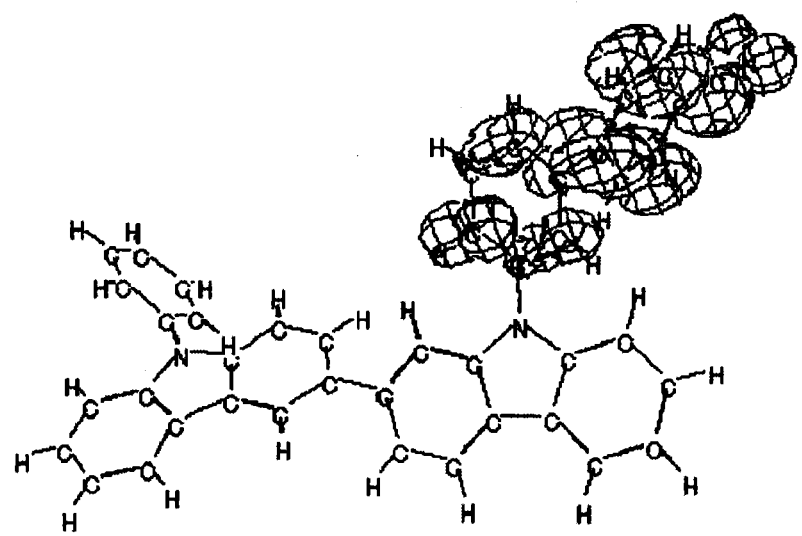

As another example, the result of molecular orbital calculation on the compound 2 of the invention is shown in FIG. 3. As seen from FIG. 3, HOMO of the compound 2 is distributed through the central skeleton having two carbazolyl groups, to show a good hole injecting/transporting ability. LUMO of the compound 2 is distributed though the cyano group-containing aromatic hydrocarbon group (4-cyanobiphenyl group). Since the electron distributions of HOMO and LUMO are separated, the carrier balance between the hole injecting/transporting ability and the electron injecting/transporting ability in the molecule of the compound 2 is well, to make it possible to realize an organic EL device with high emission efficiency.

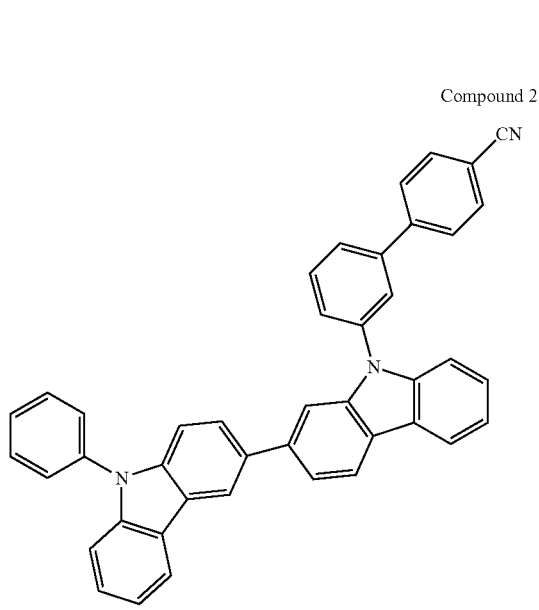 [SMILES: N#Cc1ccc(-c2cccc(-n3c4ccccc4c4ccc(-c5ccc6c(c5)c5ccccc5n6-c5ccccc5)cc43)c2)cc1]

Compound 2

Figure 4:
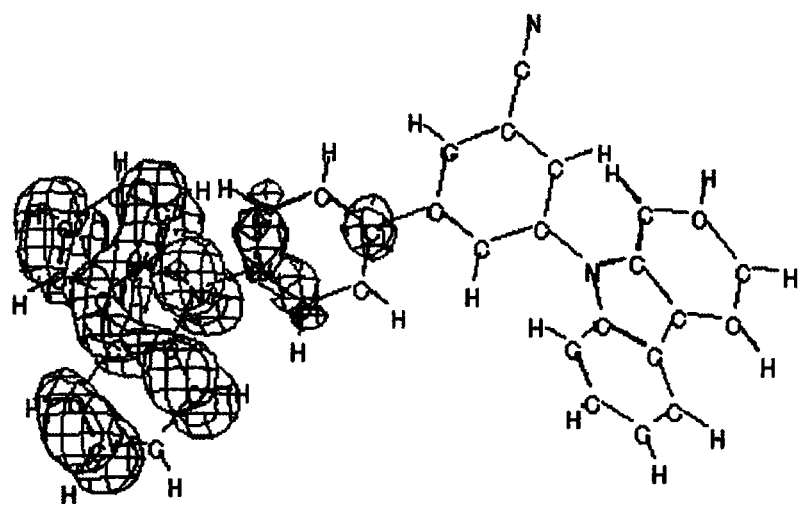
FIG. 4 is a diagram showing the result of molecular orbital calculation of HOMO and LUMO of the compound a described in Patent Document 2.
Figure 4:
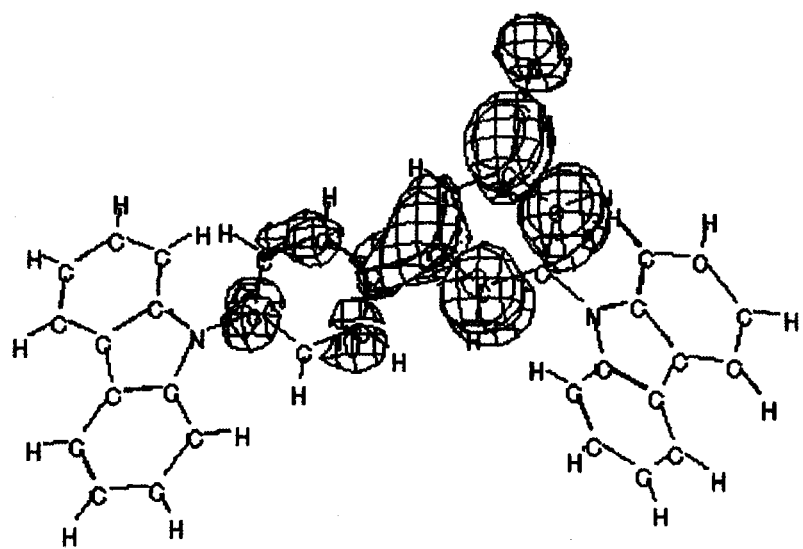

In contrast, in case of the compound a described in Patent Document 2 wherein a cyano group-containing group is introduced between two carbazolyl groups, HOMO is deviated toward one of the carbazolyl groups as shown in FIG. 4, to narrow the distribution of the electron cloud of HOMO. The narrow distribution of electron cloud may cause a drastic reduction in the injecting/transporting ability. In addition, the distribution of LUMO overlaps the distribution of HOMO on the phenylene group. Unlike the material for organic EL device of the invention, the distributions of HOMO and LUMO which are not separated may result in poor carrier balance in the molecule.

The molecular orbital distributions shown in FIGS. 2 to 4 were calculated by using Gaussian 98 at a level of TDDTF B3LYP/6-31G* opt. The results shown in FIGS. 2 to 4 are only for explaining the properties of the material for organic EL device of the invention and should not be construed to limit the scope of the invention.

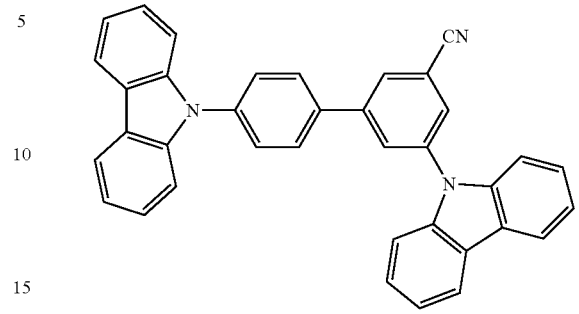

Compound a

In an organic EL device, for example, which employs the material for organic EL device represented by formula (I) as a host material of a phosphorescent light emitting layer, the compound represented by formula (I) having a hole injecting/transporting unit will increase the amount of holes in the light emitting layer as compared with using the compound a described in Patent Document 2. In addition, the cyano group-containing aromatic hydrocarbon group and the cyano group-containing heterocyclic group which act as an electron injecting/transporting unit tend to be highly resistant to holes as compared with a nitrogen-containing heterocyclic compound, such as pyrimidine ring and triazine ring, which has been known as an electron injecting/transporting material. The long lifetime of the organic EL device employing the material for organic EL device of the invention is attributable to this high resistance to holes.

The production method of the derivative of the invention is not particularly limited and it is produced according to a known method, for example, by a coupling reaction of a carbazole derivative and an aromatic halogenated compound in the presence of a copper catalyst described in Tetrahedron 40 (1984) 1435 to 1456 or a palladium catalyst described in Journal of American Chemical Society 123 (2001) 7727 to 7729.

Specific examples of the material for organic EL device of the invention are shown below, although not limited thereto.

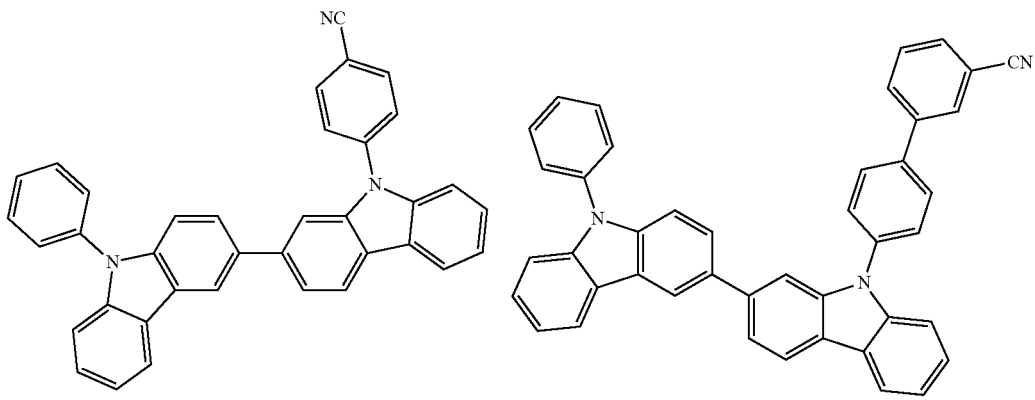

-continued
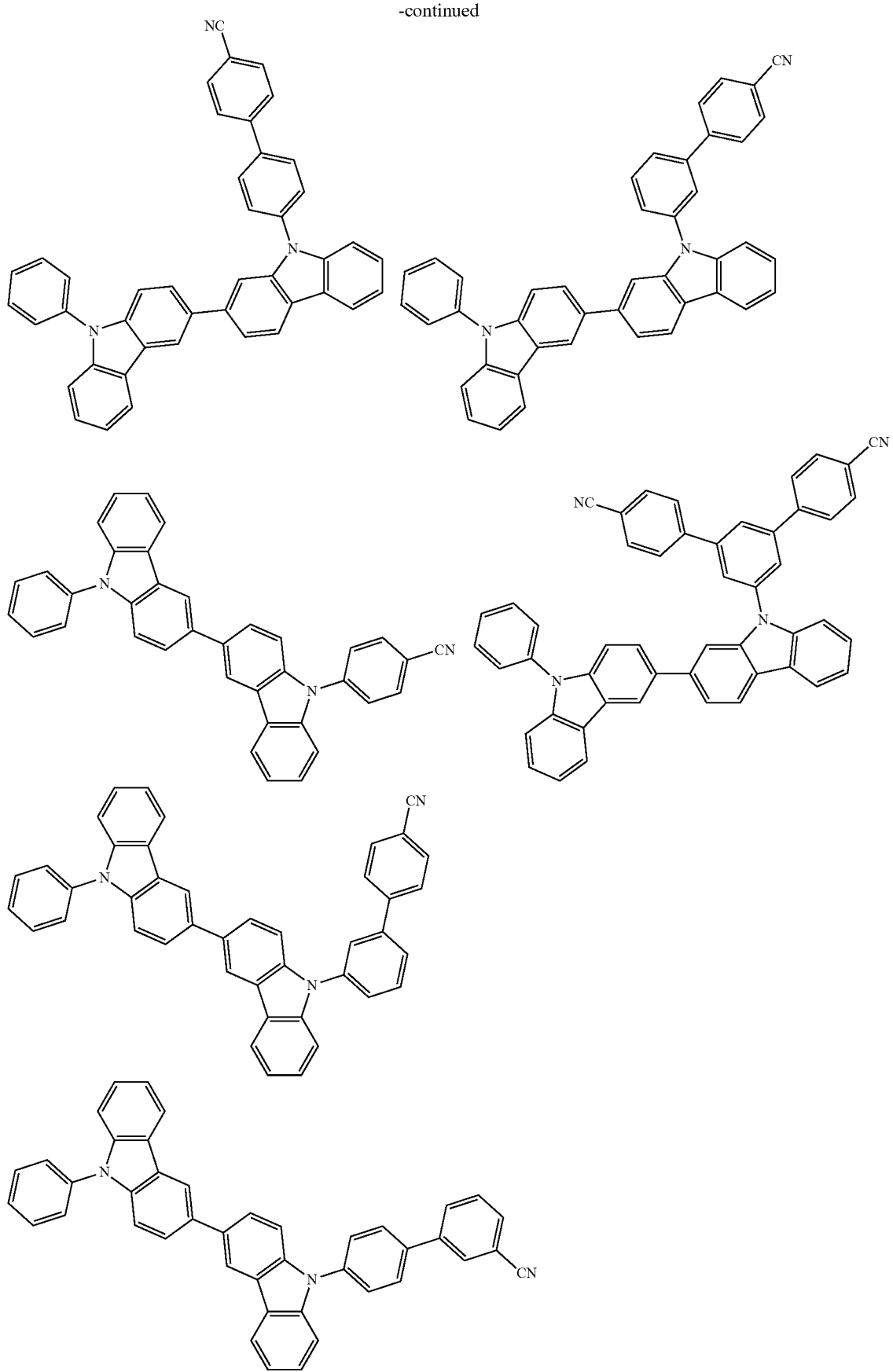

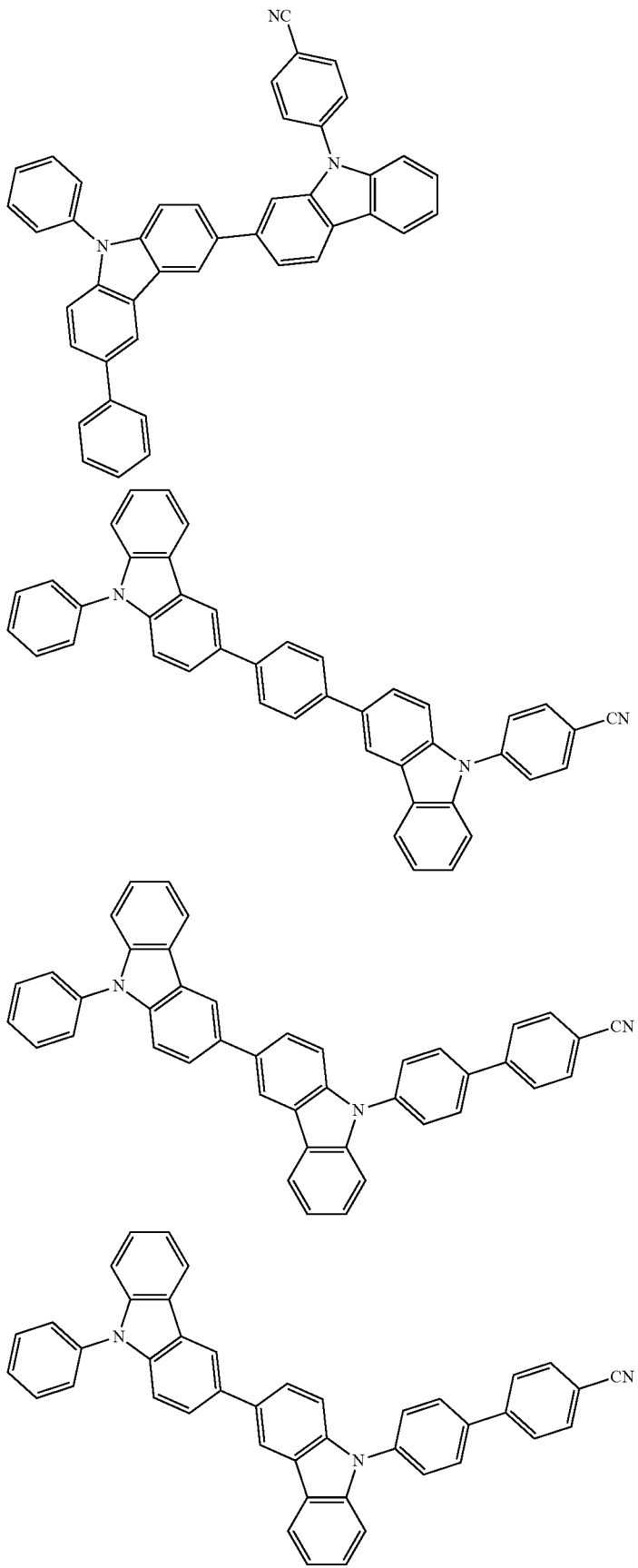

-continued
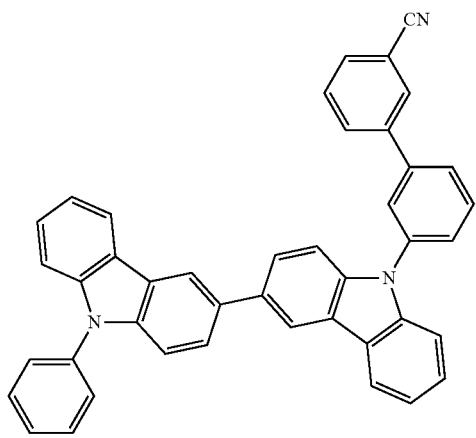
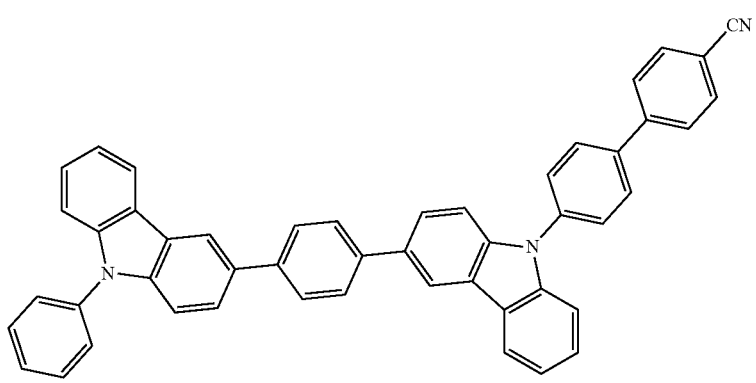
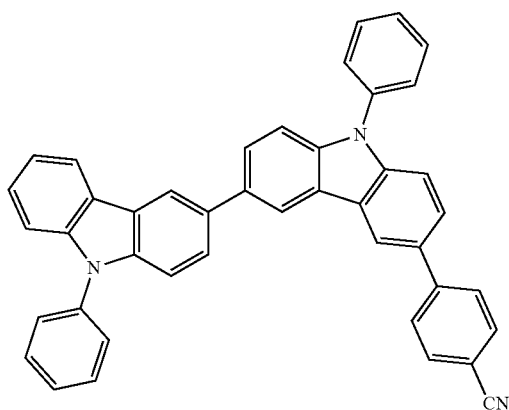
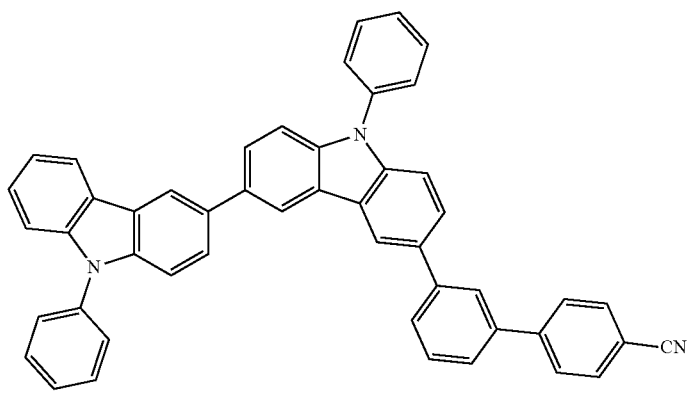

-continued
21
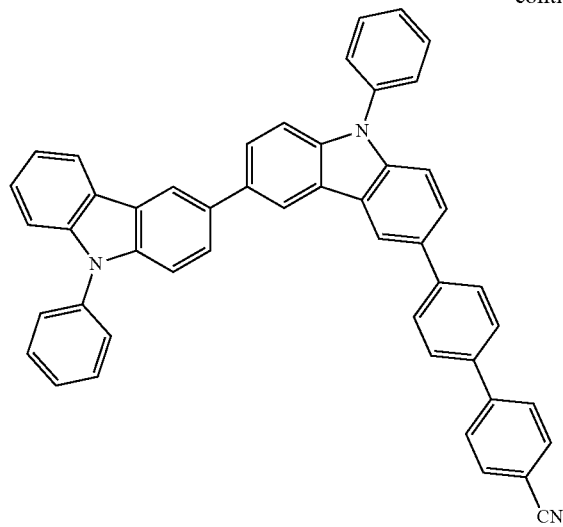
22
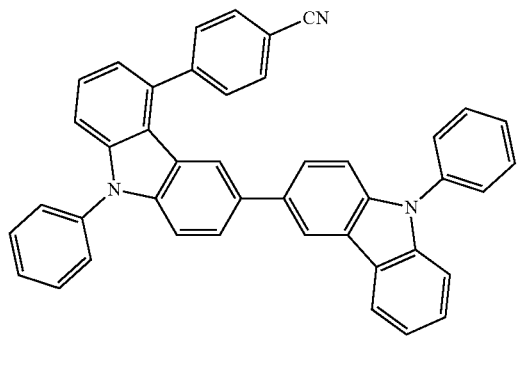
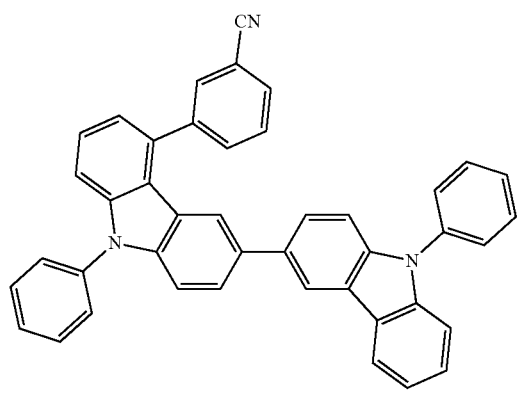
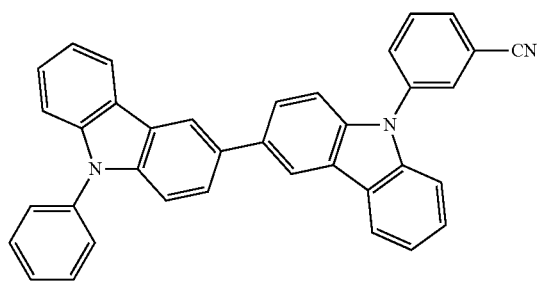
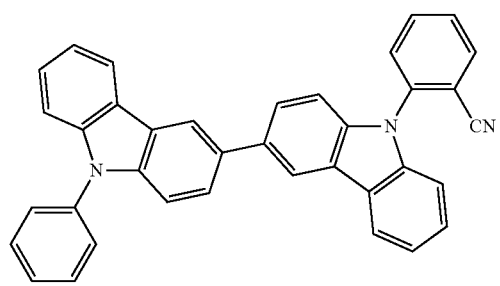
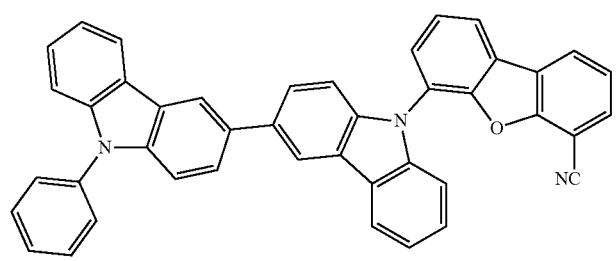
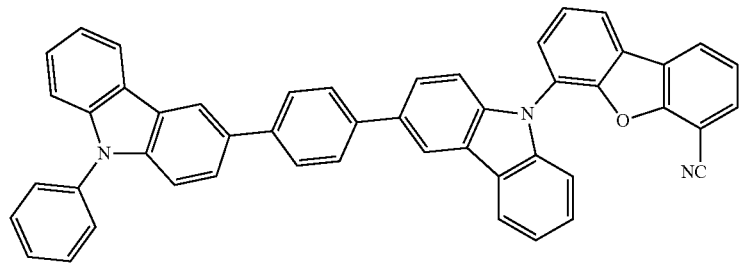

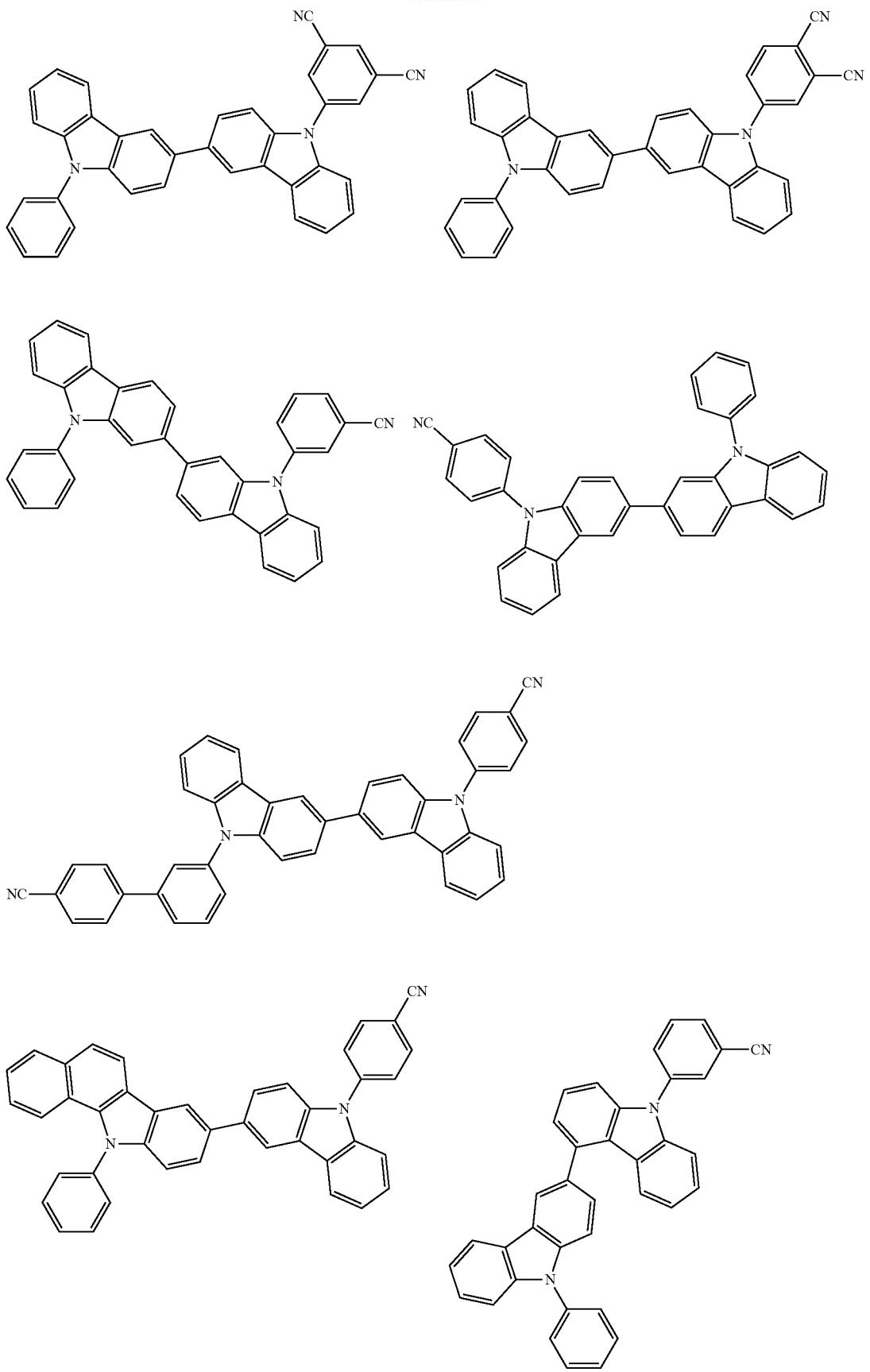

-continued
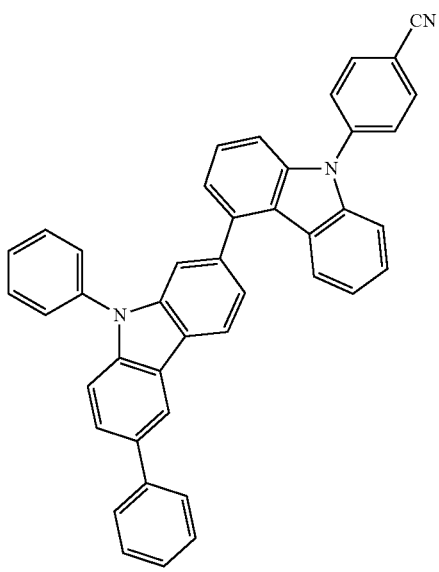
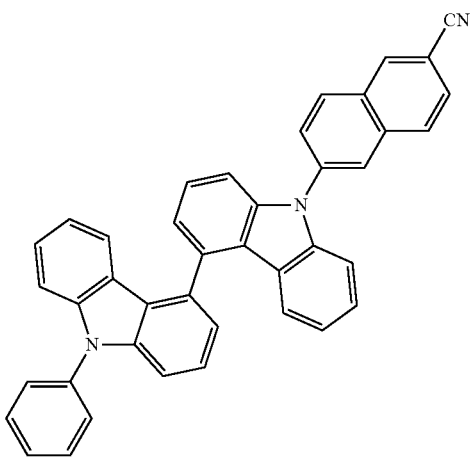
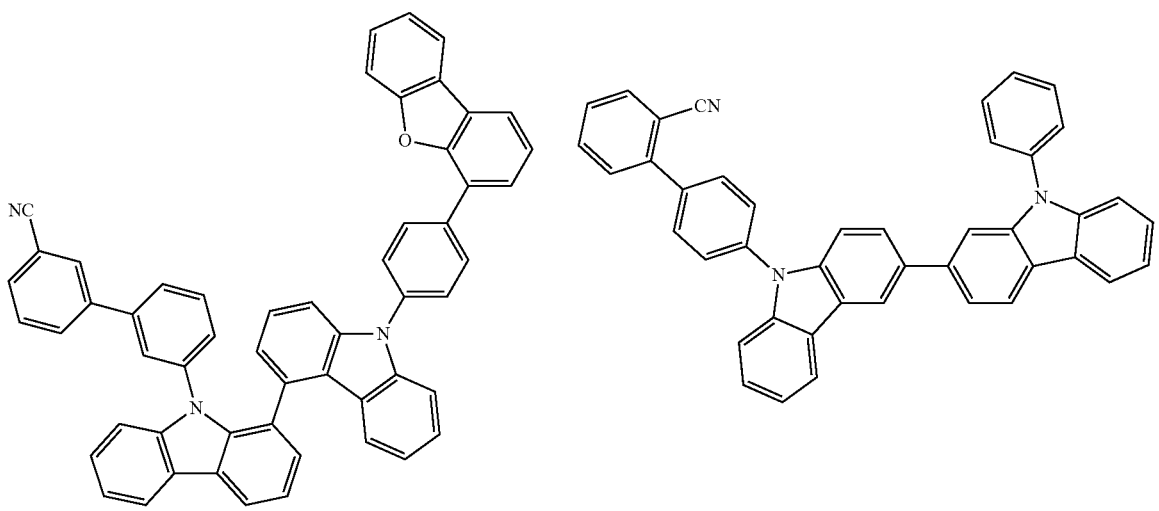
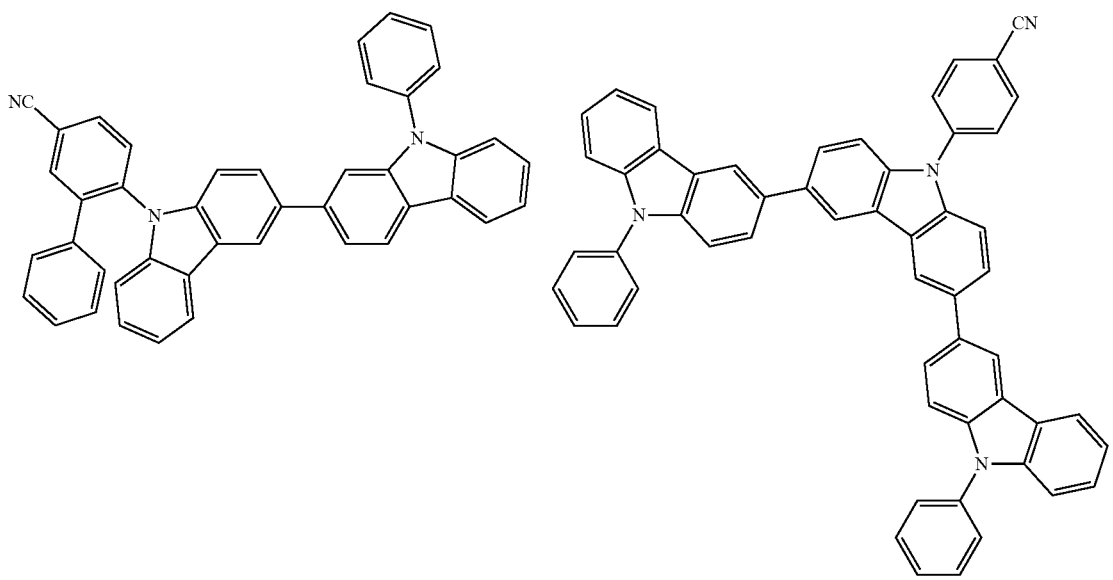

-continued
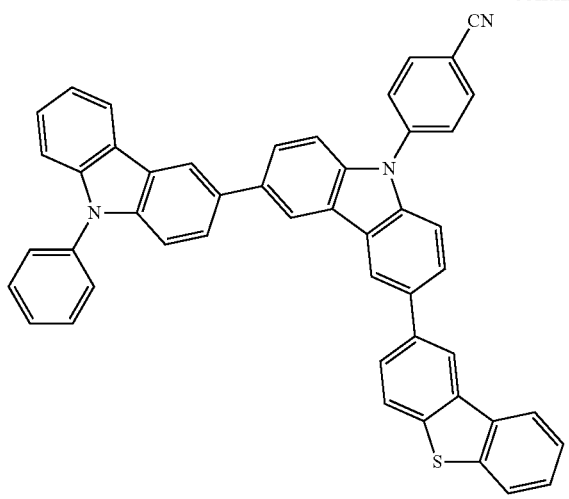
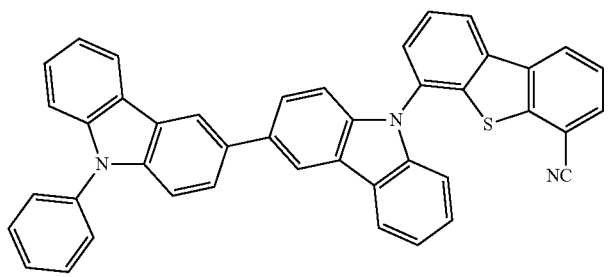
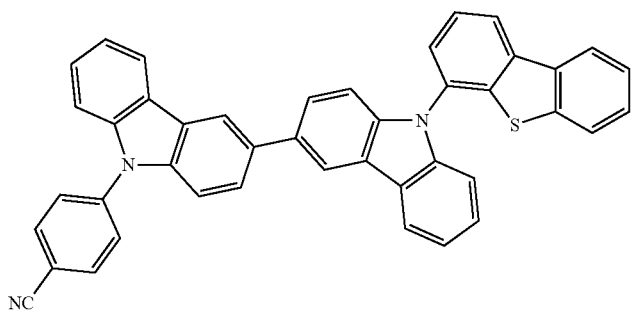
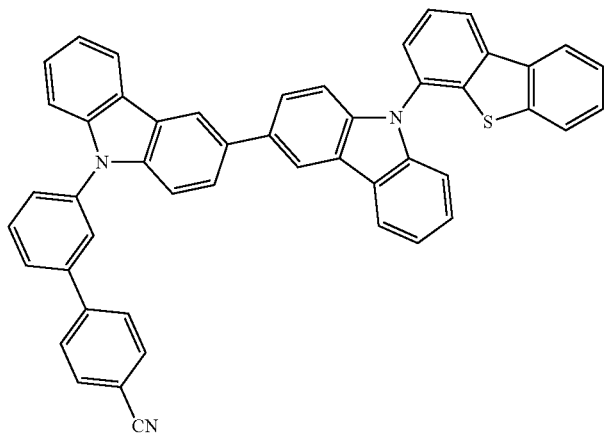

-continued
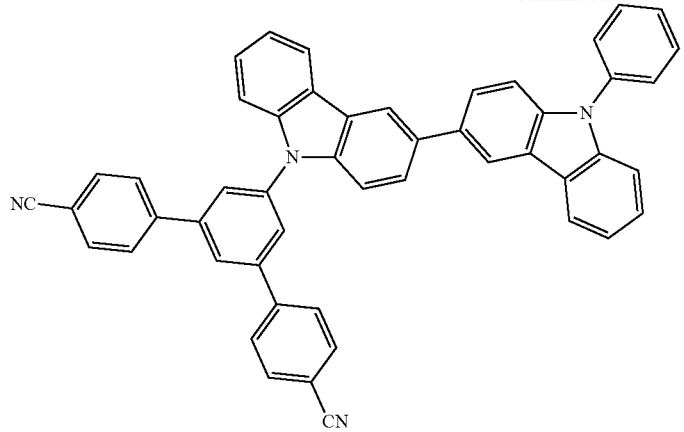
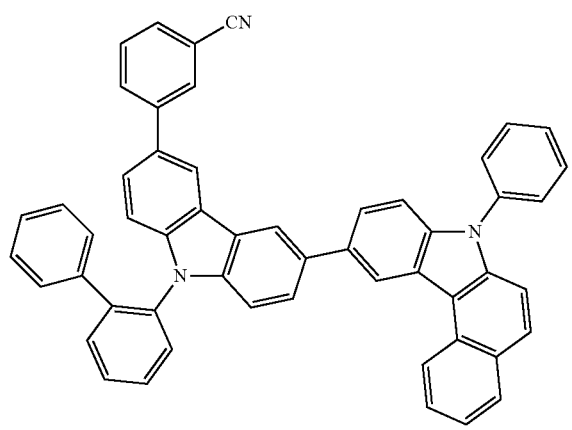
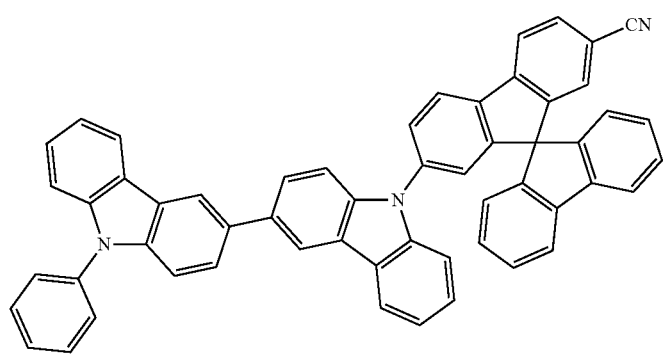
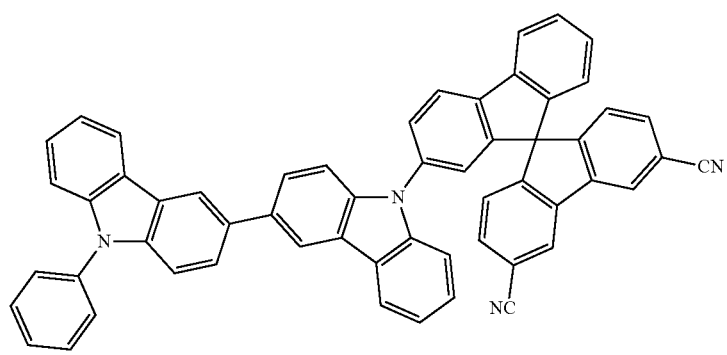

-continued
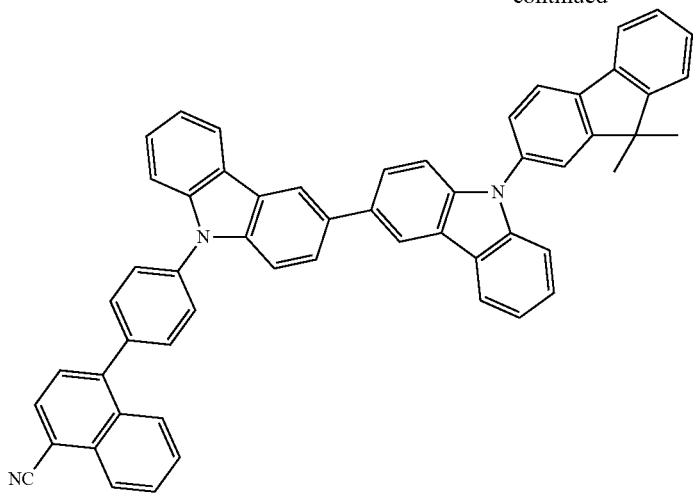
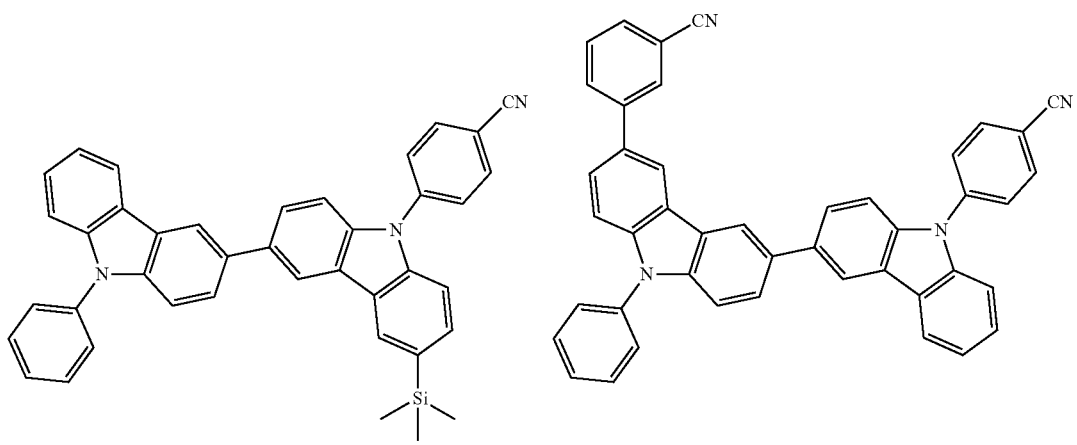
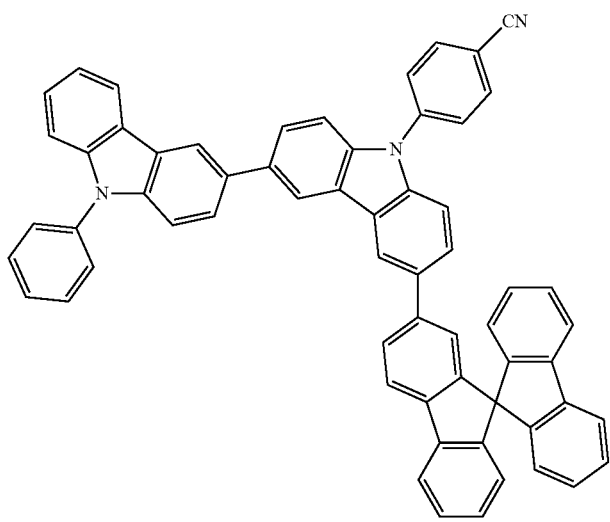

-continued
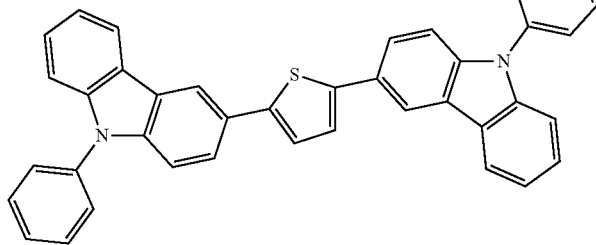
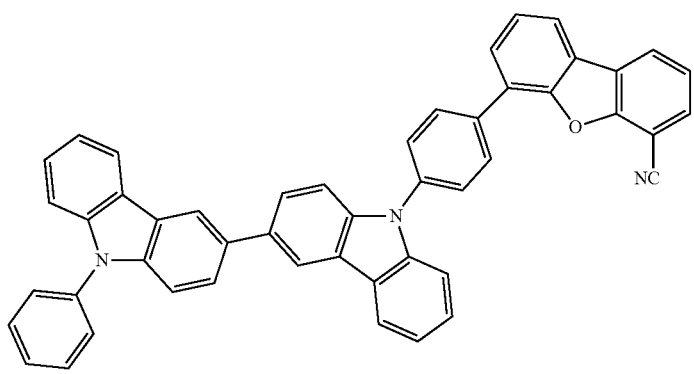
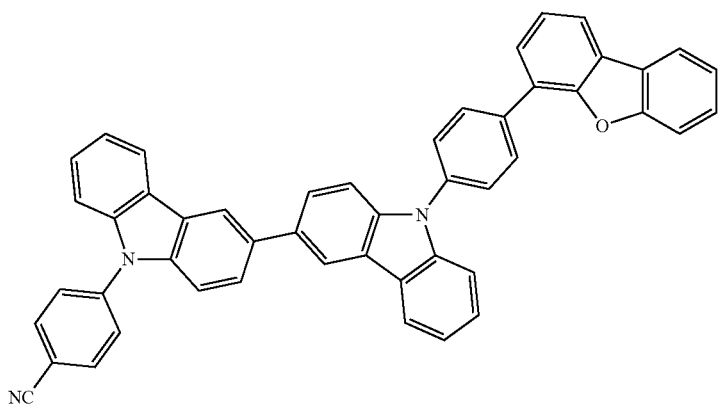
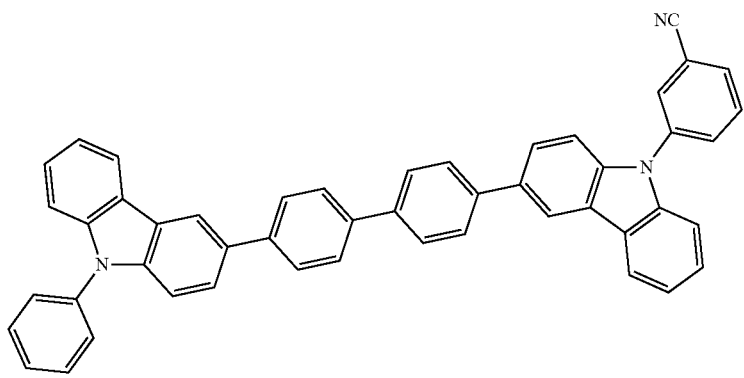

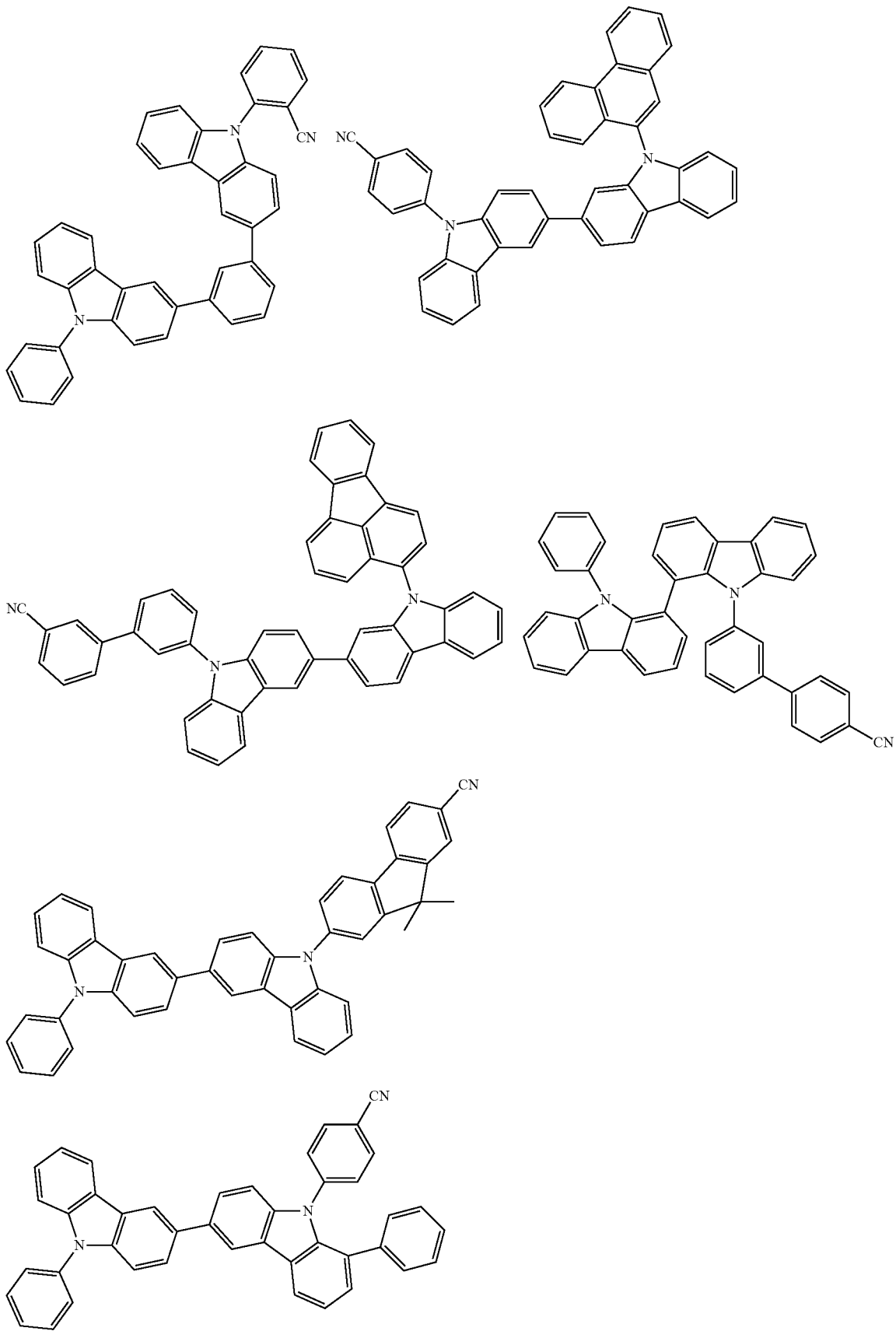

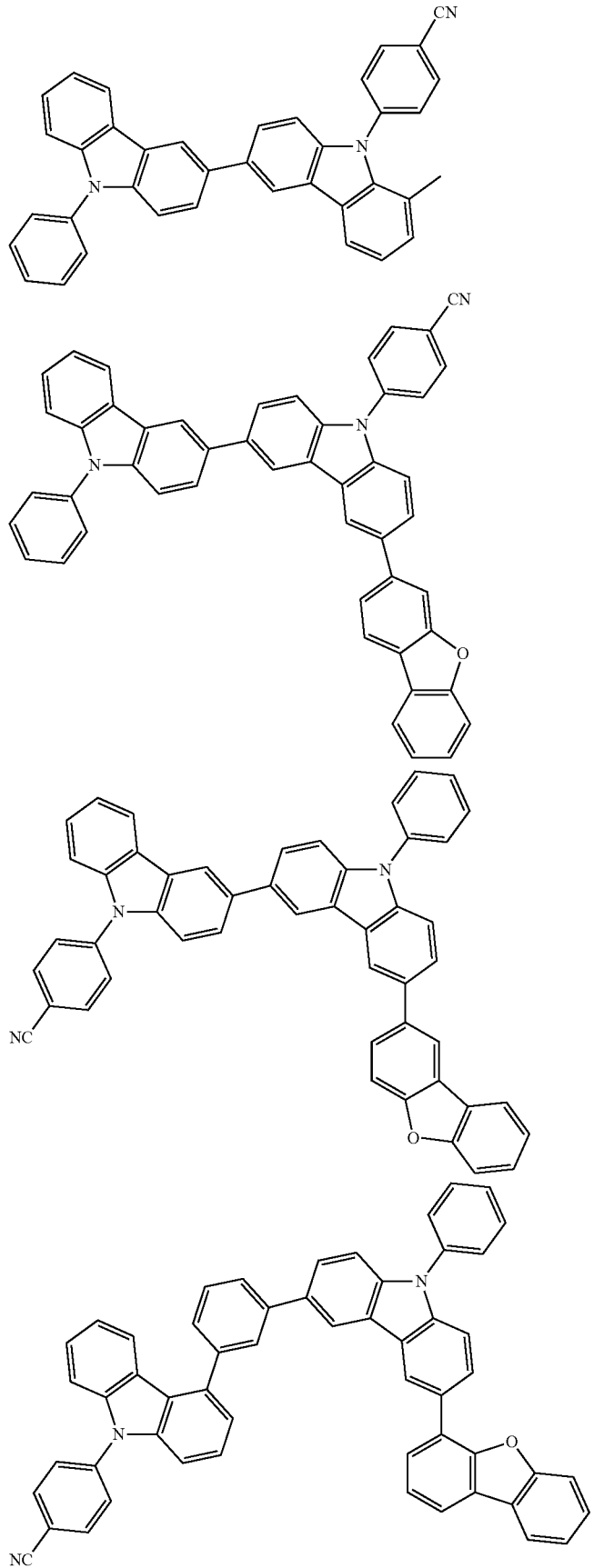

-continued
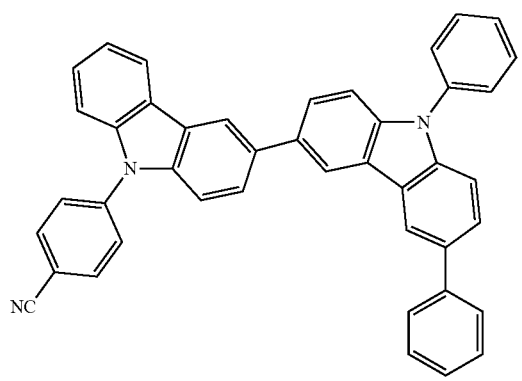
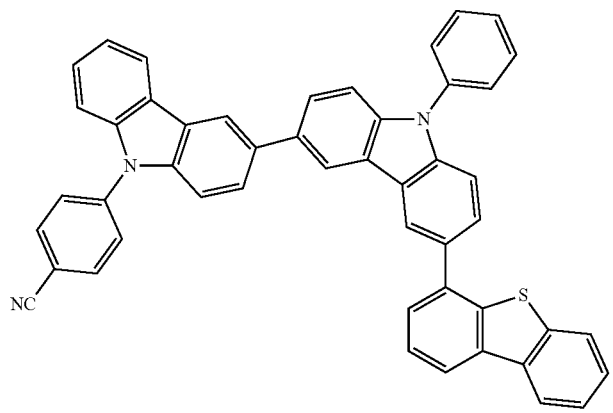
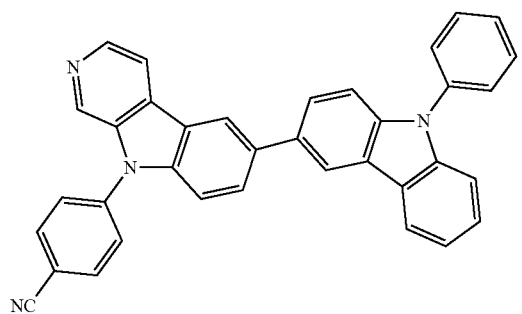
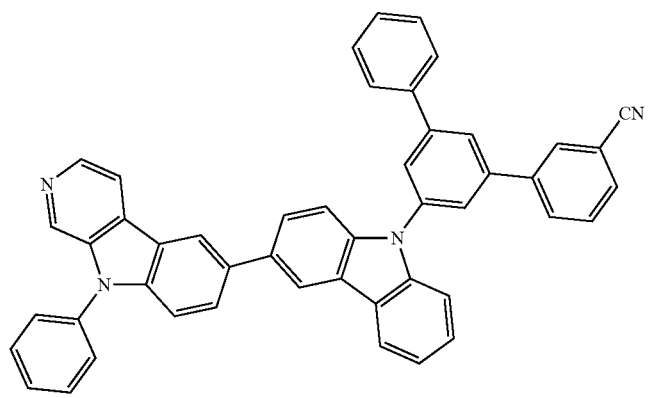

-continued
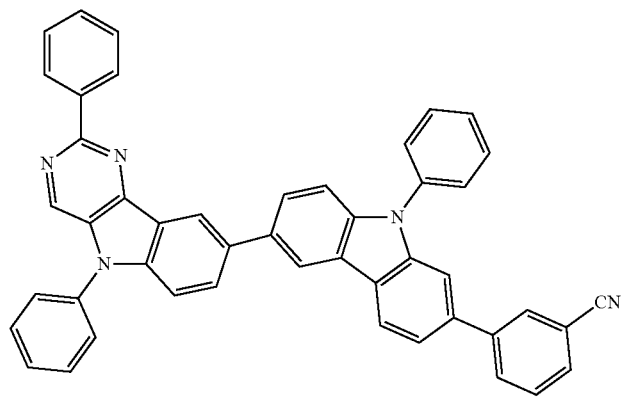
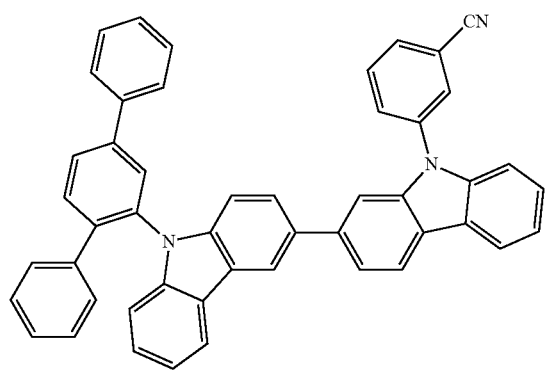
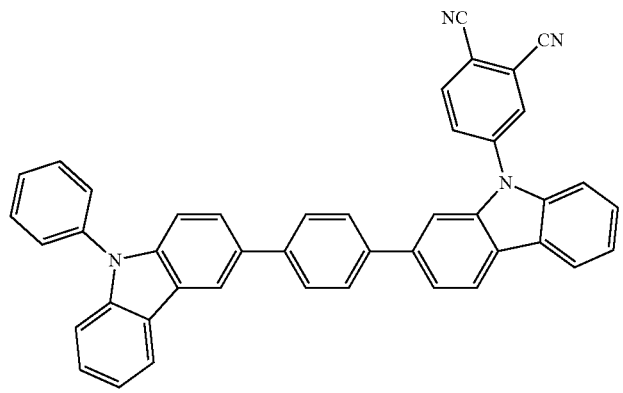
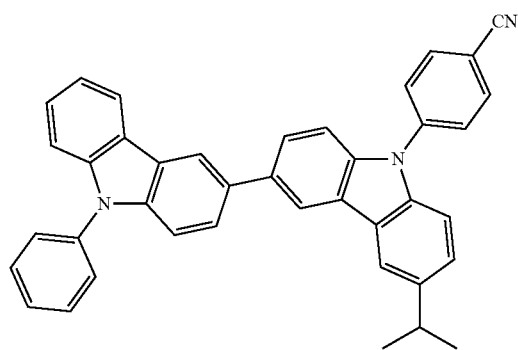

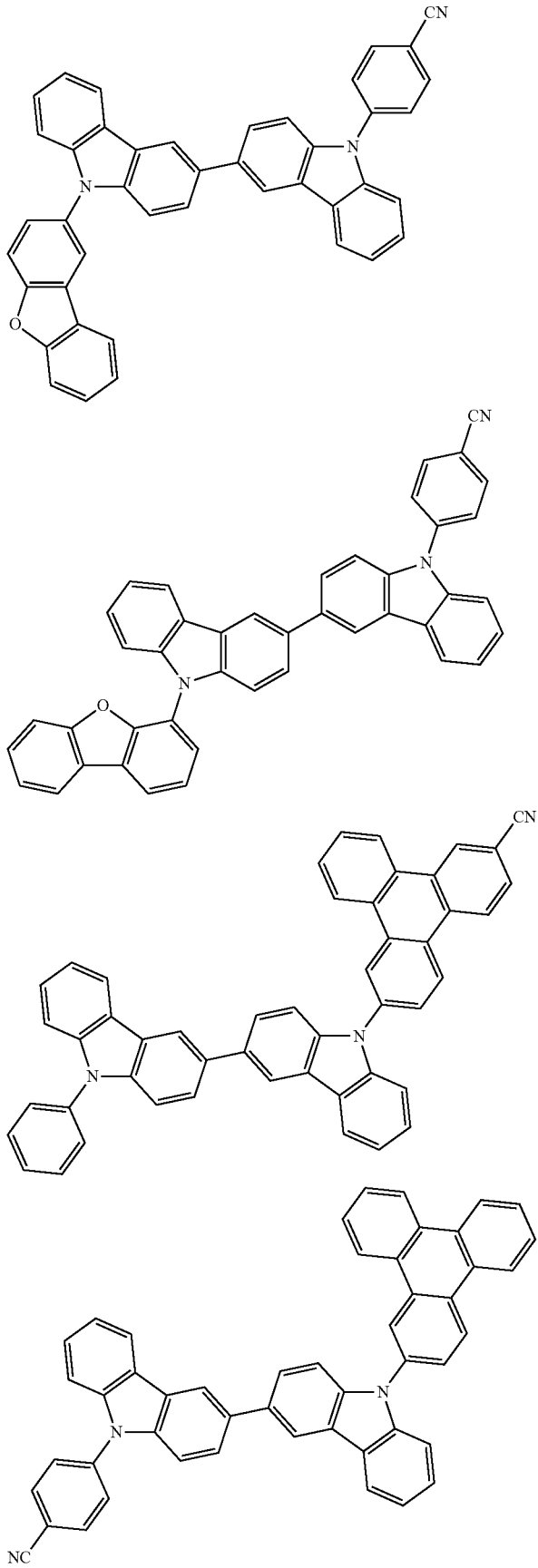

-continued
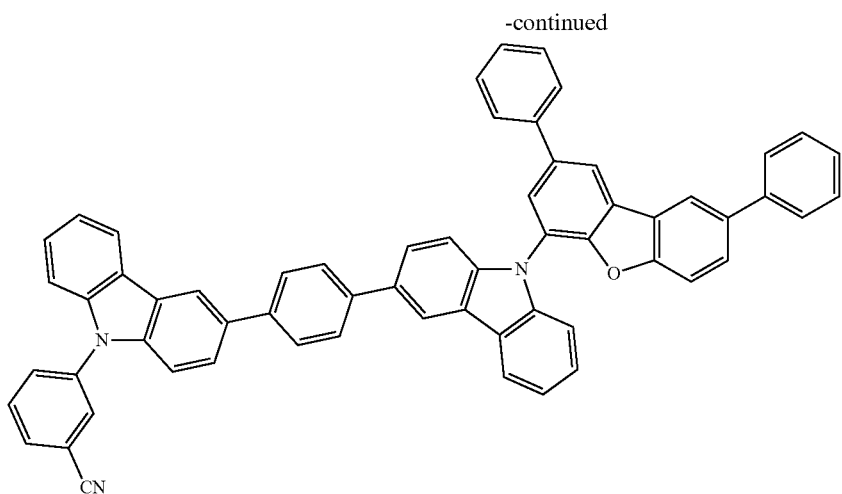
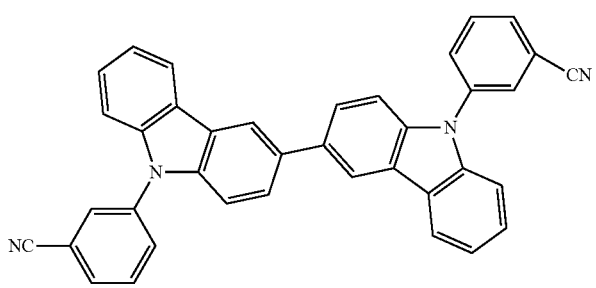
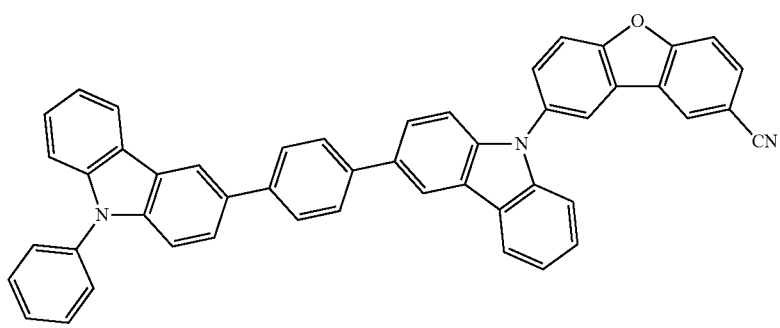
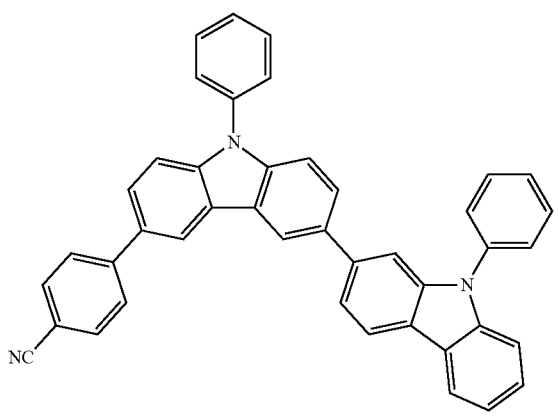

-continued
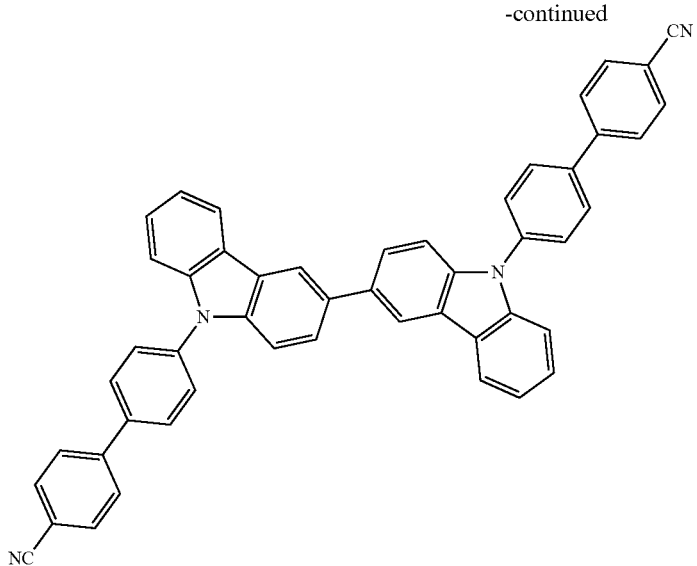
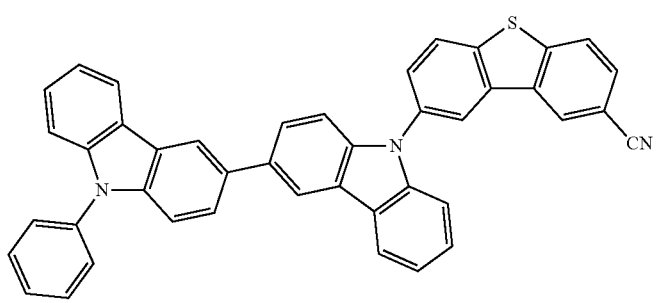
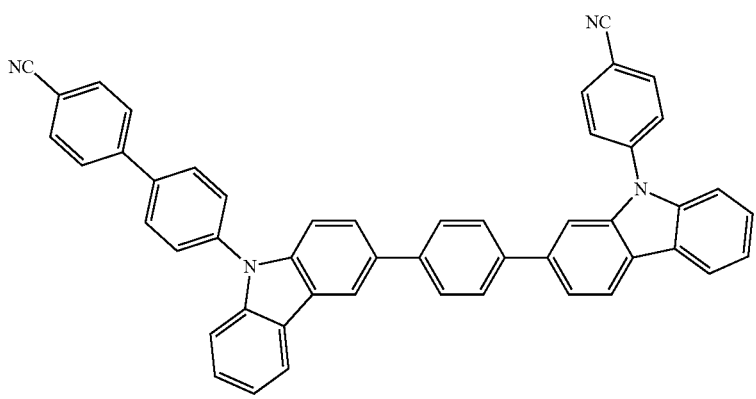
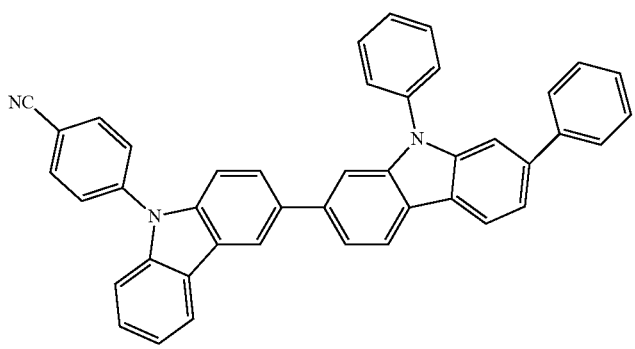

-continued
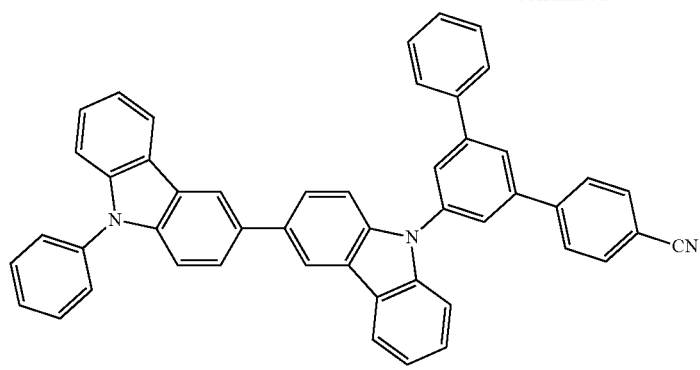
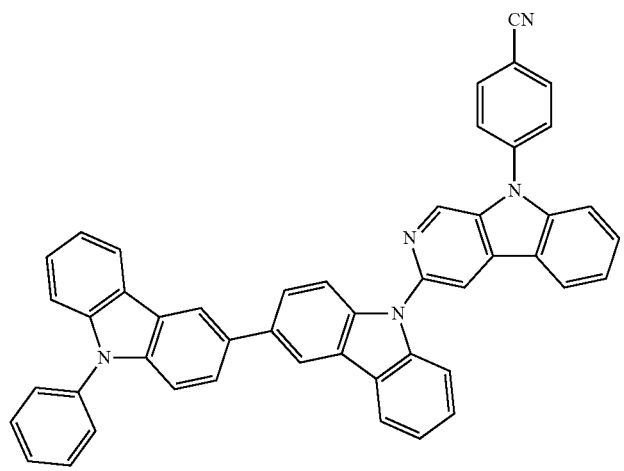
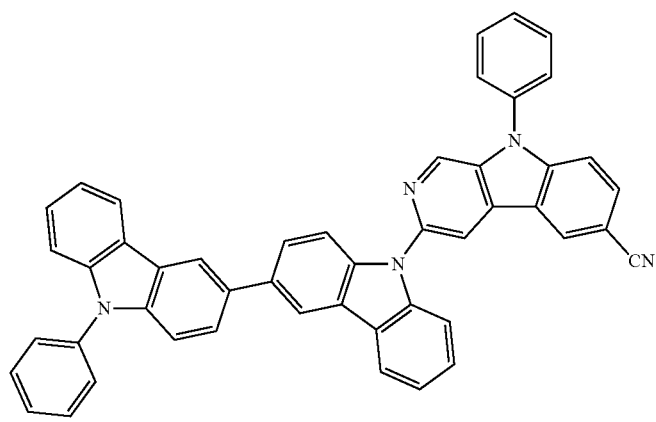
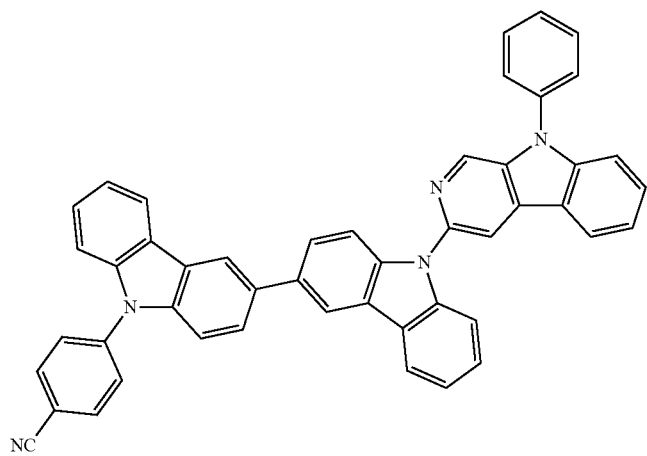

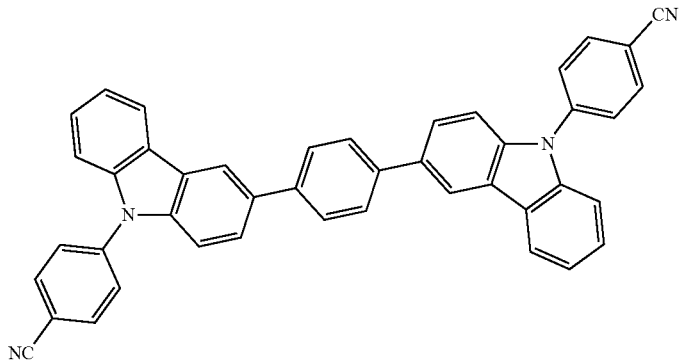
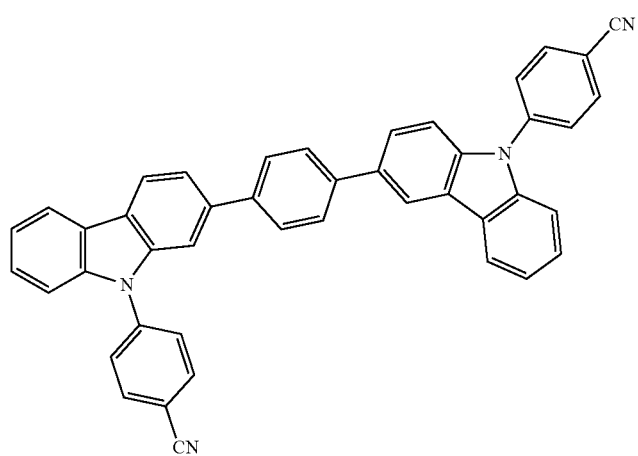
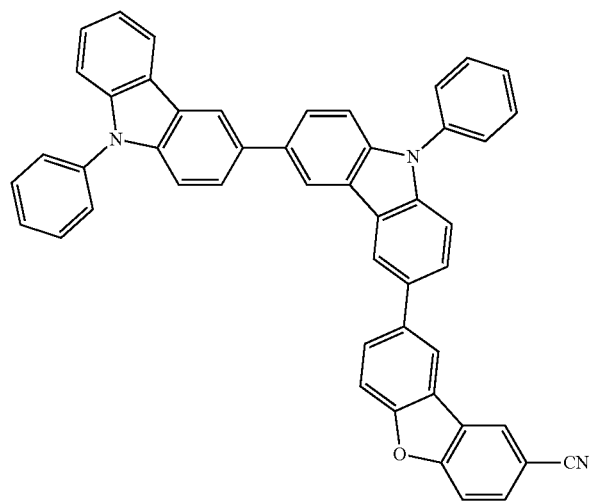

-continued
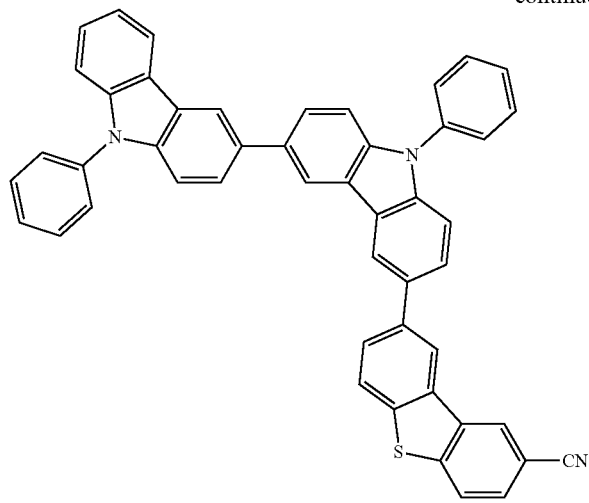
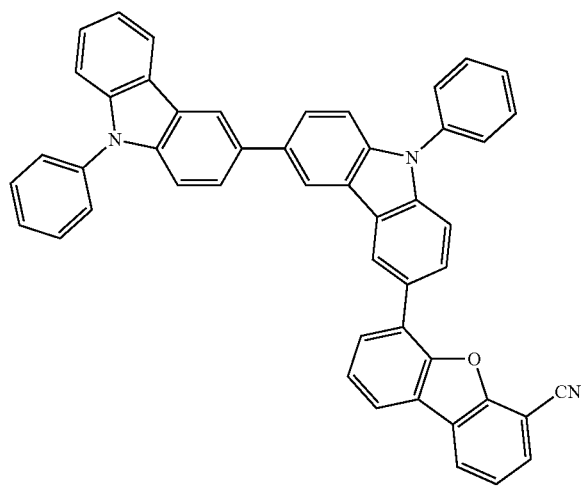 [SMILES: N#Cc1cccc2c1oc1c(-c3ccc4c(c3)c3cc(-c5ccc6c(c5)c5ccccc5n6-c5ccccc5)ccc3n4-c3ccccc3)cccc12]
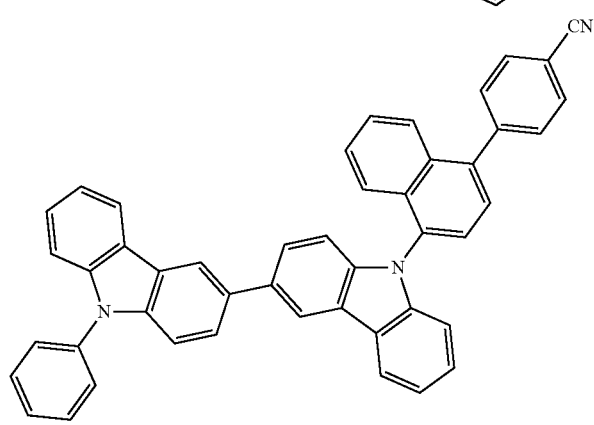
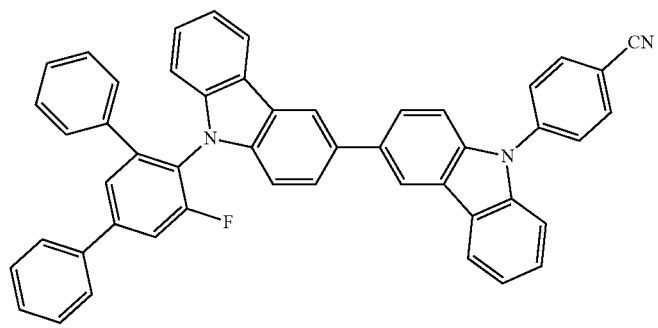

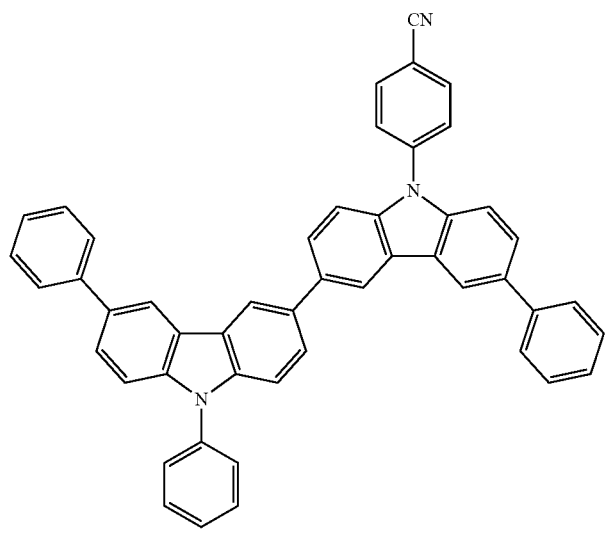
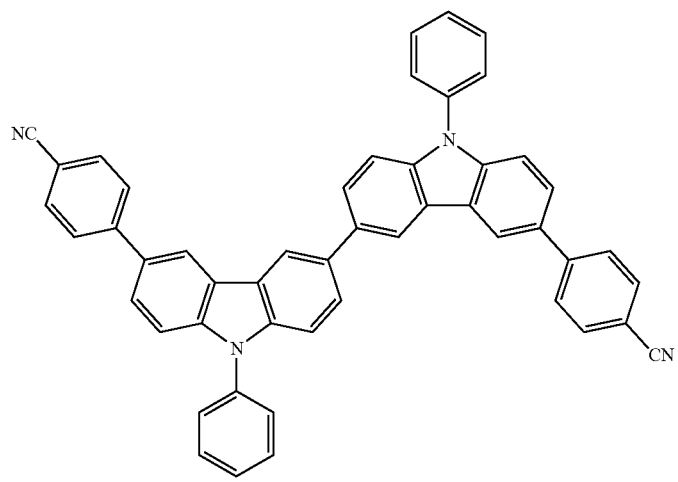
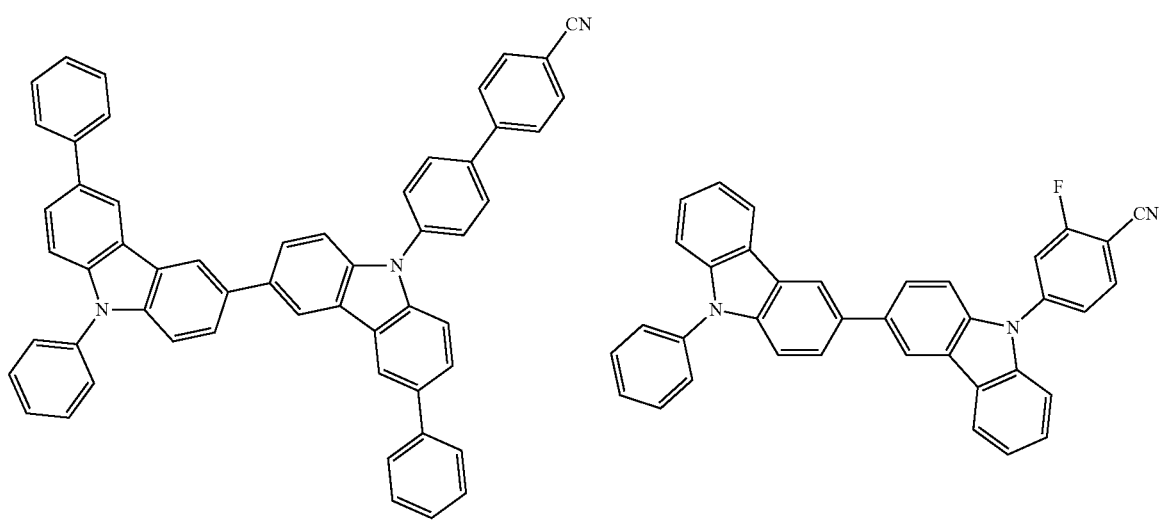

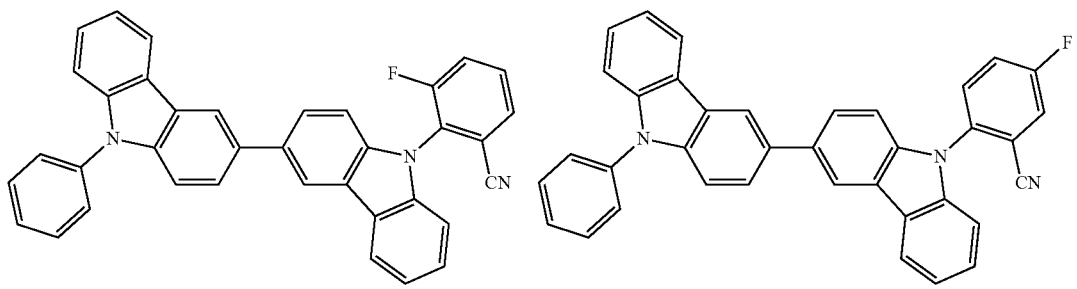
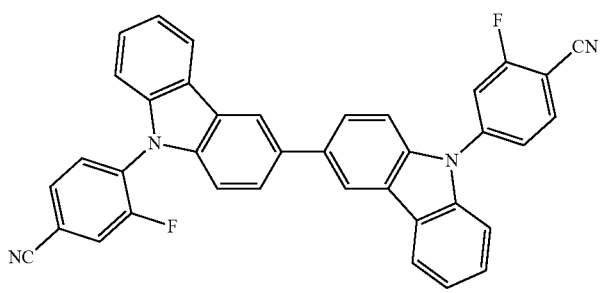
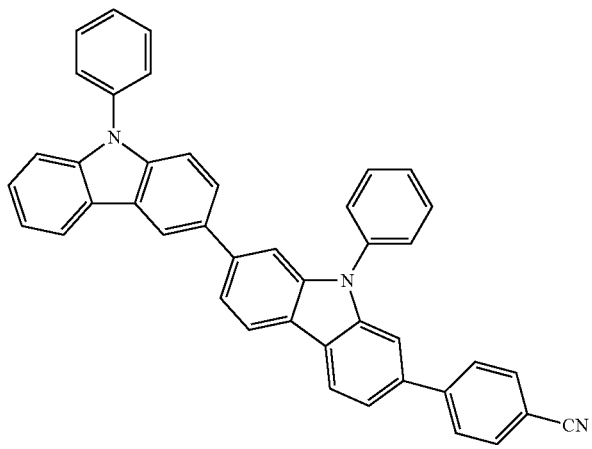
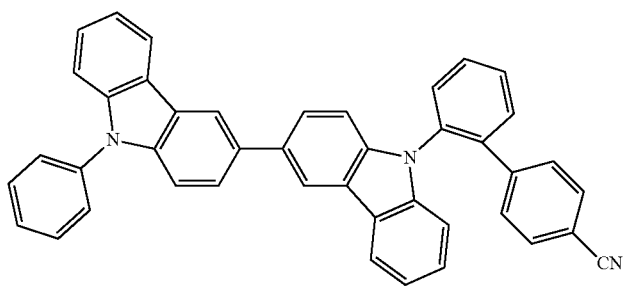

-continued
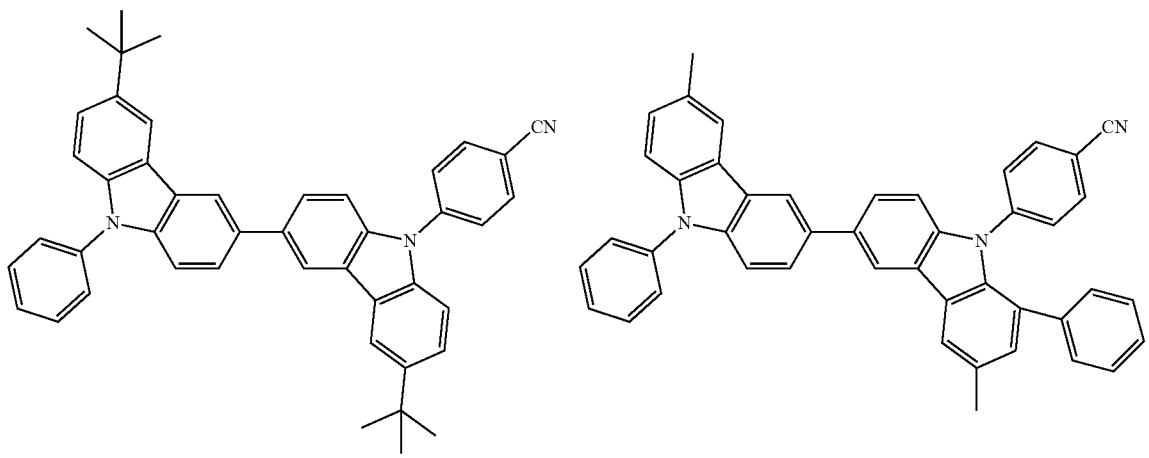
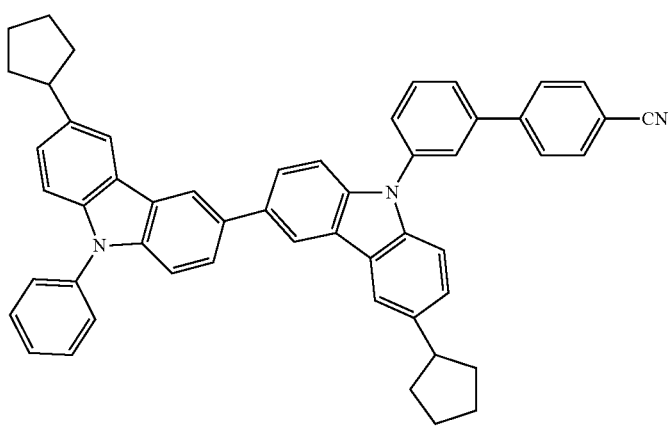
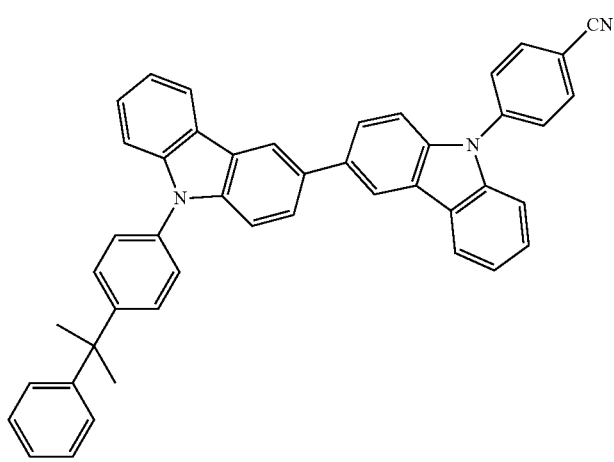
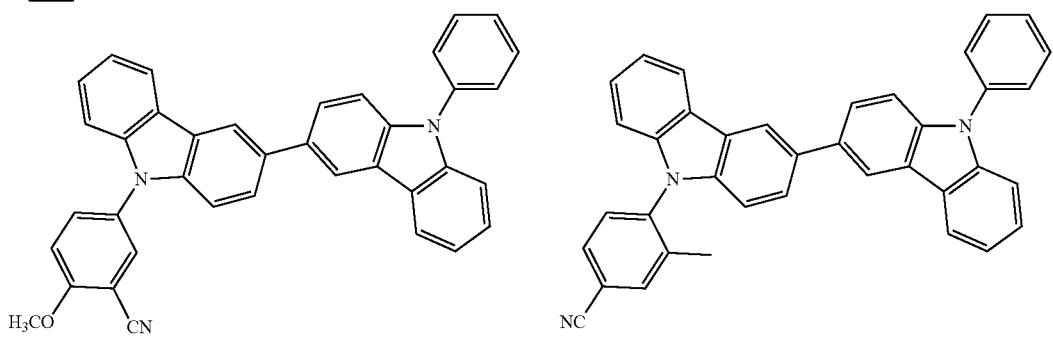

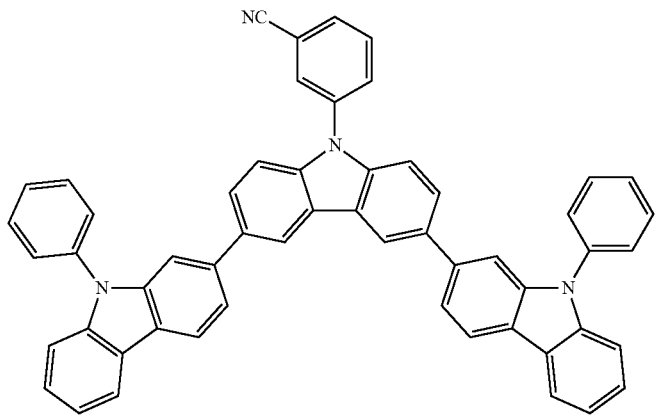
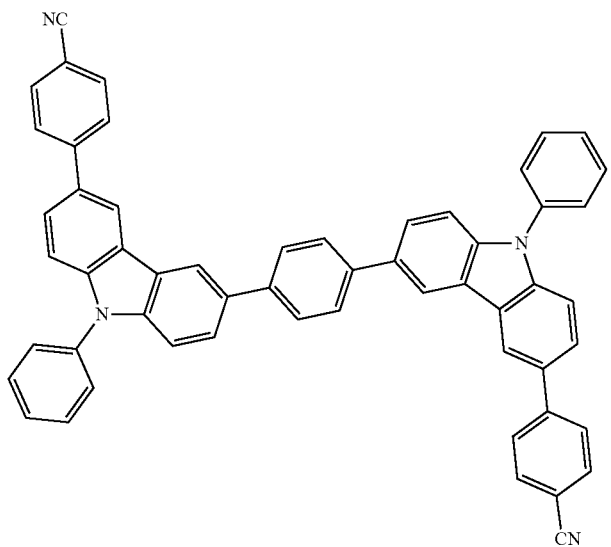
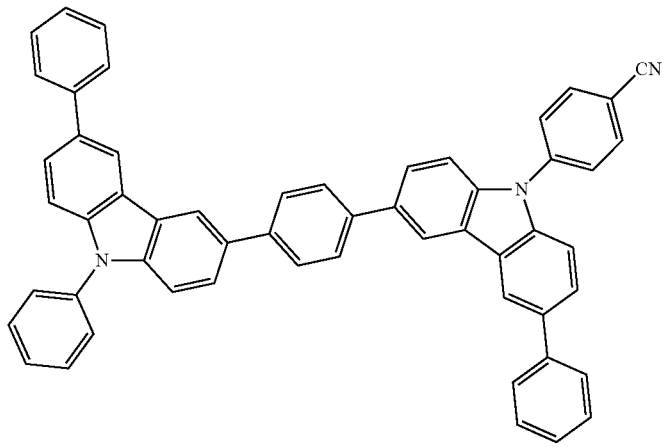

-continued
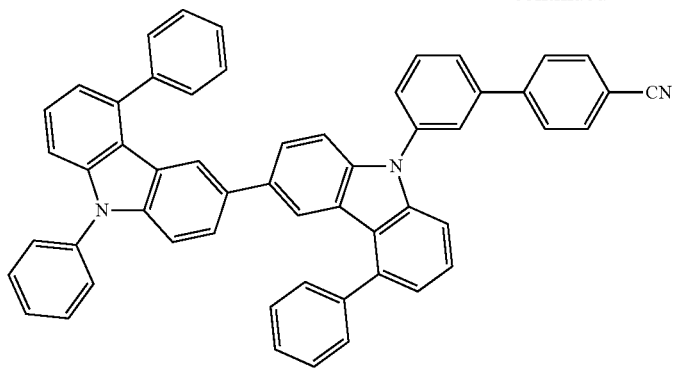
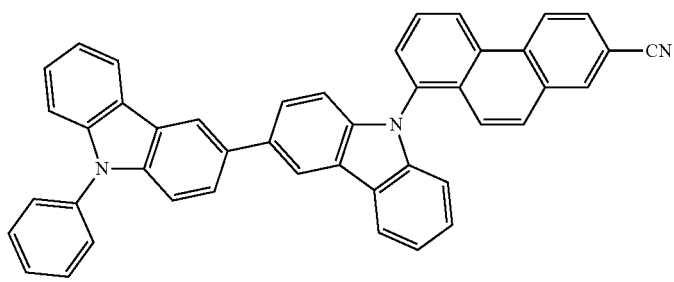
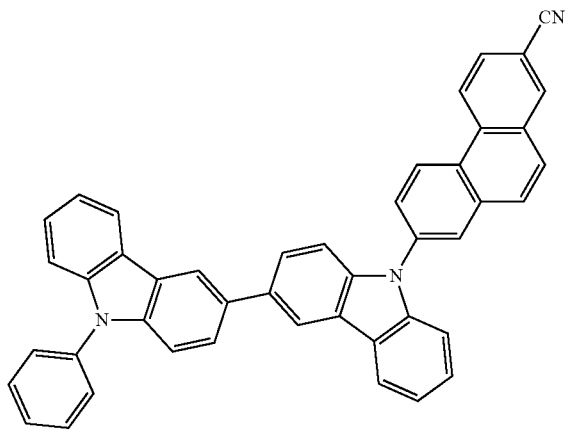
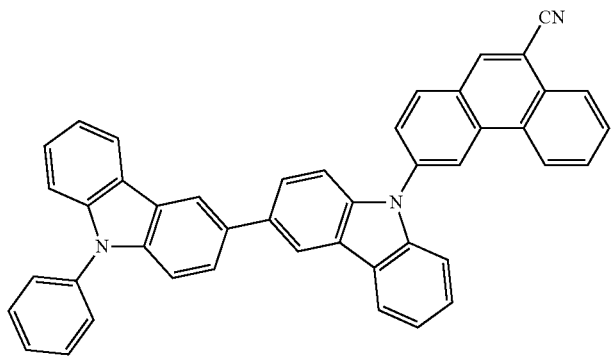

-continued
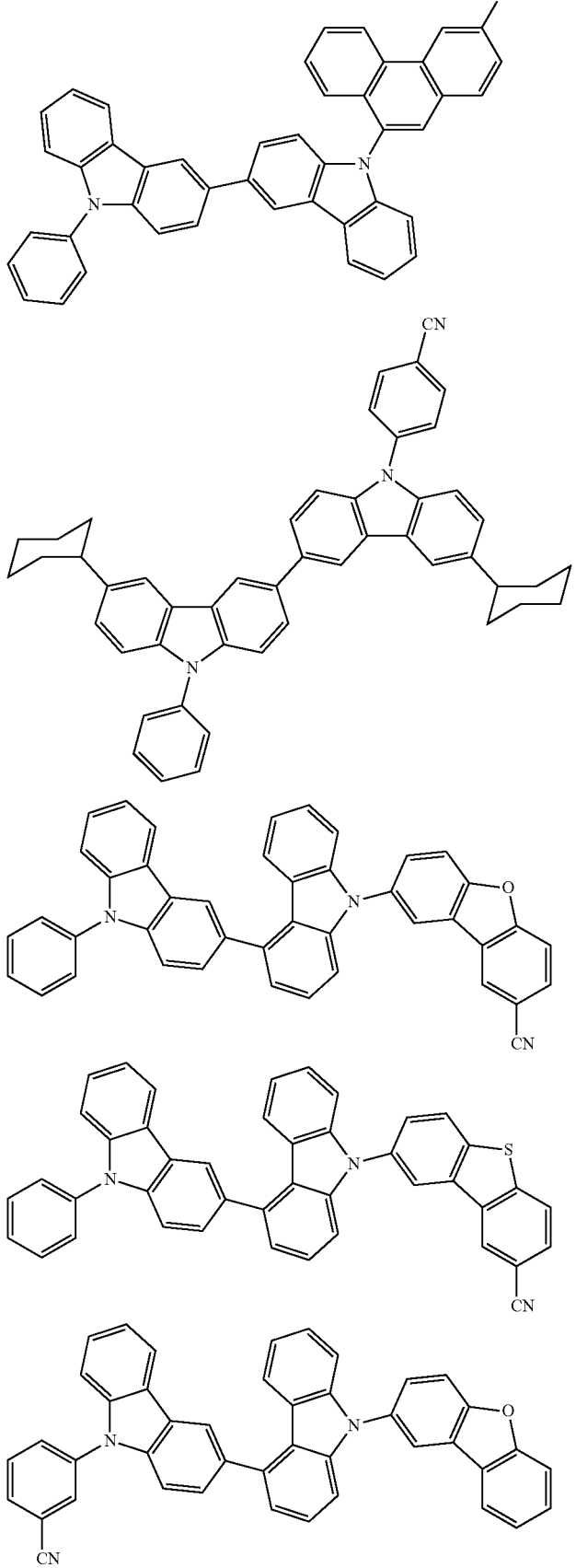

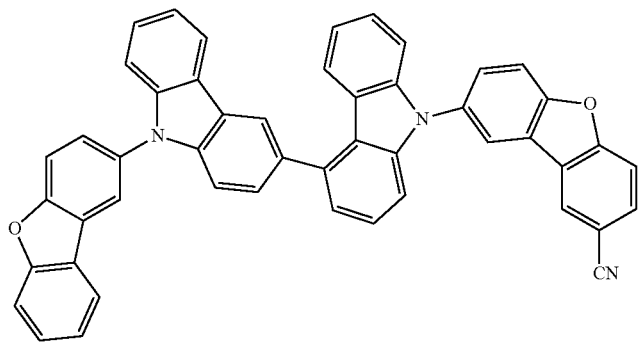
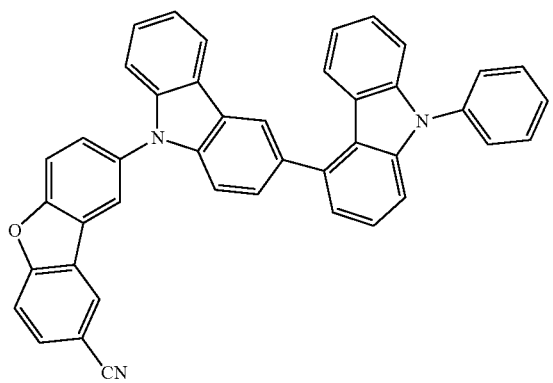
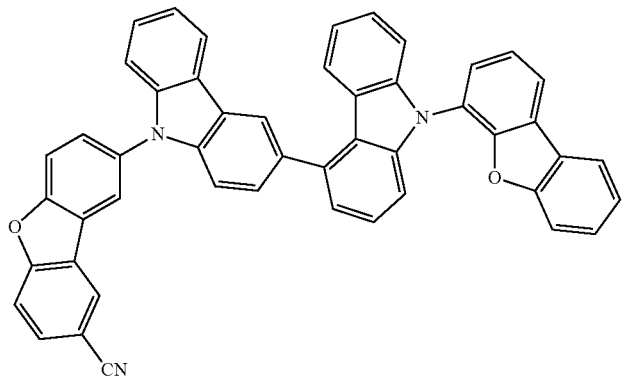
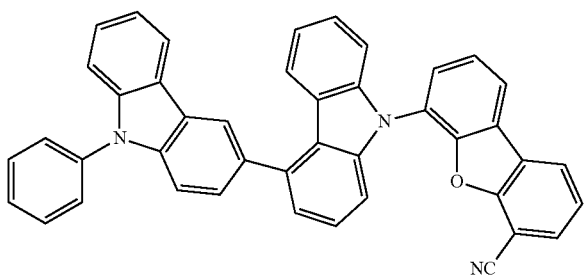

-continued
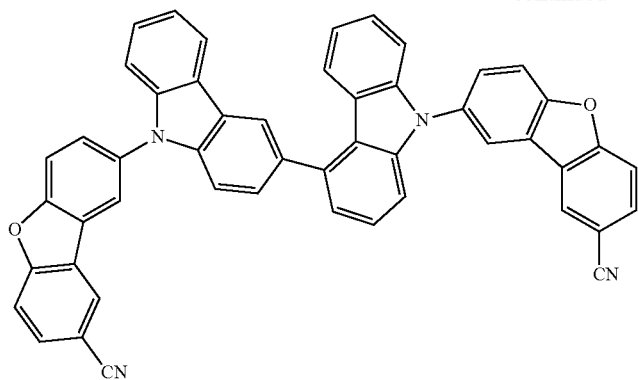
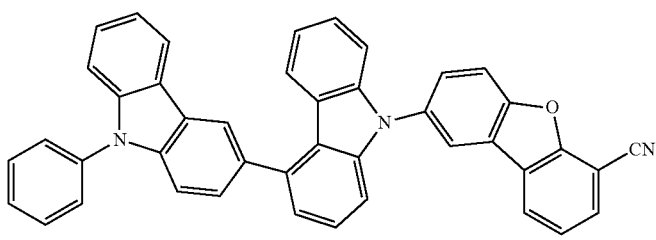
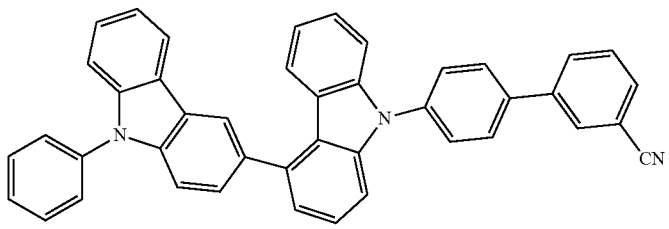
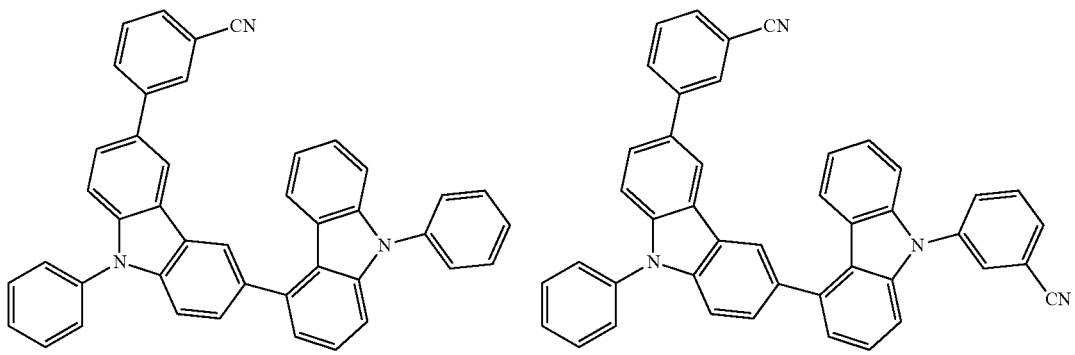
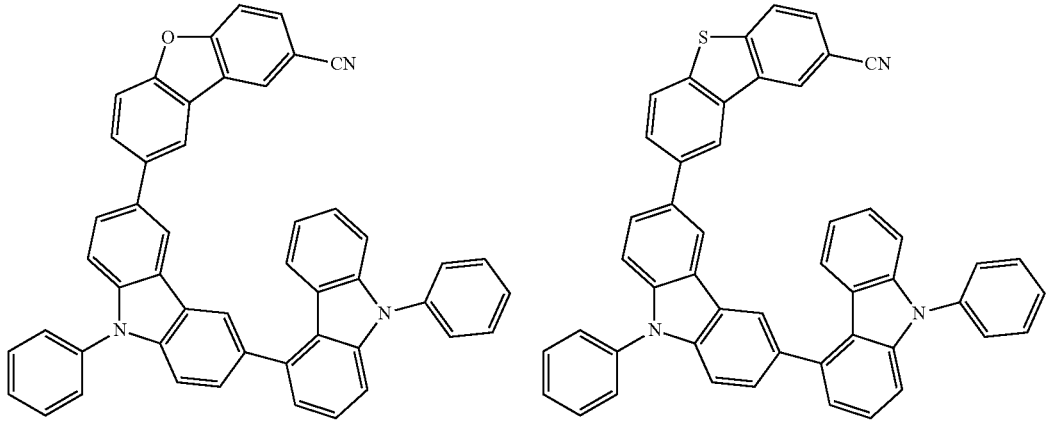

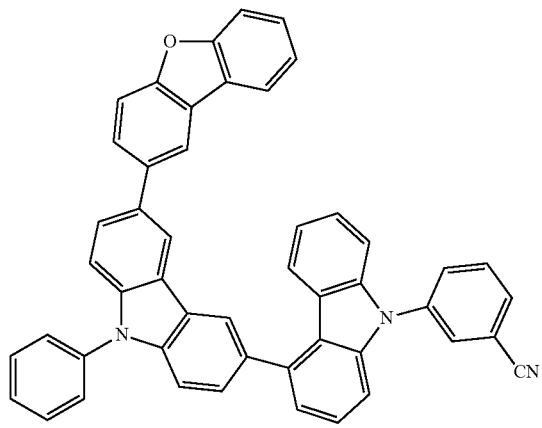
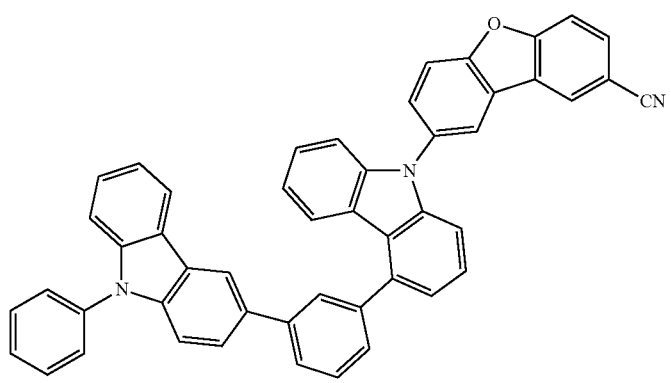
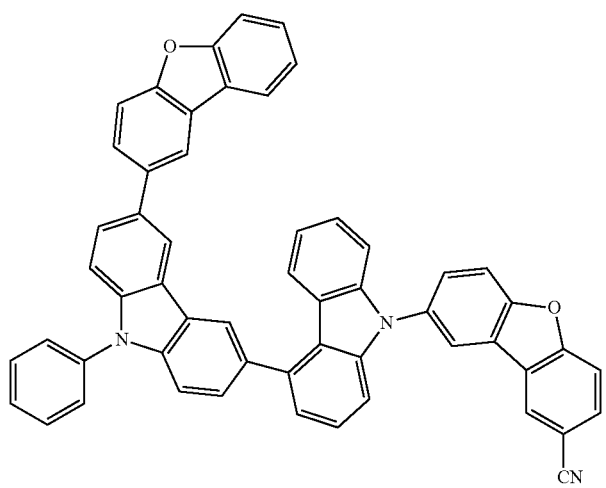

-continued
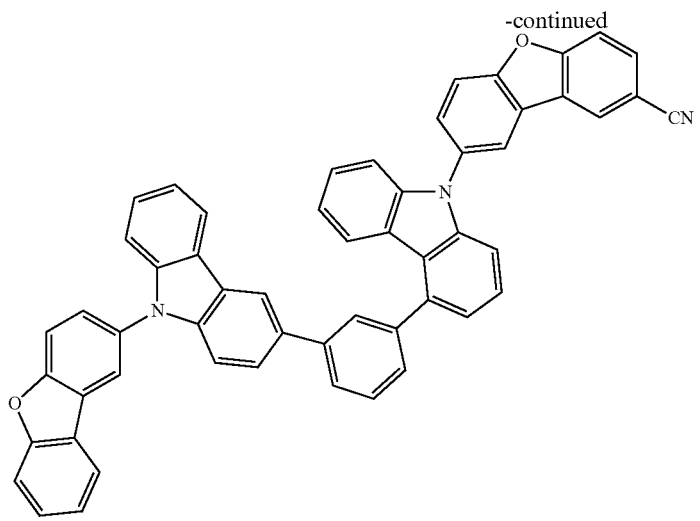
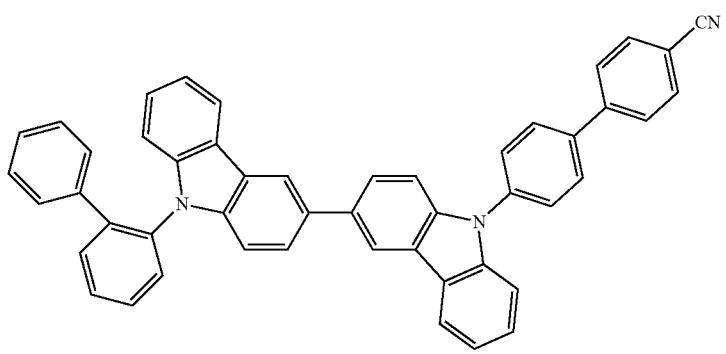
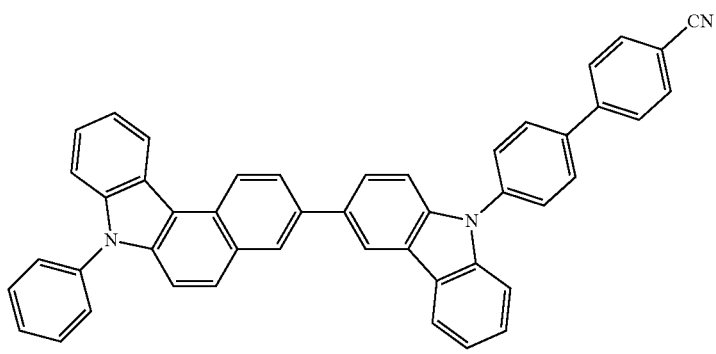
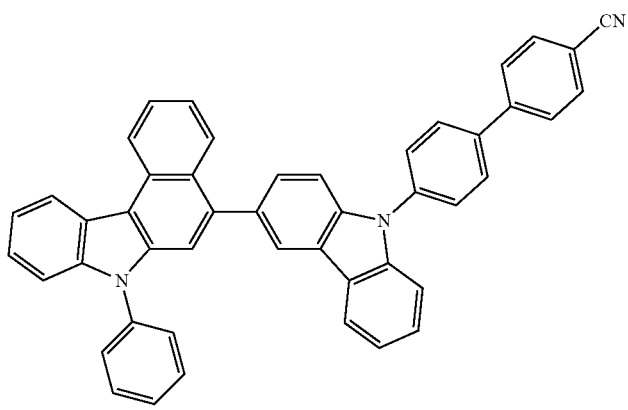

-continued
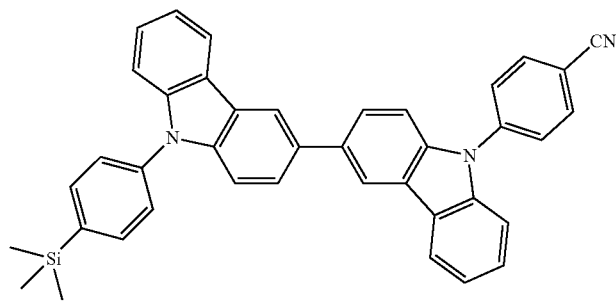
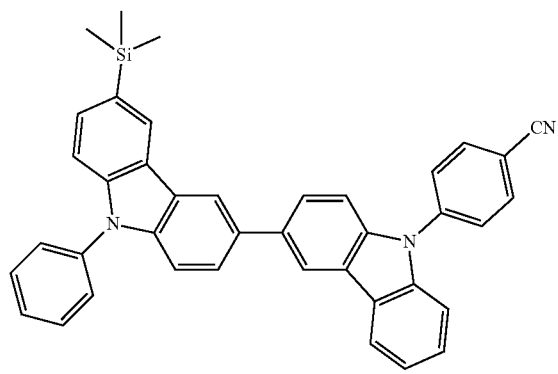
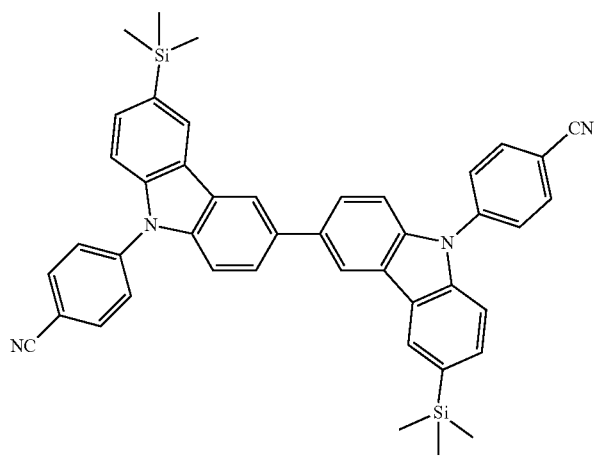
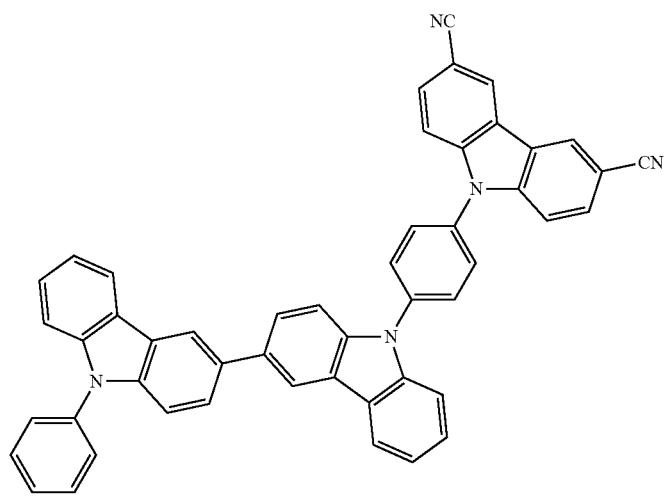

-continued
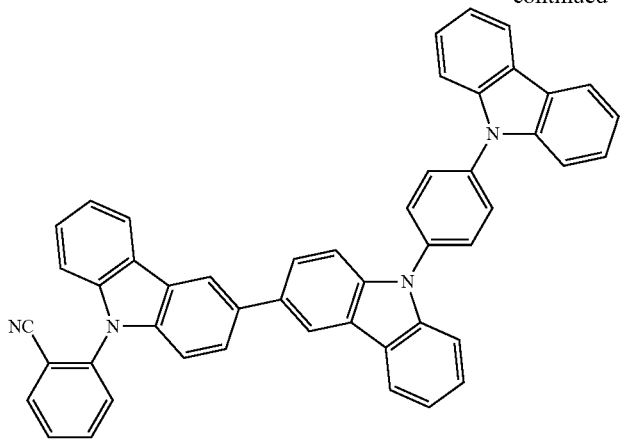
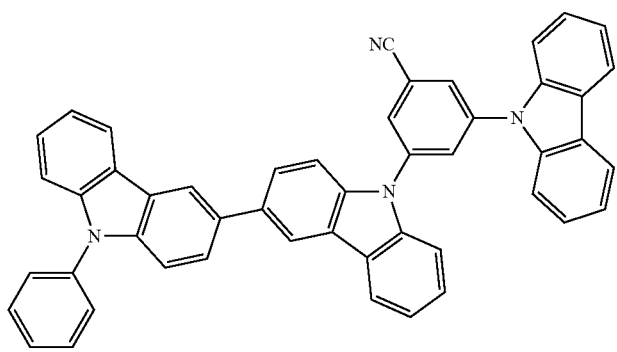
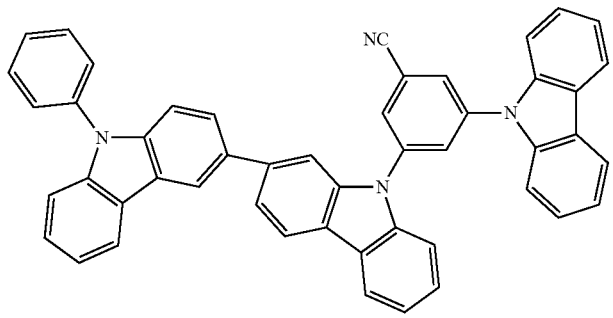
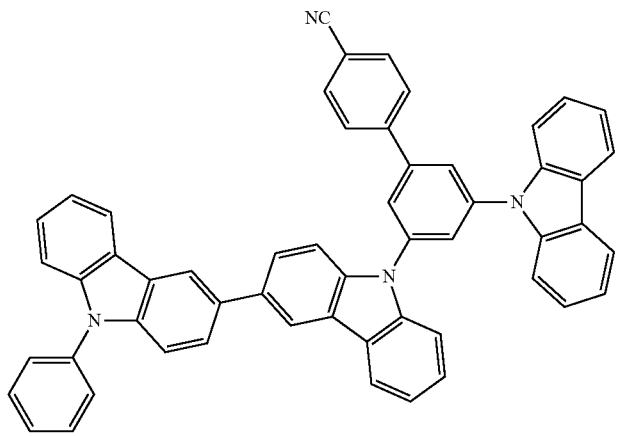

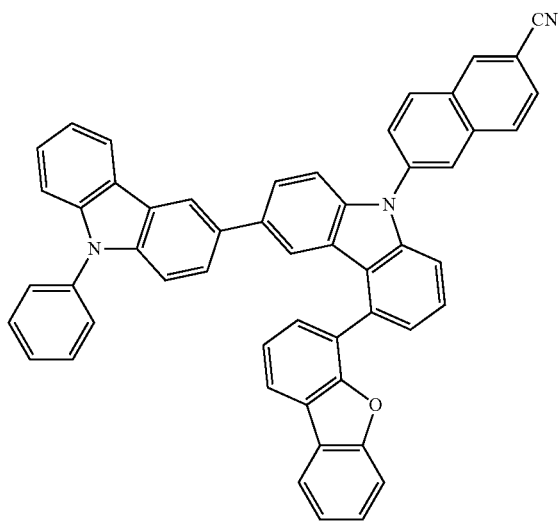
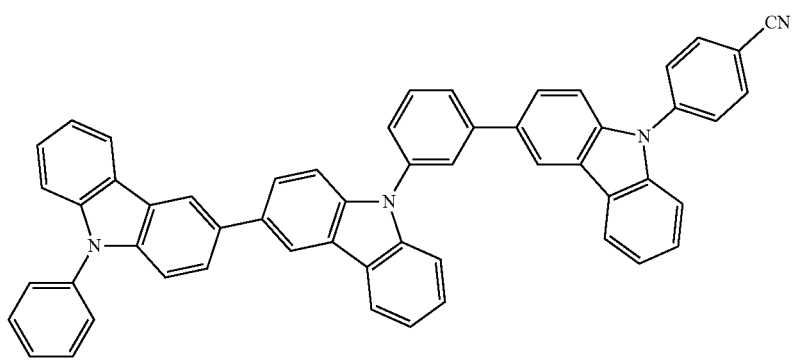
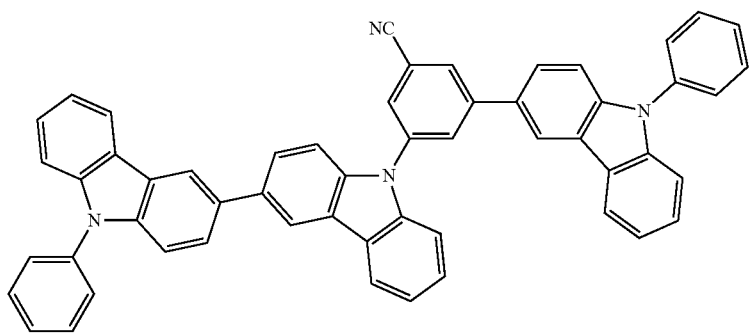

-continued
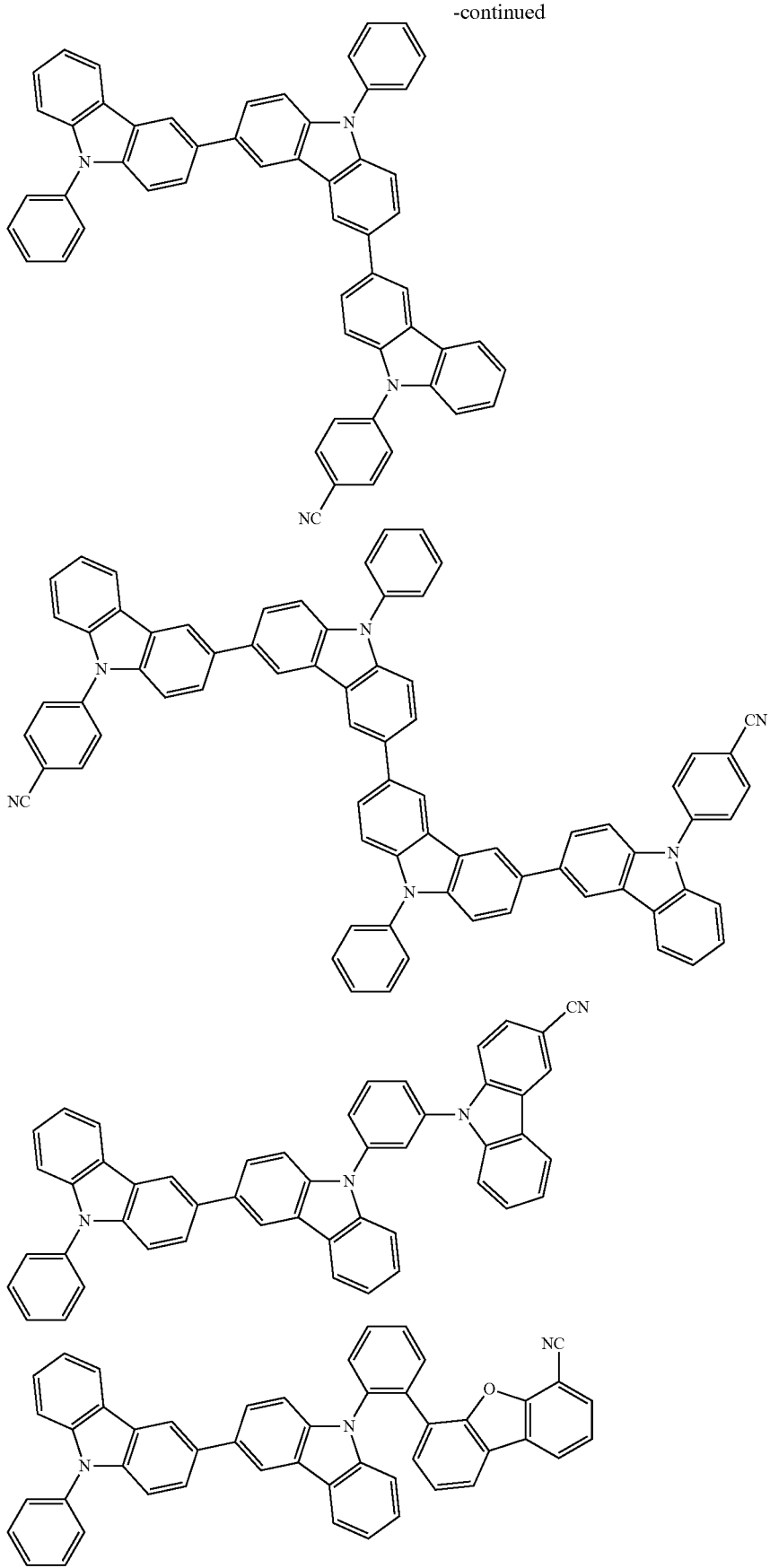

-continued
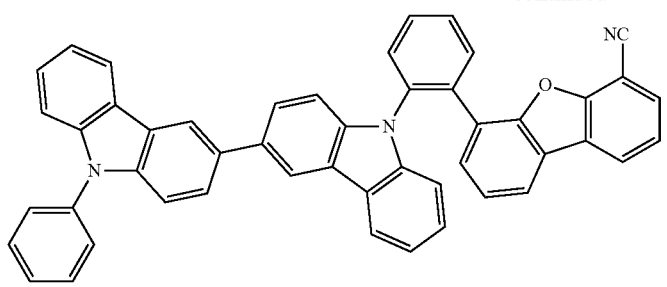
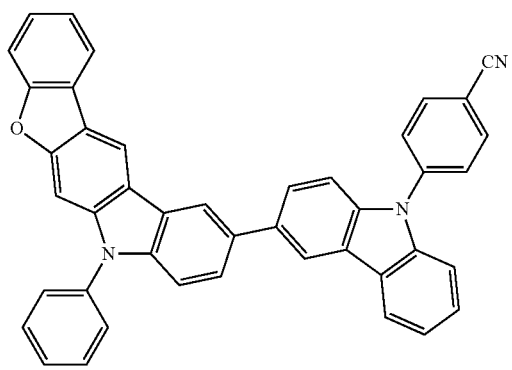
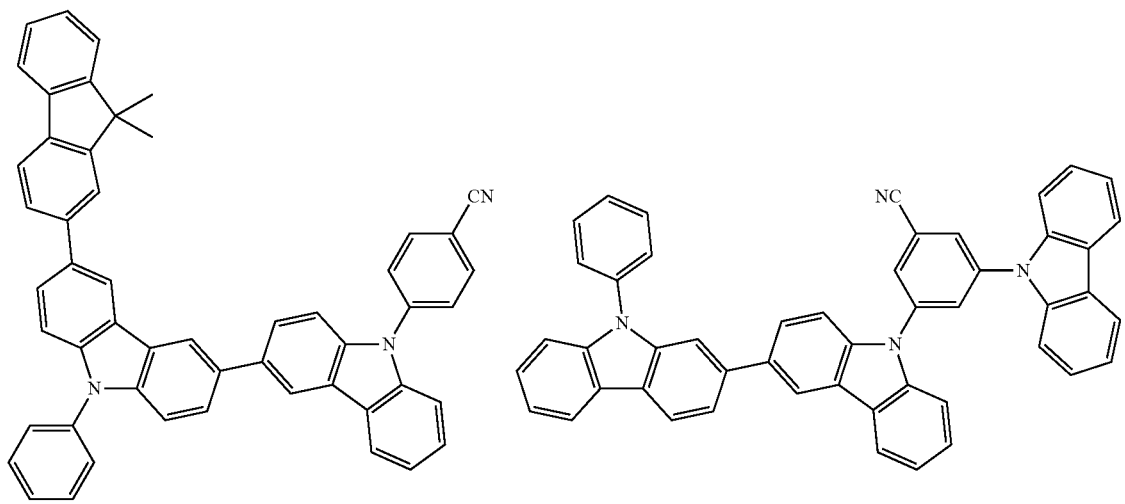
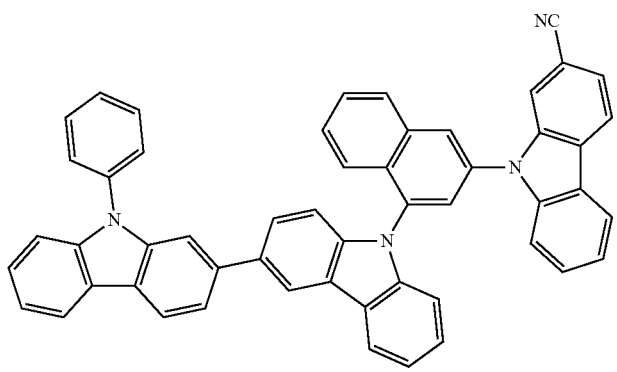

-continued
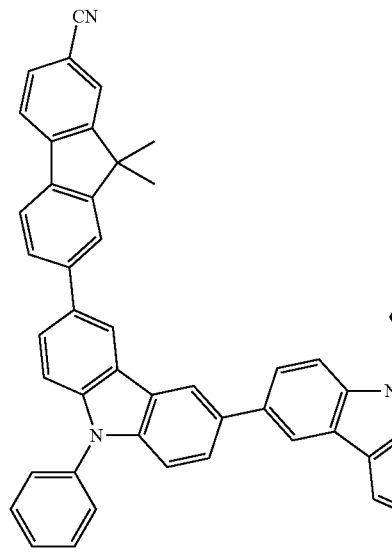
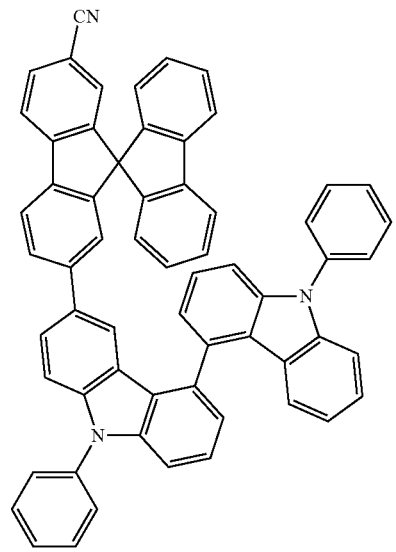
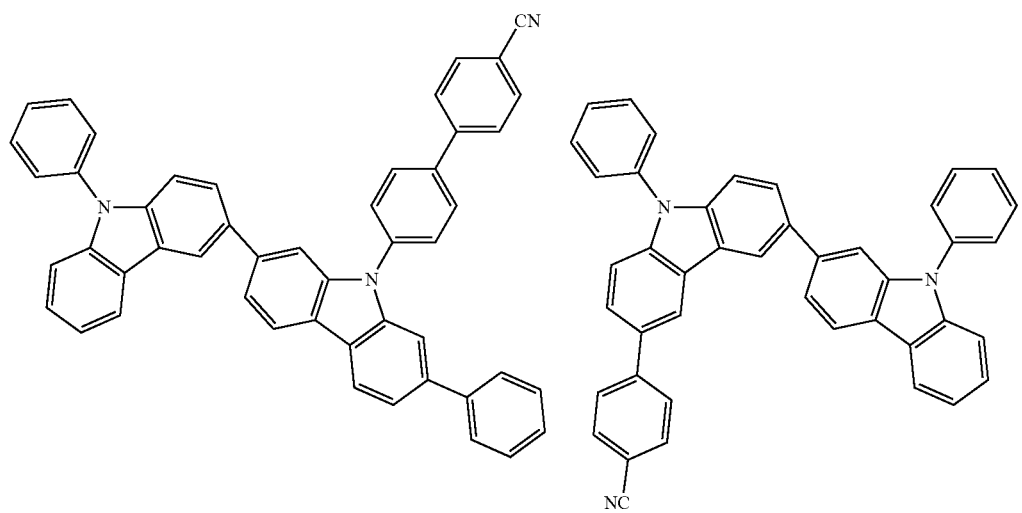
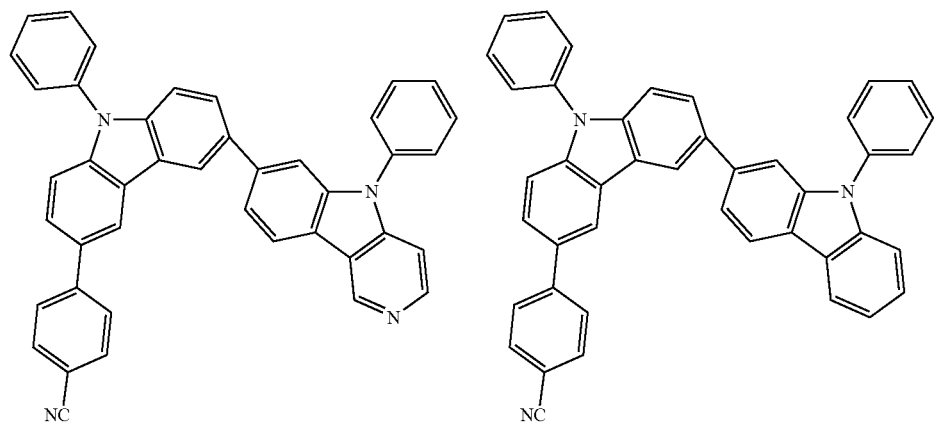

-continued
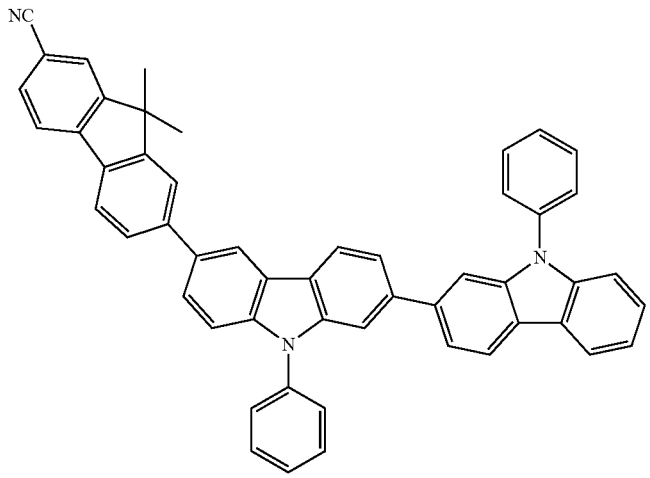
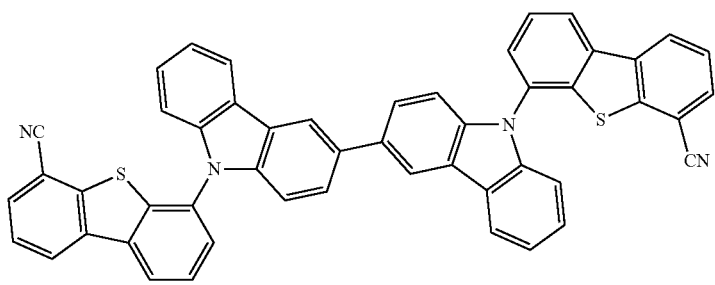
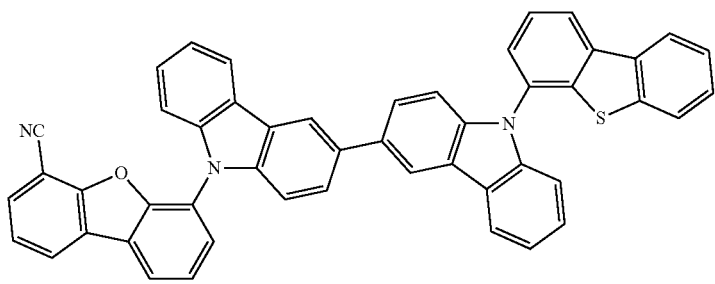 [SMILES: N#Cc1cccc2c1oc1c(-n3c4ccccc4c4cc(-c5ccc6c(c5)c5ccccc5n6-c5cccc6c5sc5ccccc56)ccc43)cccc12]
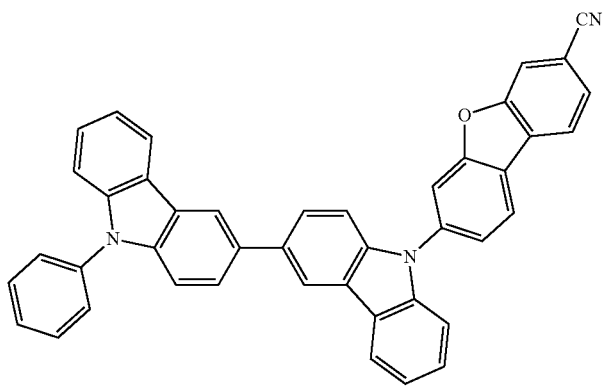

-continued
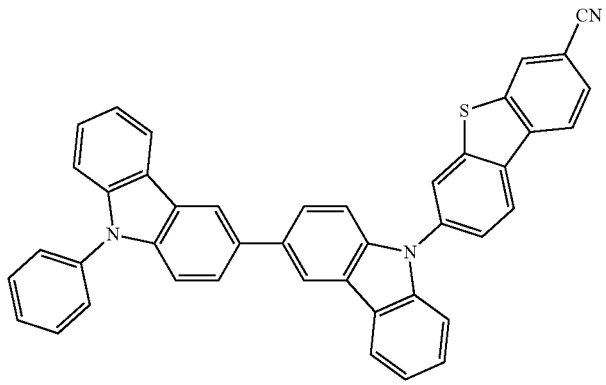
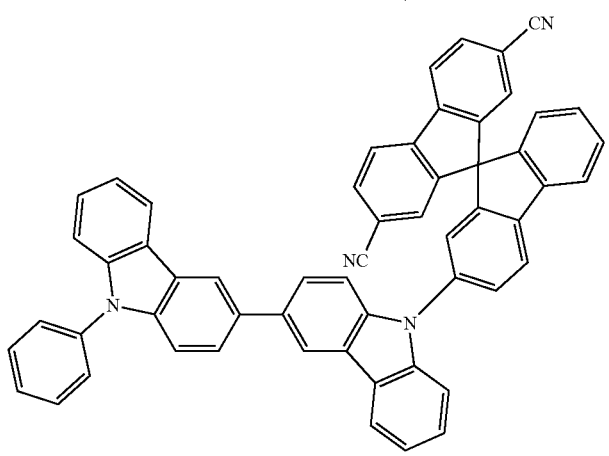
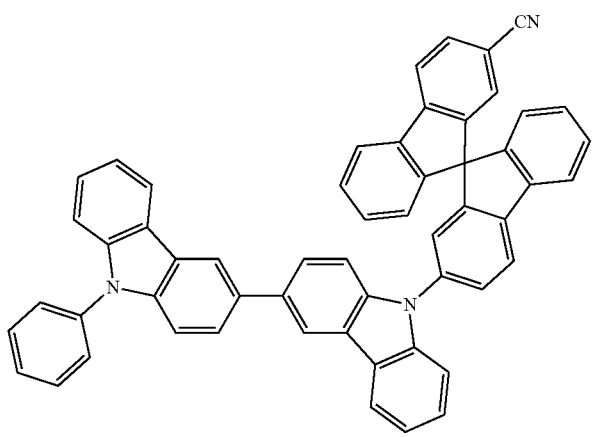
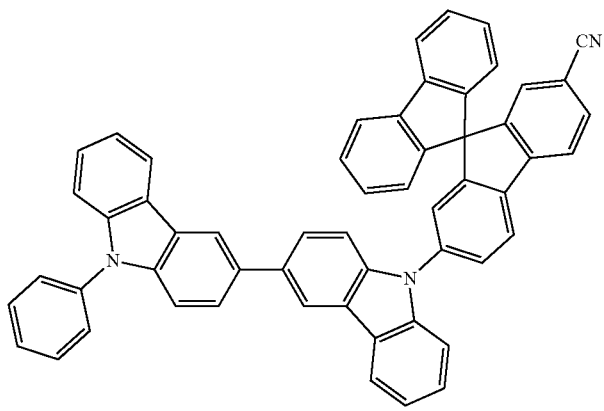

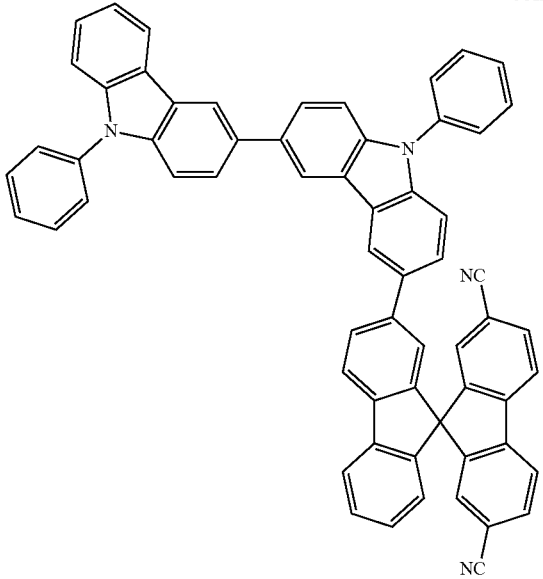

Organic EL Device

The embodiments of the organic EL device of the invention will be described below.

The organic EL device has an organic thin film layer between the cathode the anode. The organic thin film layer comprises a light emitting layer and at least one layer of the organic thin film layer comprises the material for organic EL device mentioned above. By allowing the material for organic EL device of the invention to be included in at least one layer of the organic thin film layer, an organic EL device with high emission efficiency is expected.

The organic thin film layer comprising the material for organic EL device of the invention may include a hole transporting layer, a light emitting layer, a space layer, an electron transporting layer, and a blocking layer, although not limited thereto. The material for organic EL device of the invention is preferably included in a light emitting layer and particularly preferably included in a light emitting layer as a host material. The light emitting layer preferably comprises a fluorescent material or a phosphorescent material, more preferably comprises a phosphorescent material. In another aspect of the invention, the material for organic EL device is preferably included in a blocking layer or an electron transporting each being adjacent to the light emitting layer.

The organic EL device of the invention may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such a electron blocking layer or a hole blocking layer, electrons and holes are confined in the light emitting layer to increase the degree of charge recombination in the light emitting layer, thereby improving the emission efficiency.

Representative device structure of the tandem-type organic EL device is shown below.
(2) Anode/First Emission Unit/Intermediate Layer/Second Emission Unit/Cathode The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device of the invention is shown in FIG. 1 wherein the organic EL device 1 is constructed by a substrate 2, an anode 3, a cathode 4, and an emission unit 10 disposed between the anode 3 and the cathode 4. The emission unit 10 includes a light emitting layer 5 which comprises at least one phosphorescent light emitting layer containing a phosphorescent host and a phosphorescent dopant. A hole injecting/transporting layer 6, etc. may be disposed between the light emitting layer 5 and the anode 3, and an electron injecting/transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, the host is referred to as a fluorescent host when combinedly used with a fluorescent dopant and as a phosphorescent host when combinedly used with a phosphorescent dopant. Therefore, the fluorescent host and the phosphorescent host are not distinguished from each other merely by the difference in their molecular structures. Namely, the term "phosphorescent host" means a material for constituting a phosphorescent emitting layer containing a phosphorescent dopant and does not mean that the material is not usable as a material for constituting a fluorescent emitting layer. The same also applies to the fluorescent host.

Substrate

The organic EL device of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds Ω/□ or less. The film thickness of anode depends upon the kind of material and generally 10 nm to 1 μm, preferably 10 to 200 nm.

Cathode

The cathode injects electrons to the electron injecting layer, the electron transporting layer or the light emitting layer, and preferably formed from a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken from the cathode, if appropriate.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, a double host (host and co-host) system may be used for the light emitting layer, for example, by combinedly using an electron transporting host and a hole transporting host.

Also, a double dopant system may be used, in which two or more kinds of dopant materials having a high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent material) is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. A ligand having an ortho metal bond, is preferred. In view of obtaining a high phosphorescent quantum yield and further improving the external quantum efficiency of electroluminescence device, a metal complex comprising a metal selected from Ir, Os, and Pt is preferred, with iridium complex, osmium complex, and platinum, particularly an ortho metallated complex thereof being more preferred, iridium complex and platinum complex being still more preferred, and an ortho metallated iridium complex being particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.

Preferred examples of the organometallic complex usable as the phosphorescent dopant are shown below.

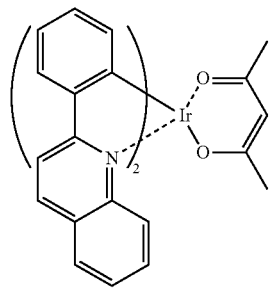

PQIr

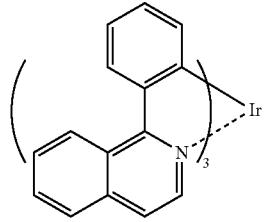

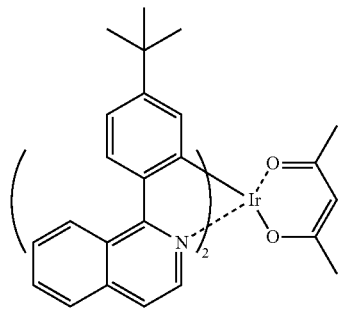

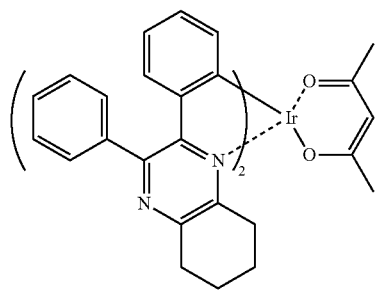

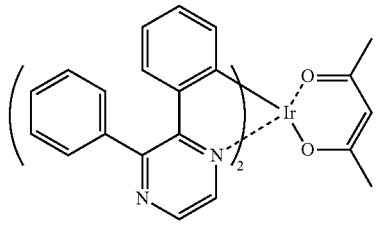

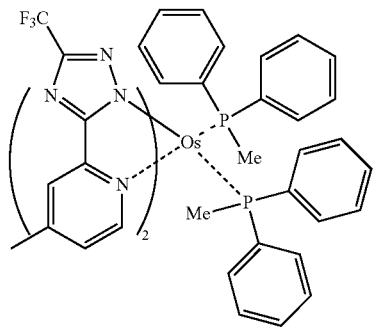

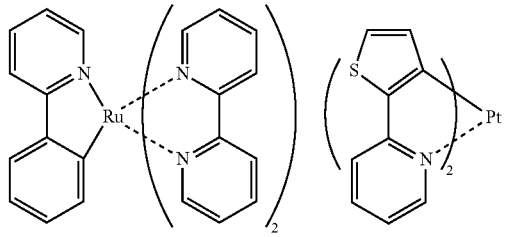

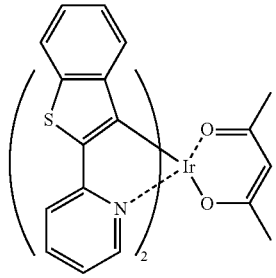

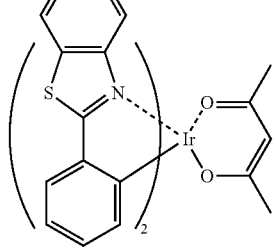

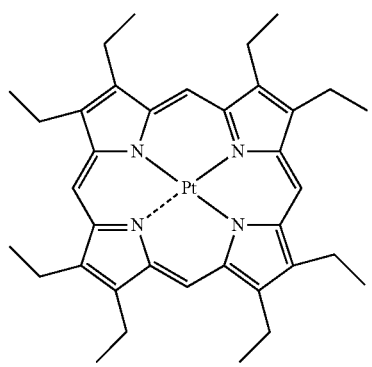

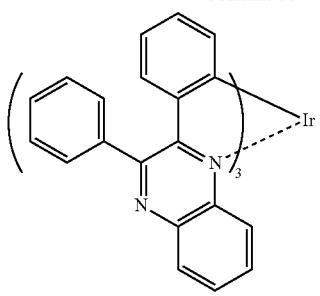
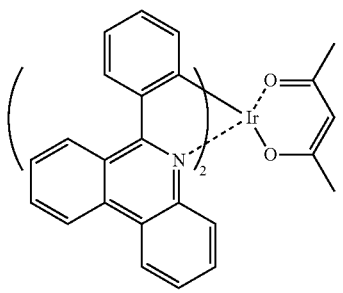
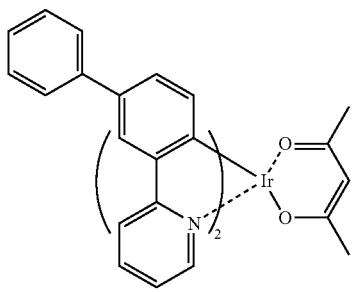
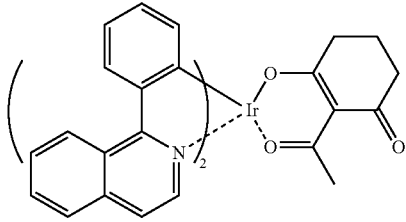
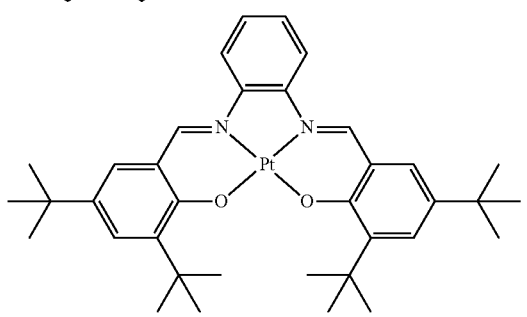
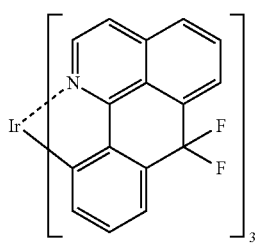
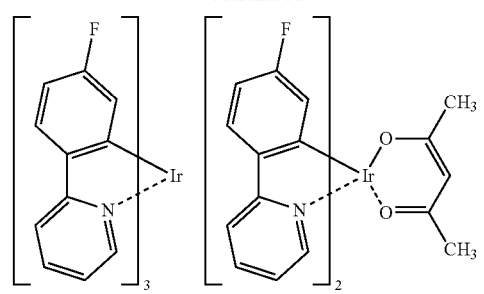
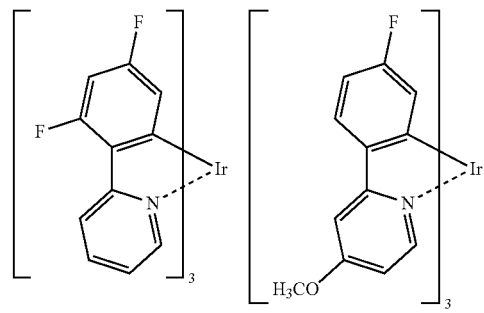
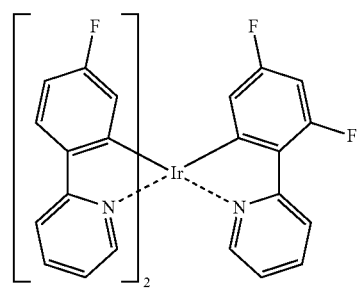
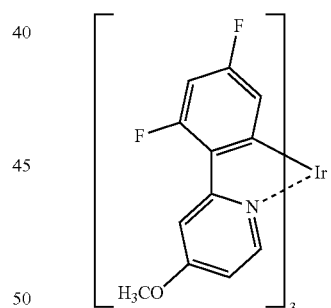
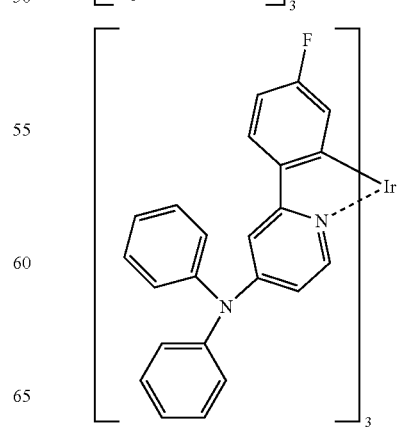

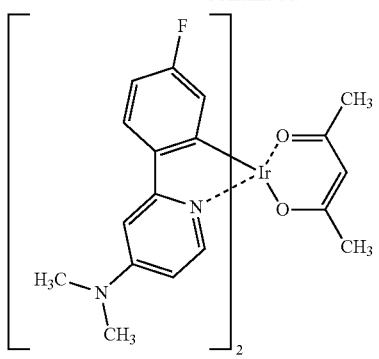
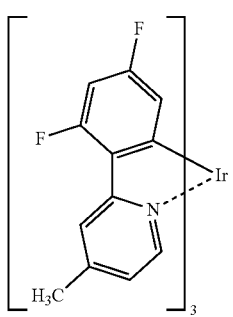
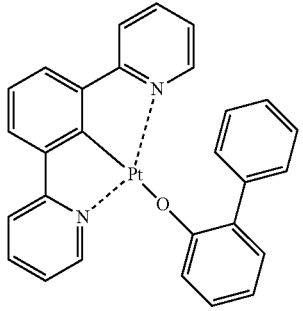
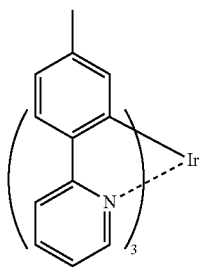
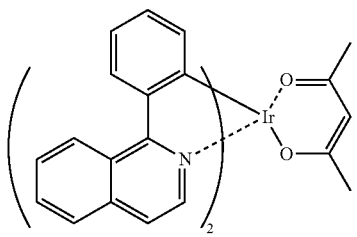
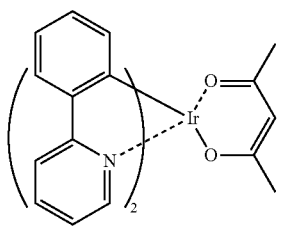
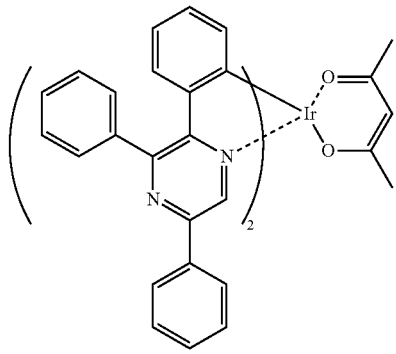
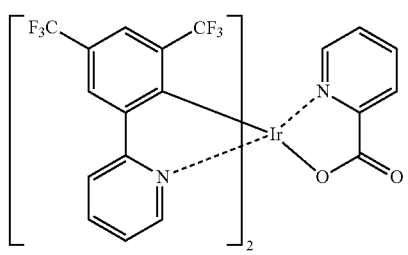
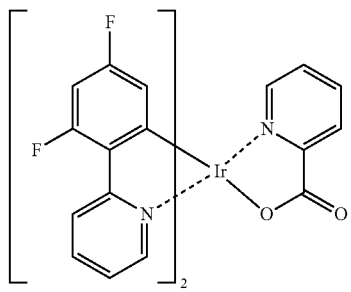
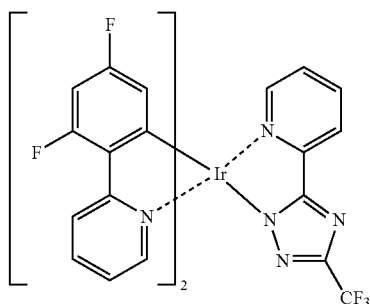
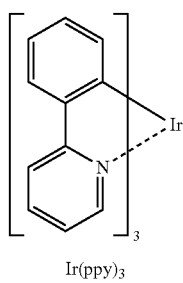
Ir(ppy)₃

101
-continued
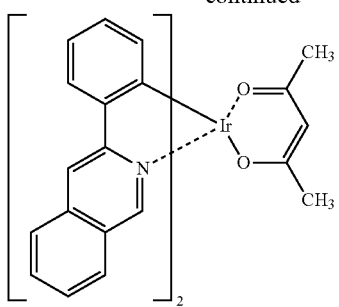
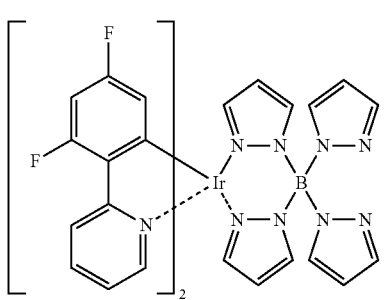
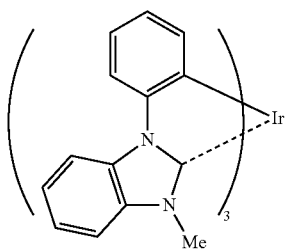
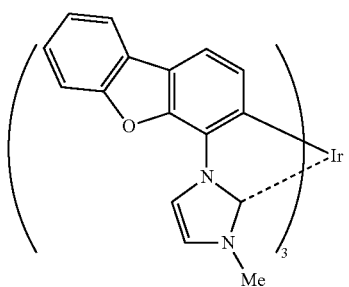
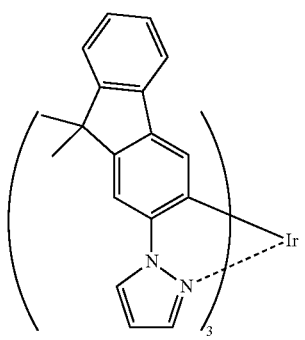
102
-continued
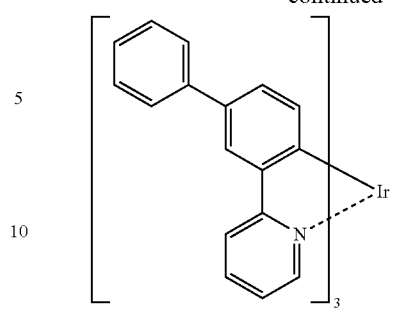
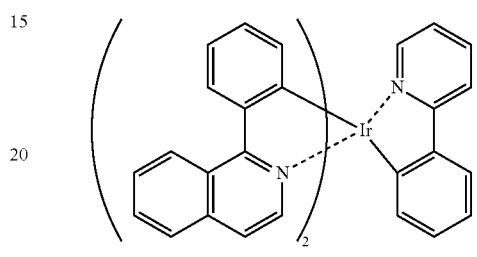
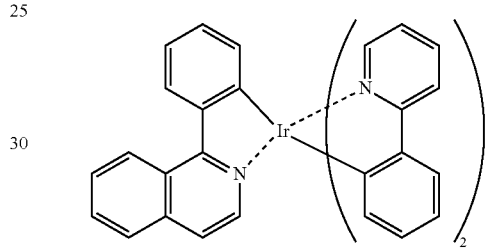
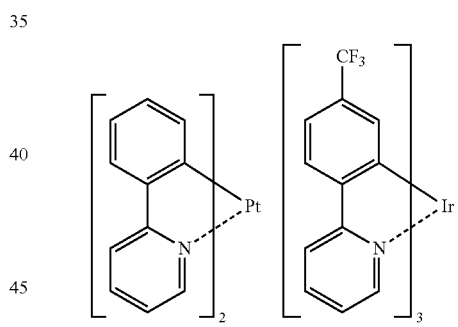
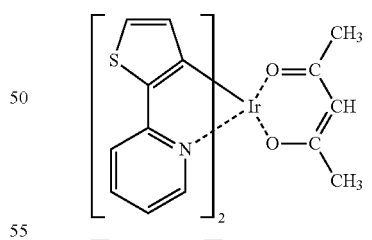
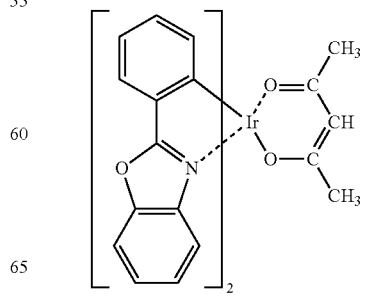

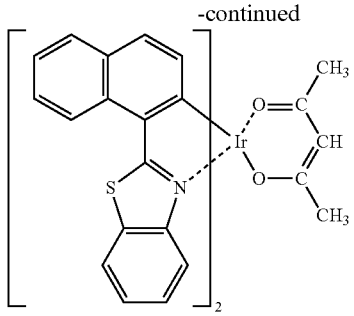

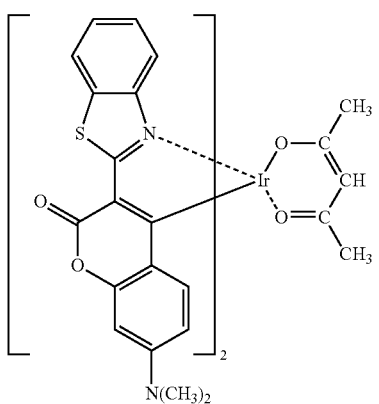

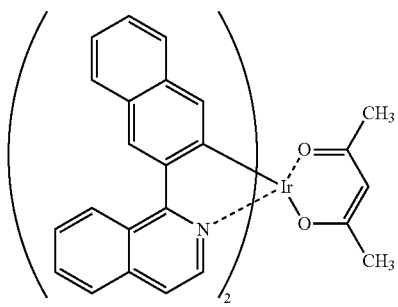

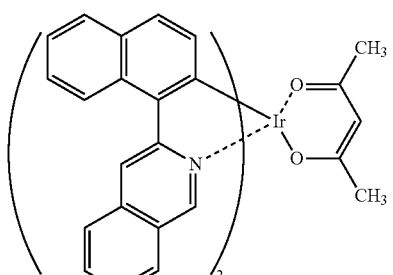

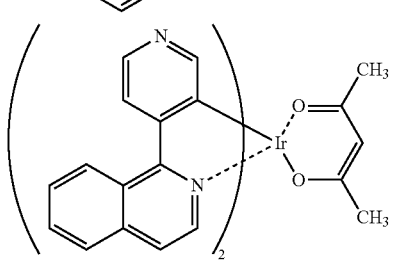

The phosphorescent host is a compound which confines the triplet energy of the phosphorescent dopant efficiently in the light emitting layer to cause the phosphorescent dopant to emit light efficiently. The material for organic EL device of the invention is useful as a phosphorescent host. In addition to the material for organic EL device of the invention, other compounds may be used as the phosphorescent host, if appropriate.

The material for organic EL device of the invention and a compound outside the invention may be combinedly used as the phosphorescent host in the same light emitting layer or may be separately used as the phosphorescent host in different light emitting layers. The material for organic EL device of the invention may be used in an organic layer other than the light emitting layer. If used in this manner, a compound outside the invention may be used as the phosphorescent host in the light emitting layer.

Examples of the compounds other than the material for organic EL device of the invention, which is suitable as the phosphorescent host, include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Specific examples thereof are shown below.

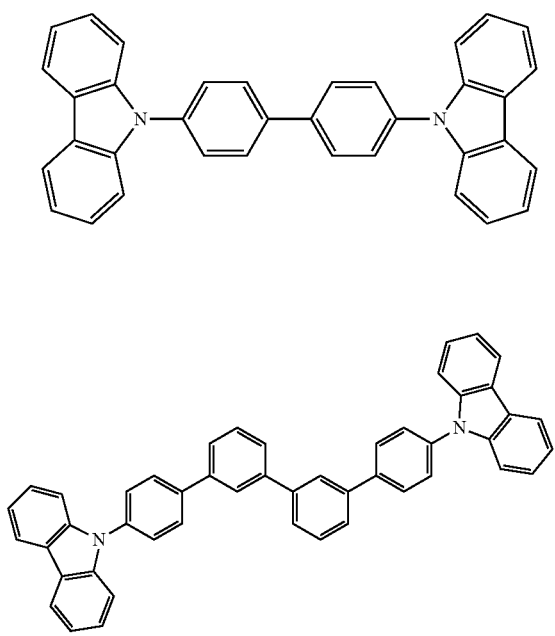

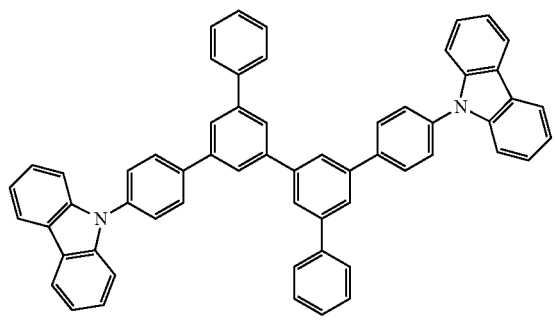

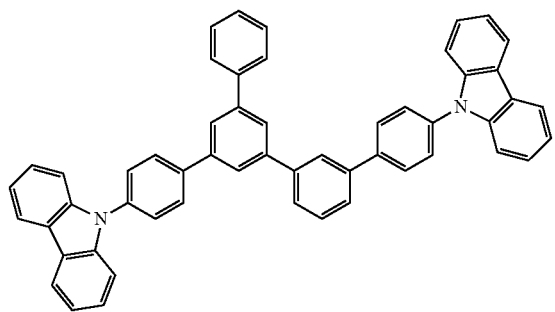

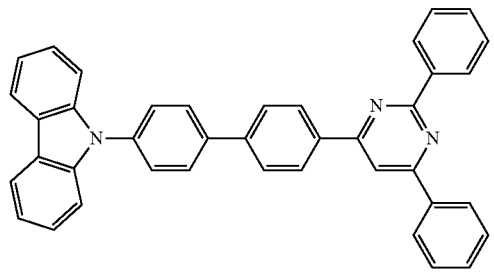

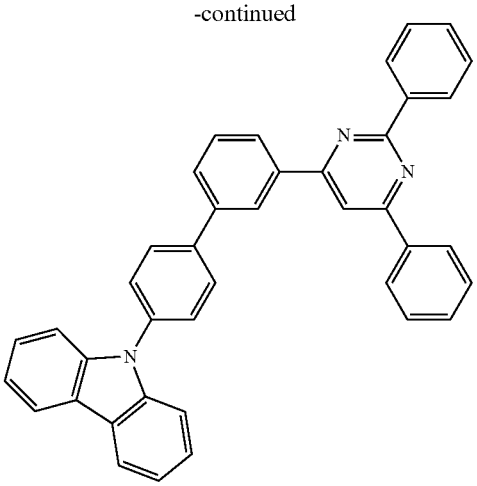

The thickness of the light emitting layer is preferably 5 to 50 nm, more preferably 7 to 50 nm, and still more preferably 10 to 50 nm. If being 5 nm or more, the light emitting layer is easily formed. If being 50 nm or less, the increase in driving voltage is avoided.

Electron-Donating Dopant

It is preferred for the organic EL device of the invention to contain an electron-donating dopant in the interfacial region between the cathode and the light emitting unit. With such a construction, the organic EL device has an improved luminance and an elongated lifetime. The electron-donating dopant is a metal having a work function of 3.8 eV or less or a compound containing such metal. Examples thereof include at least one compound selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ ($0<x<1$) and $Ba_xCA^1_{-x}O$ ($0<x<1$), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material, etc.) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device of the invention is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently. The material for organic EL device of the invention may be used in the electron transporting layer as an electron transporting material.

An aromatic heterocyclic compound having one or more heteroatoms in its molecule is preferably used as the electron transporting material for the electron transporting layer, with a nitrogen-containing ring derivative being particularly preferred. The nitrogen-containing ring derivative is preferably an aromatic ring compound having a nitrogen-containing 6- or 5-membered ring or a condensed aromatic ring compound having a nitrogen-containing 6- or 5-membered ring.

The nitrogen-containing ring derivative is preferably, for example, a chelate metal complex having a nitrogen-containing ring represented by formula (A).

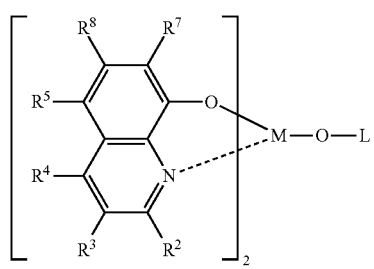

(A)

$R^2$ to $R^7$ of formula (A) each independently represent a hydrogen atom, a a deuterium atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or a heterocyclic group having 5 to 50 carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by $—NQ^1Q^2$, wherein $Q^1$ and $Q^2$ each independently represent an alkyl group having 1 to 20 carbon atoms or an aralkyl group having 1 to 20 carbon atoms. One of $Q^1$ and $Q^2$ may be a hydrogen atom or a deuterium atom.

The arylamino group is represented by $—NAr^1Ar^2$, wherein $Ar^1$ and $Ar^2$ each independently represent a non-condensed aromatic hydrocarbon group or a condensed aromatic hydrocarbon group each having 6 to 50 carbon atoms. One of $Ar^1$ and $Ar^2$ may be a hydrogen atom or a deuterium atom.

The hydrocarbon group having 1 to 40 carbon atoms may include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

L is a group represented by formula (A') or (A''):

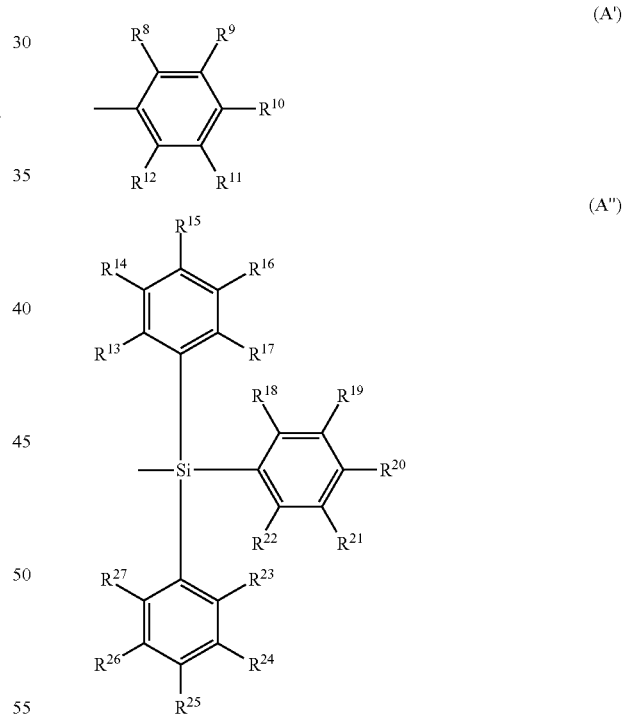

$R^8$ to $R^{12}$ in formula (A') each independently represent a hydrogen atom, a deuterium atom, or a substituted or unsubstituted hydrocarbon group having 1 to 40 carbon atoms. The adjacent two groups may form a ring structure. $R^{13}$ to $R^{27}$ in formula (A'') each independently represent a hydrogen atom, a deuterium atom, or a substituted or unsubstituted hydrocarbon group having 1 to 40 carbon atoms. The adjacent two groups may form a ring structure.

Examples of the hydrocarbon group having 1 to 40 carbon atoms for $R^8$ to $R^{12}$ and $R^{13}$ to $R^{27}$ in formulae (A') and (A'') are the same as those described above with respect to $R^2$ to $R^7$.

Examples of the divalent group formed by the adjacent two groups of $R^8$ to $R^{12}$ and $R^{13}$ to $R^{27}$ which completes the ring structure include tetramethylene group, pentamethylene group, hexamethylene group, diphenylmethane-2,2'-diyl group, diphenylethane-3,3'-diyl group, and diphenylpropane-4,4'-diyl group.

The electron transporting compound for the electron transporting layer is preferably a metal complex including 8-hydroxyquinoline or its derivative, an oxadiazole derivative, and a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol)aluminum. Examples of the oxadiazole derivative are shown below.

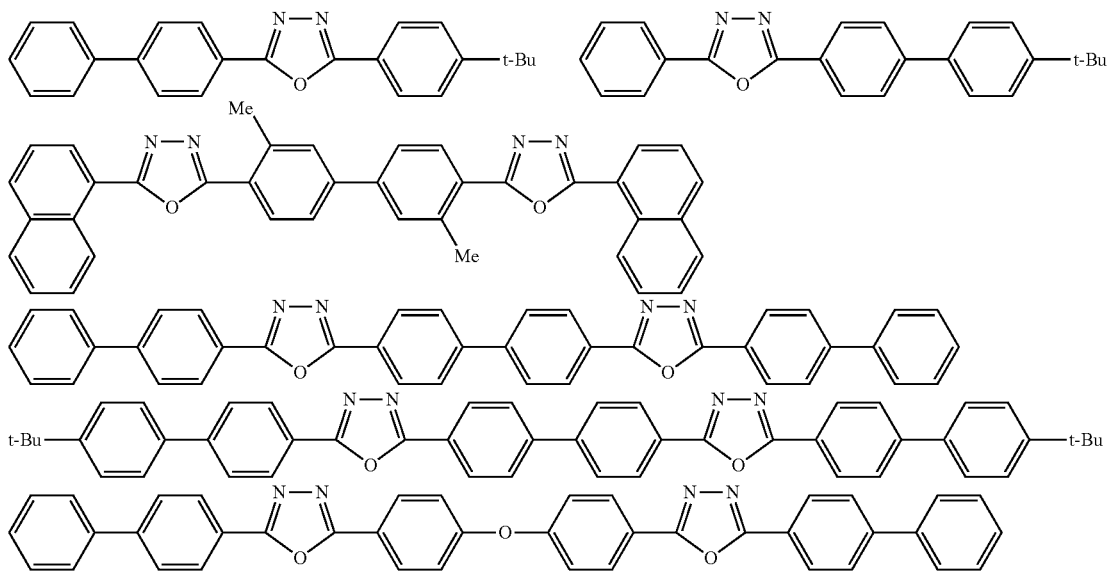

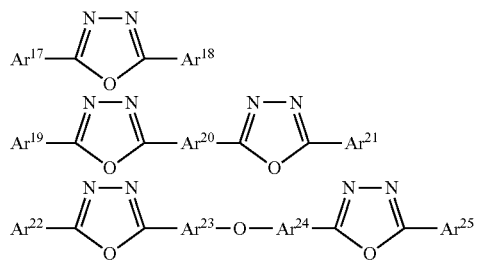

In the above formulae, each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted condensed aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the condensed aromatic hydrocarbon group include phenyl group, naphthyl group, biphenyl group, anthranyl group, perylenyl group, and pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted or unsubstituted bivalent condensed aromatic hydrocarbon group each having 6 to 50 carbon atoms, and $Ar^{23}$ and $Ar^{24}$ may be the same or different. Examples of the bivalent aromatic hydrocarbon group or the bivalent condensed aromatic hydrocarbon group include phenylene group, naphthylene group, biphenylene group, anthranylene group, perylenylene group, and pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C).

In formula (C), X is a carbon atom or a nitrogen atom. $Z_1$ and $Z_2$ each independently represent a group of atoms for completing the nitrogen-containing heteroring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D).

 (D)

The nitrogen-containing group of the nitrogen-containing aromatic polycyclic compound is selected, for example, from the nitrogen-containing heterocyclic groups shown below.

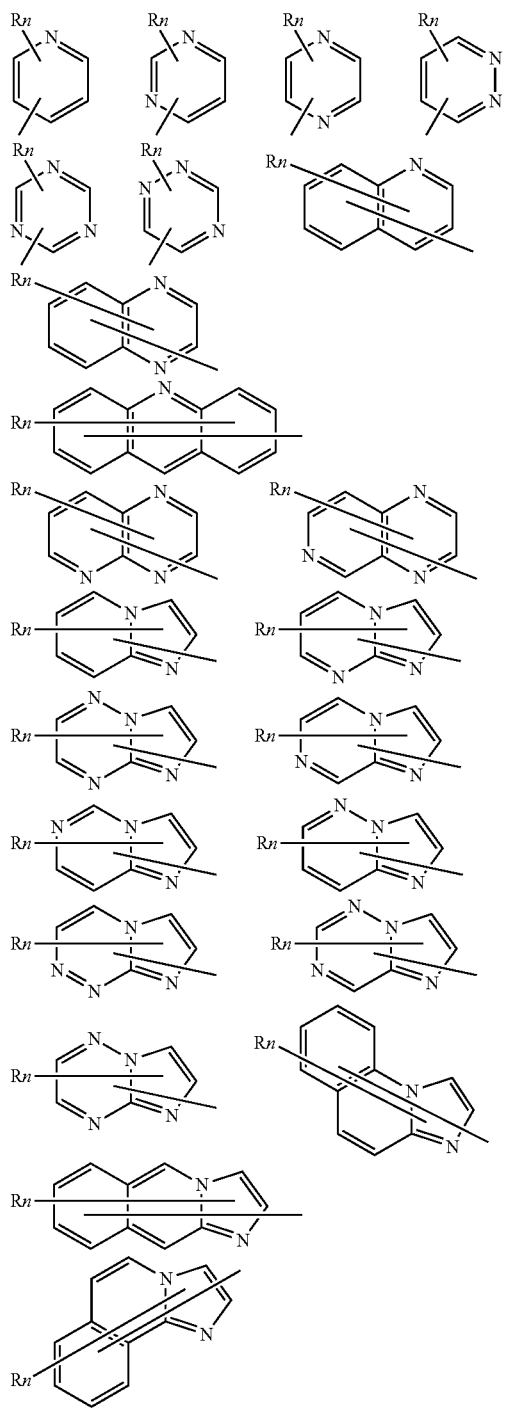

In the above formulae, R is an aromatic hydrocarbon group or a condensed aromatic hydrocarbon group each having 6 to 40 carbon atoms, an aromatic heterocyclic group or a condensed aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, R groups may be the same or different.

More preferred is a nitrogen-containing heterocyclic derivative represented by the following formula:

$$HAr\text{-}L^1\text{-}Ar^1\text{---}Ar^2 \quad (D1)$$

wherein HAr is a substitute or unsubstituted nitrogen-containing heterocyclic group having 3 to 40 carbon atoms; $L^1$ is a single bond, a substituted or unsubstituted aromatic hydrocarbon group or condensed aromatic hydrocarbon group each having 6 to 40 carbon atoms, or a substituted or unsubstituted aromatic heterocyclic group or condensed aromatic heterocyclic group each having 3 to 40 carbon atoms; $Ar^1$ is a substitute or unsubstituted divalent aromatic hydrocarbon group having 6 to 40 carbon atoms; and Are is a substitute or unsubstituted aromatic hydrocarbon group or condensed aromatic hydrocarbon group each having 6 to 40 carbon atoms or a substituted or unsubstituted aromatic heterocyclic group or condensed aromatic heterocyclic group each having 3 to 40 carbon atoms.

HAr is selected, for example, from the following groups:

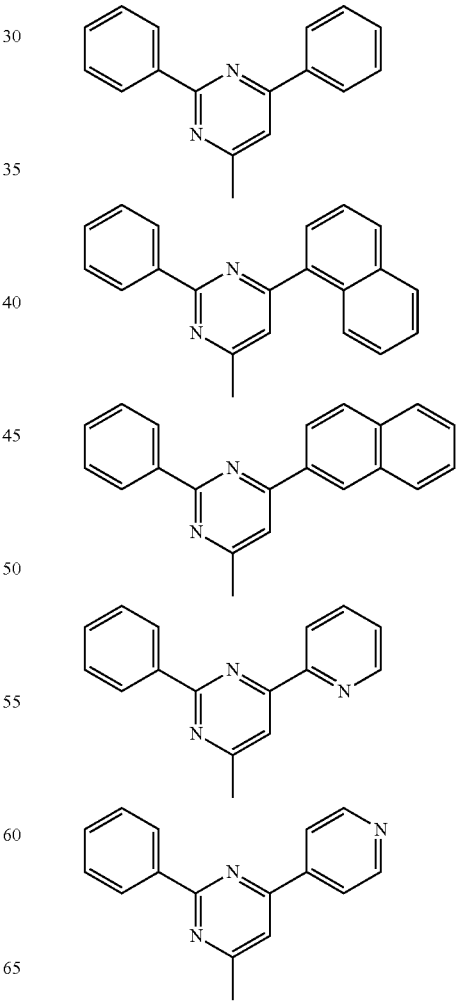

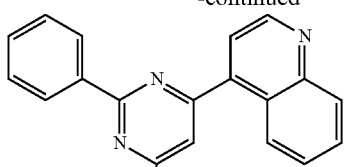
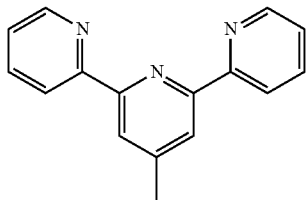
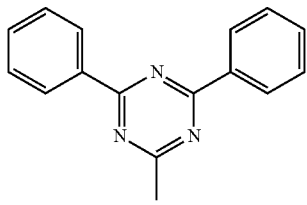
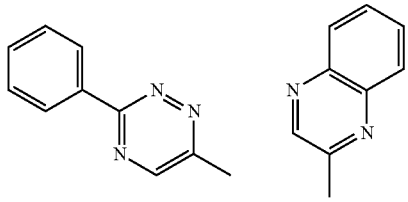
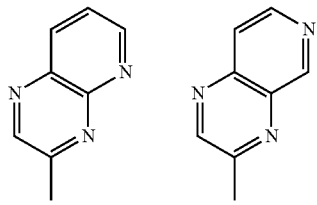
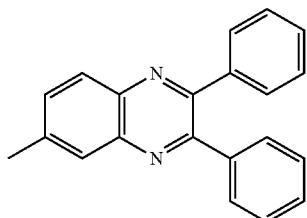
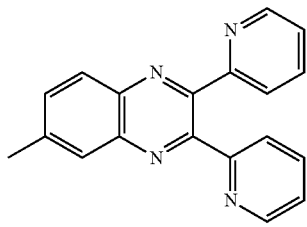
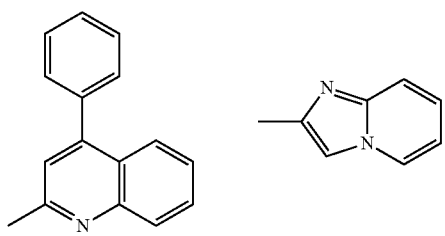

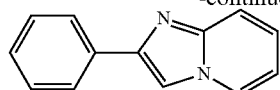
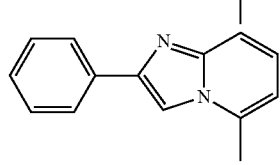
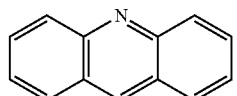
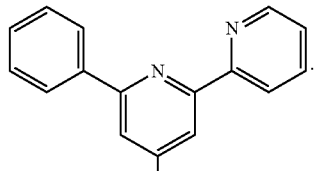

$L^1$ is selected, for example, from the following groups:

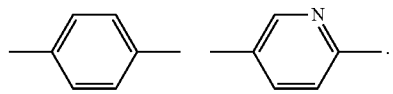

$Ar^1$ is selected, for example, from the following arylanthranyl groups represented by formula (D2) or (D3):

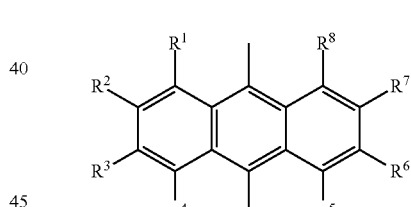

(D2)

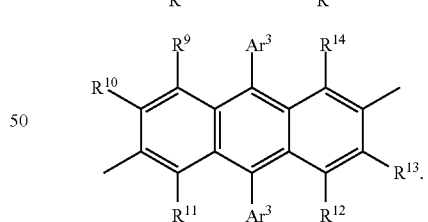

(D3)

In the above formulae (D2) and (D3), $R^1$ to $R^{14}$ are each independently a hydrogen atom, a deuterium atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or condensed aromatic hydrocarbon group each having 6 to 40 carbon atoms, or a substituted or unsubstituted aromatic heterocyclic group or condensed aromatic heterocyclic group each having 3 to 40 carbon atoms; and Ara is a substituted or unsubstituted aromatic hydrocarbon group or condensed aromatic hydrocarbon group each having 6 to 40 carbon atoms or a substituted or unsubstituted aromatic heterocyclic group or condensed aromatic heterocyclic group each having 3 to 40 carbon atoms. $R^1$ to $R^8$ may be all selected from a hydrogen atom and a deuterium atom.

$Ar^2$ is selected, for example, from the following groups:

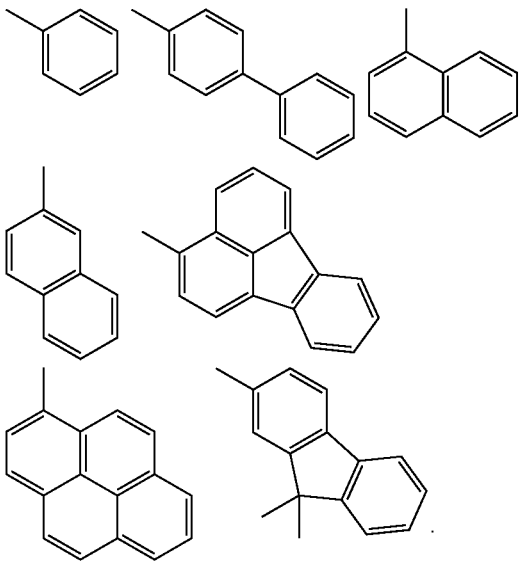

In addition, the following compound is preferably used as the nitrogen-containing aromatic polycyclic compound for use as the electron transporting compound.

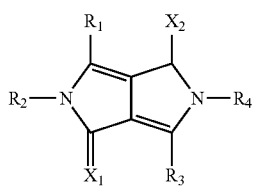

(D4)

In the formula (D4), $R_1$ to $R_4$ each independently represent a hydrogen atom, a deuterium atom, a substituted or unsubstituted aliphatic group having 1 to 20 carbon atoms, a substituted or unsubstituted alicyclic group having 3 to 20 carbon atoms, a substituted or unsubstituted aromatic group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound.

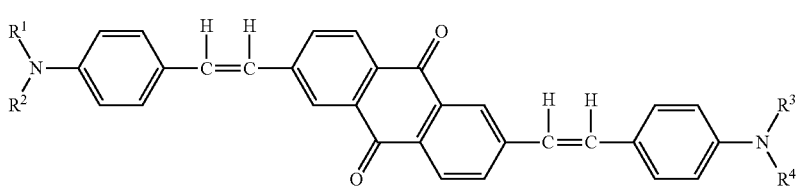

(D5)

In the formula (D5), $R^1$, $R^2$, $R^3$, and $R^4$ may be the same or different and each represents an aromatic hydrocarbon group or a condensed aromatic hydrocarbon group each represented by the following formula (D6):

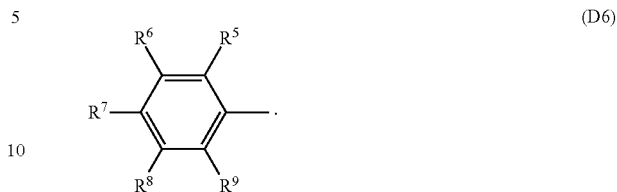

(D6)

In the formula (D6), $R^5$, $R^6$, $R^7$, $R^8$, and $R^9$ may be the same or different and each represents a hydrogen atom, a deuterium atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ is a group other than hydrogen atom and deuterium atom.

Further, a polymer having the nitrogen-containing heterocyclic group or the nitrogen-containing heterocyclic derivative is also usable as the electron transporting compound.

It is particularly preferred for the electron transporting layer of the organic EL of the invention to contain at least one of the nitrogen-containing heterocyclic derivatives represented by the following formulae (E) to (G).

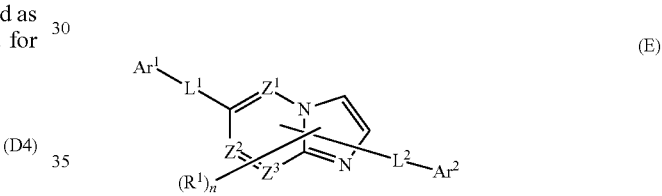

(E)

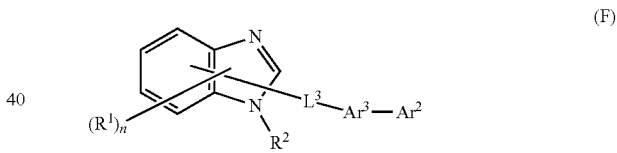

(F)

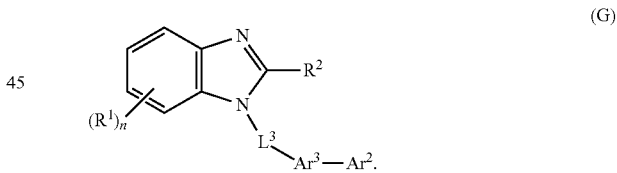

(G)

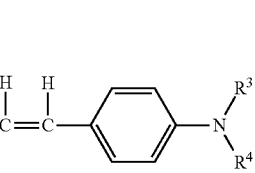

In the formulae (E) to (G), $Z^1$, $Z^2$, and $Z^3$ each independently represent a nitrogen atom or a carbon atom.

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms.

The subscript n is an integer of 0 to 5. If n is an integer of 2 or more, $R^1$ groups may be the same or different from each other. The adjacent two $R^1$ groups may bond to each other to form a substituted or unsubstituted hydrocarbon ring.

$Ar^1$ represents a substituted or unsubstituted aryl group having 6 to 50 ring carbon atoms or a substituted or unsubstituted heteroaryl group having 5 to 50 ring atoms.

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms.

However, one of $Ar^1$ and $Ar^2$ is a substituted or unsubstituted condensed aromatic hydrocarbon group having 10 to 50 ring carbon atoms or a substituted or unsubstituted condensed aromatic heterocyclic group having 9 to 50 ring atoms.

$Ar^3$ represents a substituted or unsubstituted arylene group having 6 to 50 ring carbon atoms or a substituted or unsubstituted heteroarylene group having 5 to 50 ring atoms.

$L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include phenyl group, naphthyl group, anthryl group, phenanthryl group, naphthacenyl group, chrysenyl group, pyrenyl group, biphenyl group, terphenyl group, tolyl group, fluoranthenyl group, and fluorenyl group.

Examples of the heteroaryl group having 5 to 50 ring atoms include pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazinyl group, triazinyl group, quinoxalinyl group, acridinyl group, imidazo[1,2-a]pyridinyl group, and imidazo[1,2-a]pyrimidinyl.

Examples of the alkyl group having 1 to 20 carbon atoms include methyl group, ethyl group, propyl group, butyl group, pentyl group, and hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably 1 to 100 nm, although not particularly limited thereto.

The electron injecting layer which may be formed adjacent to the electron transporting layer preferably includes an inorganic compound, such as an insulating material and a semiconductor in addition to the nitrogen-containing ring derivative. The insulating material or semiconductor incorporated into the electron injecting layer effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. incorporated into the electron injecting layer further enhances the electron injecting properties. Preferred examples of the alkali metal chalcogenides include $Li_2O$, $K_2O$, $Na_2S$, $Na_2Se$ and $Na_2O$, and preferred examples of the alkaline earth metal chalcogenides include CaO, BaO, SrO, BeO, BaS and CaSe. Preferred examples of the alkali metal halides include LiF, NaF, KF, LiCl, KCl and NaCl. Examples of the alkaline earth metal halides include fluorides such as $CaF_2$, $BaF_2$, $SrF_2$, $MgF_2$ and $BeF_2$ and halides other than fluorides.

Examples of the semiconductor may include oxide, nitride or oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound forming the electron injecting layer preferably forms a microcrystalline or amorphous insulating thin film. When the electron injecting layer is formed from such an insulating thin film, the thin film is made more uniform to decrease the pixel defects such as dark spots. Examples of such inorganic compound include alkali metal chalcogenides, alkaline earth metal chalcogenides, alkali metal halides and alkaline earth metal halide, each being described above.

The thickness of the layer including the insulating material or the semiconductor is preferably about 0.1 to 15 nm. The electron injecting layer may be included with the electron-donating dopant described above.

Hole Transporting Layer

The hole transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit.

An aromatic amine compound, for example, the aromatic amine derivative represented by formula (H), is also preferably used as the material for forming the hole transporting layer.

(H)

In the formula (H), each of $Ar^1$ to $Ar^4$ represents a substituted or unsubstituted aromatic hydrocarbon group or condensed aromatic hydrocarbon group having 6 to 50 ring carbon atoms, a substituted or unsubstituted aromatic heterocyclic group or condensed aromatic heterocyclic group having 5 to 50 ring atoms, or a group wherein the aromatic hydrocarbon group or condensed aromatic hydrocarbon group and the aromatic heterocyclic group or condensed aromatic heterocyclic group are boned to each other.

L represents a substituted or unsubstituted aromatic hydrocarbon group or condensed aromatic hydrocarbon group each having 6 to 50 ring carbon atoms or a substituted or unsubstituted aromatic heterocyclic group or condensed aromatic heterocyclic group each having 5 to 50 ring atoms.
Specific examples of the compound represented by the formula (H) are shown below.
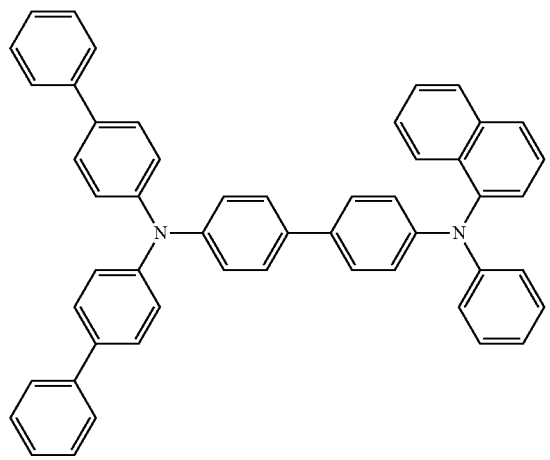
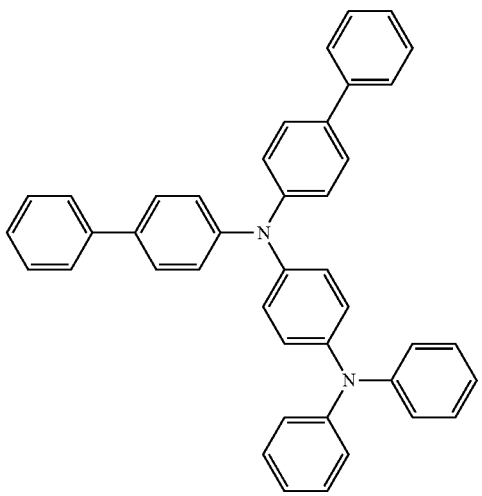
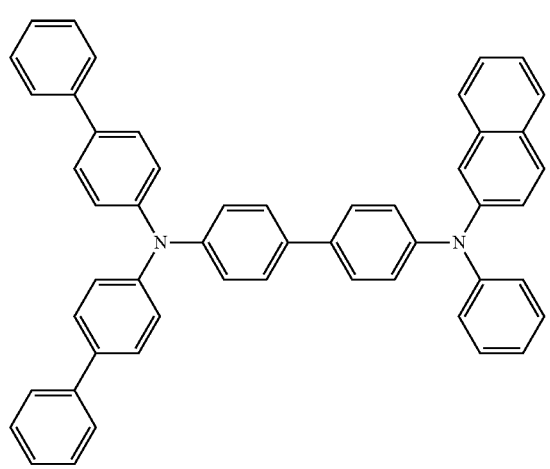
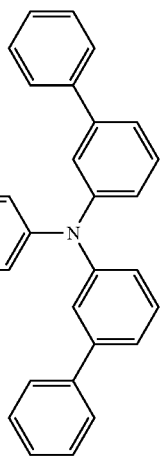
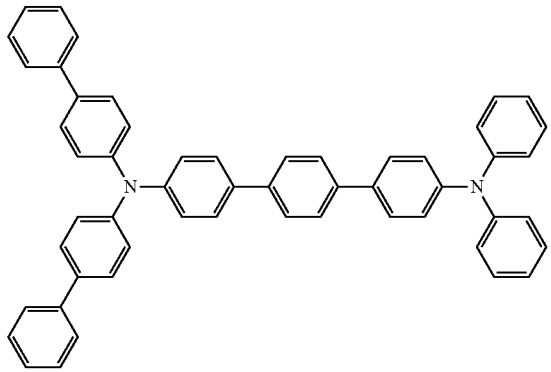
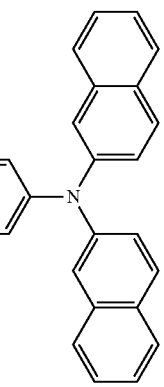

121
-continued
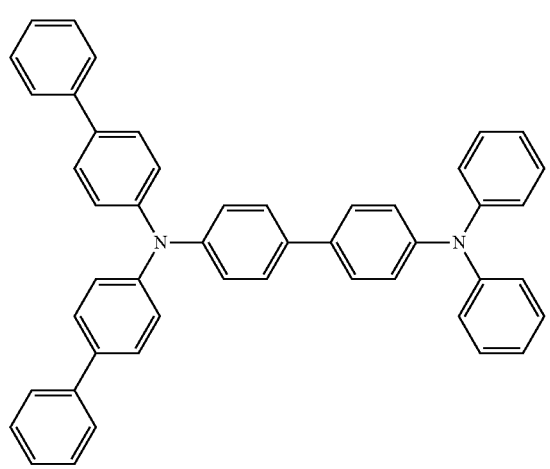
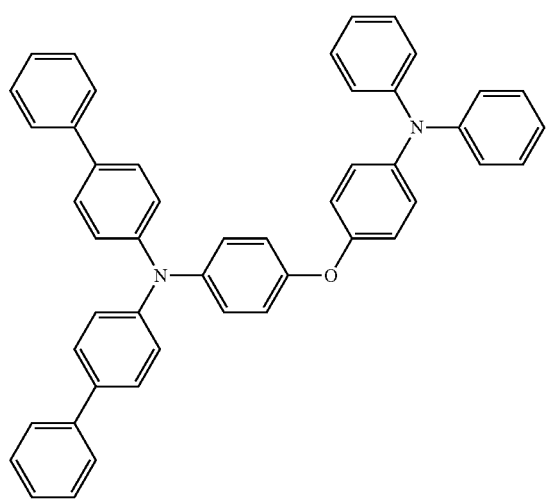
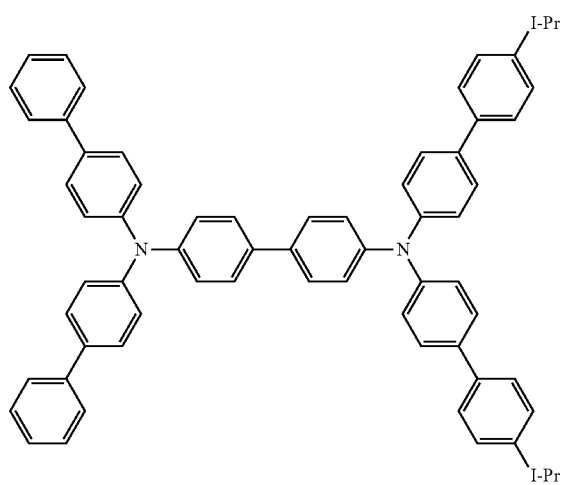
122
-continued
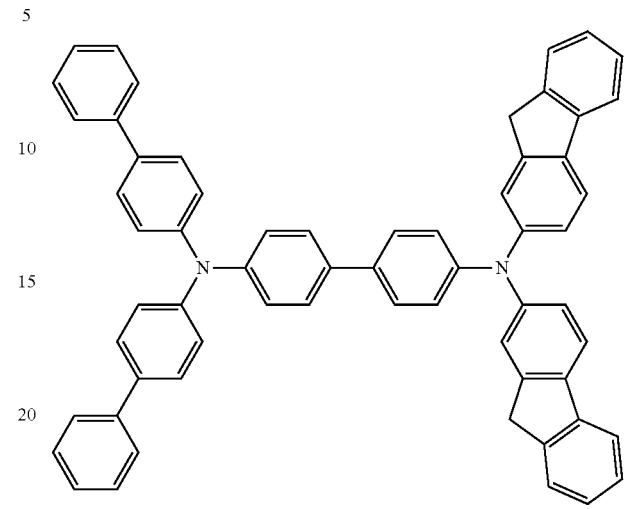

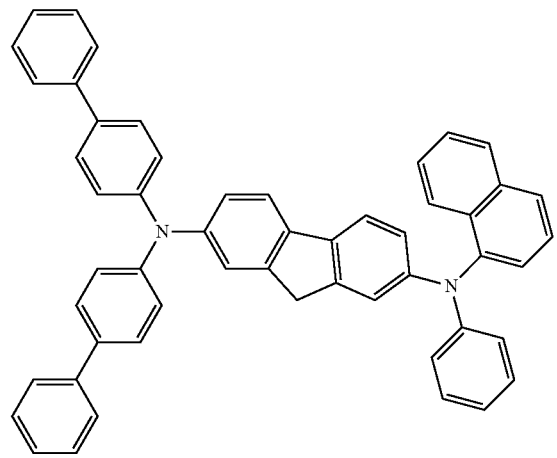
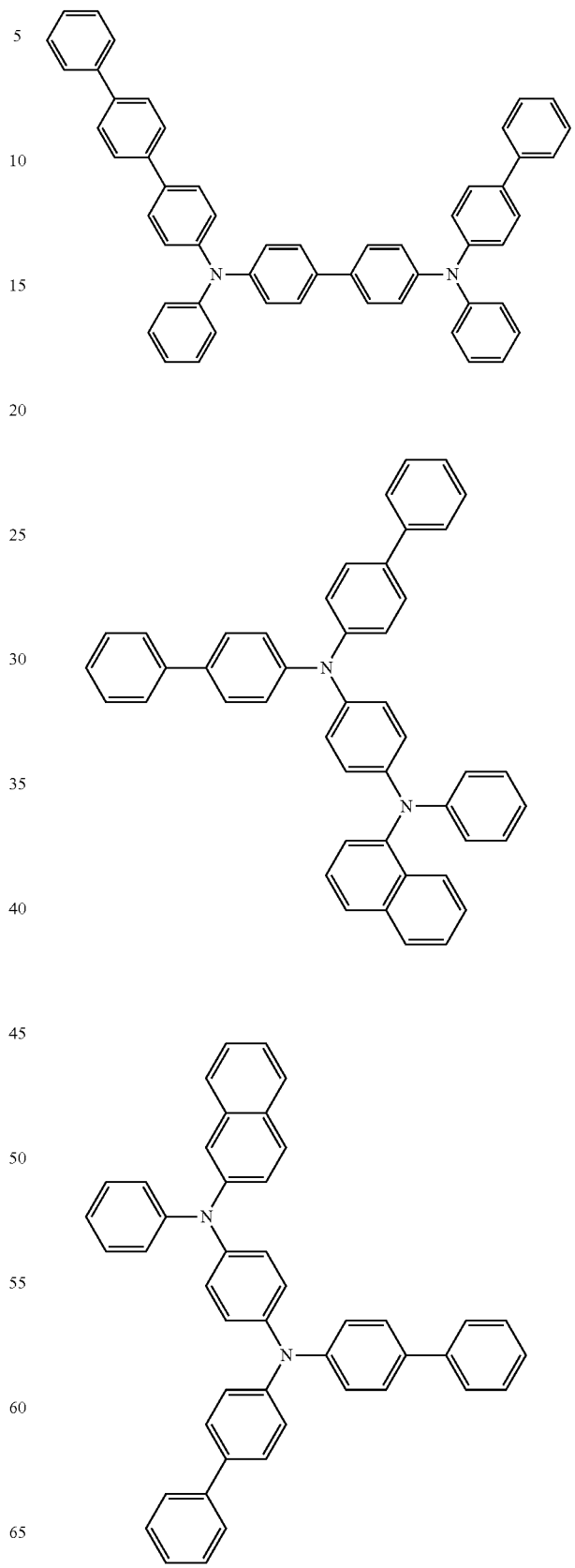

125
-continued
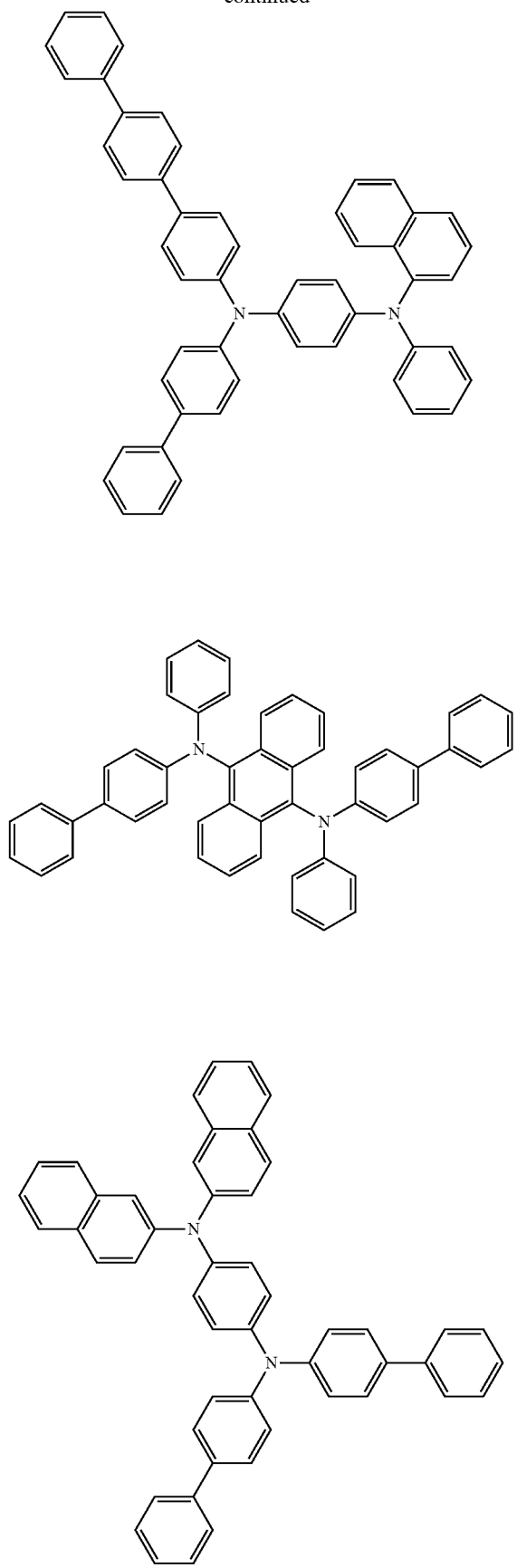
126
-continued
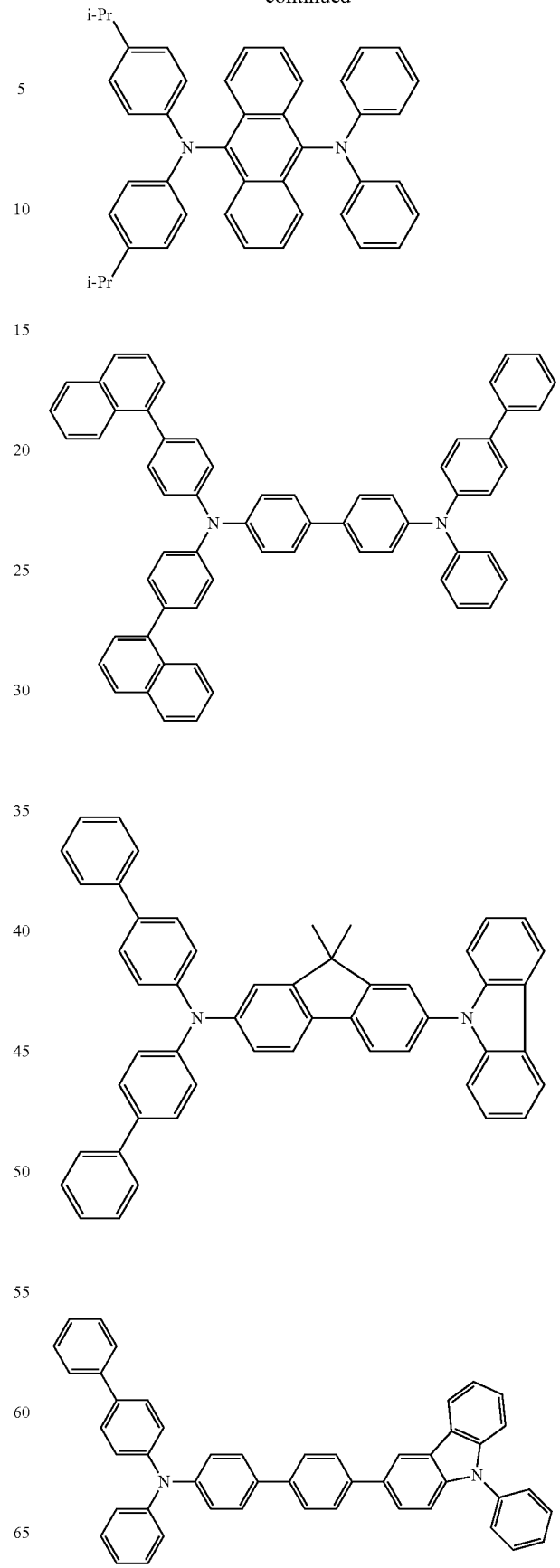

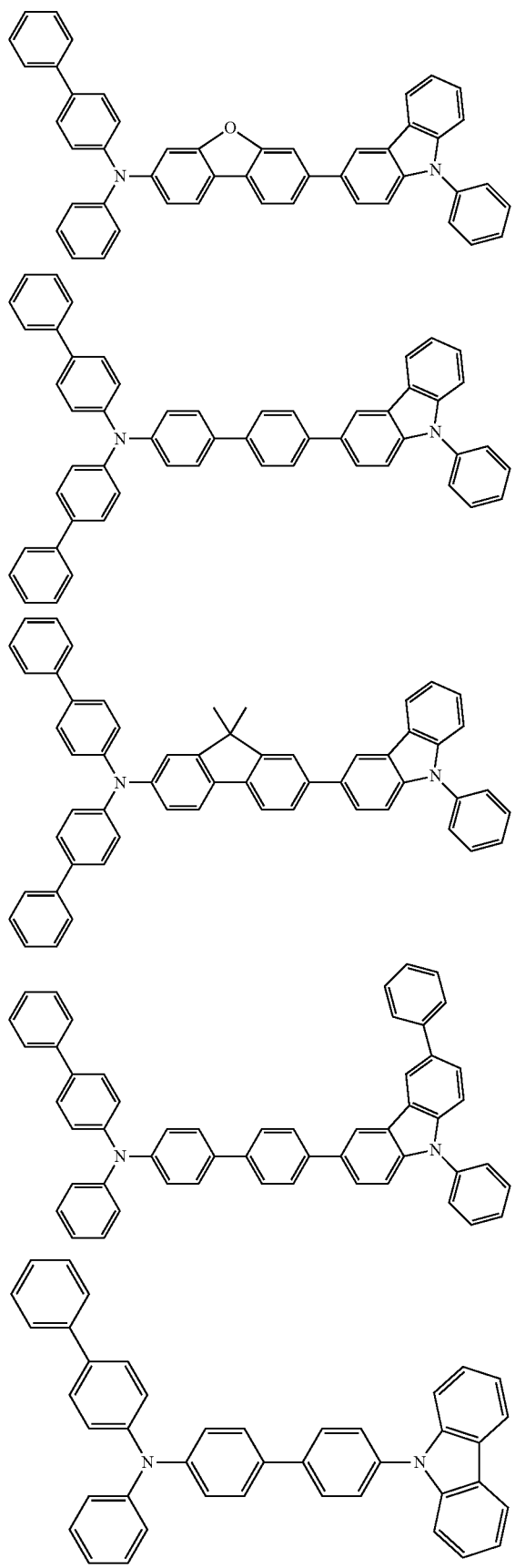
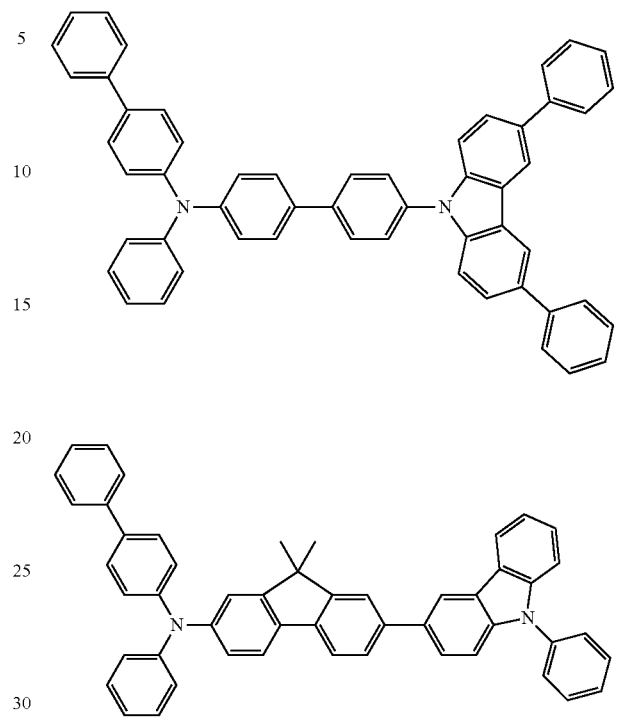
The aromatic amine represented by the formula (J) is also preferably used as the material for forming the hole transporting layer.
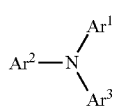
In the formula (J), each of Ar¹ to Ar³ is defined in the same manner as in the definition of Ar¹ to Ar⁴ of the formula (H). The specific examples of the compounds represented by the formula (J) are shown below, although not limited thereto.
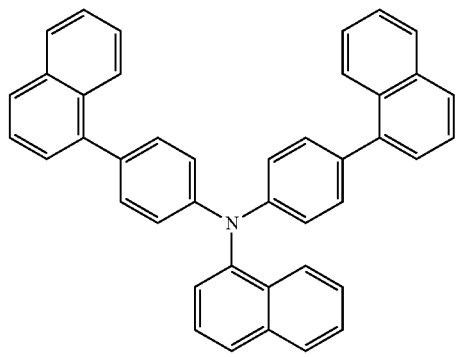

129
-continued
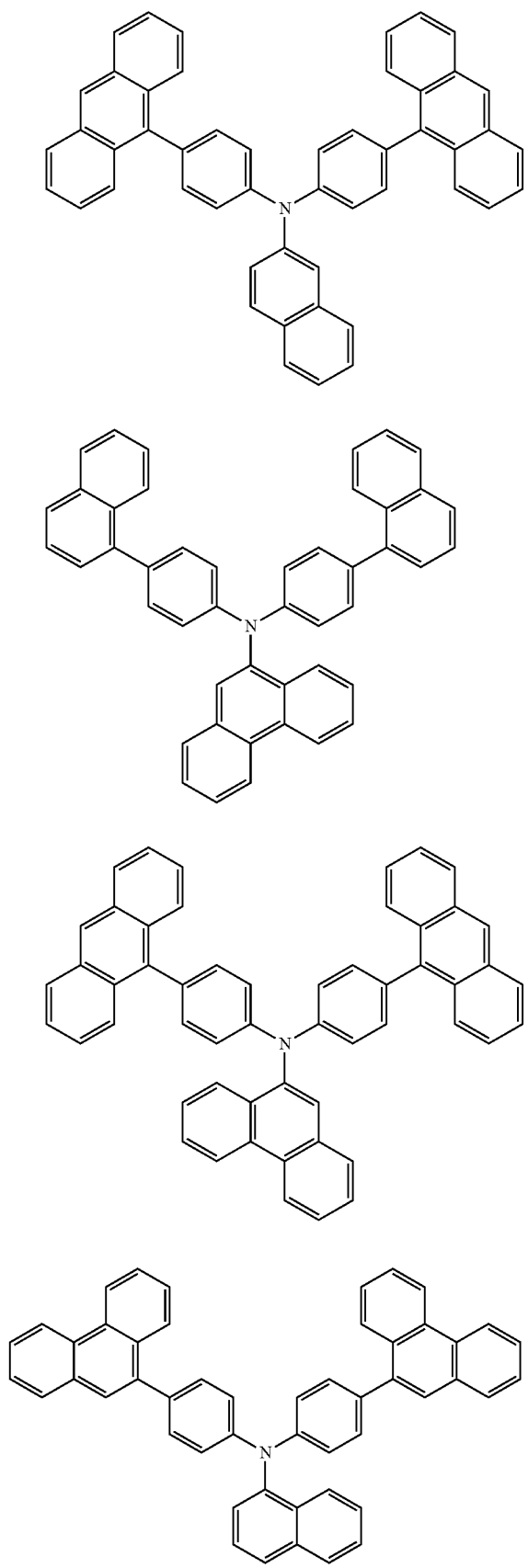
130
-continued
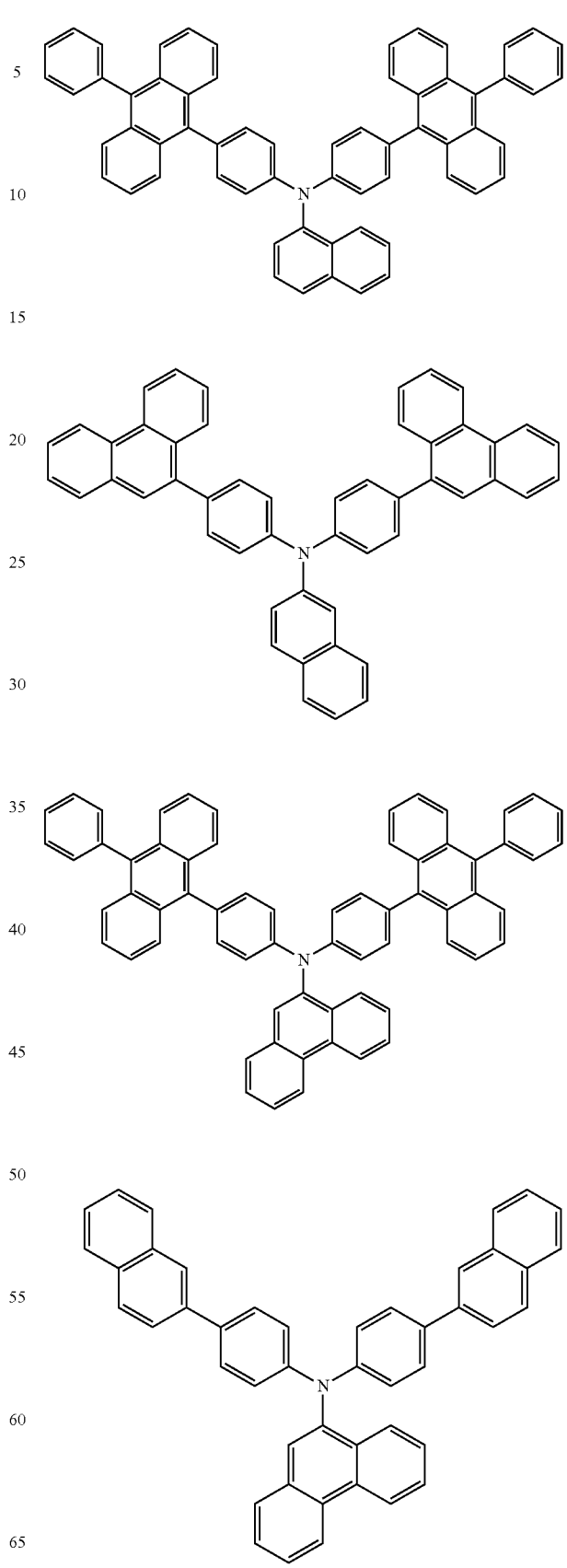

131
-continued
132
-continued
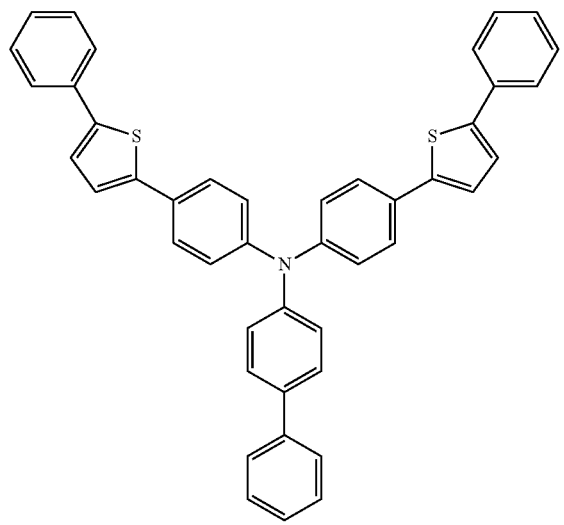
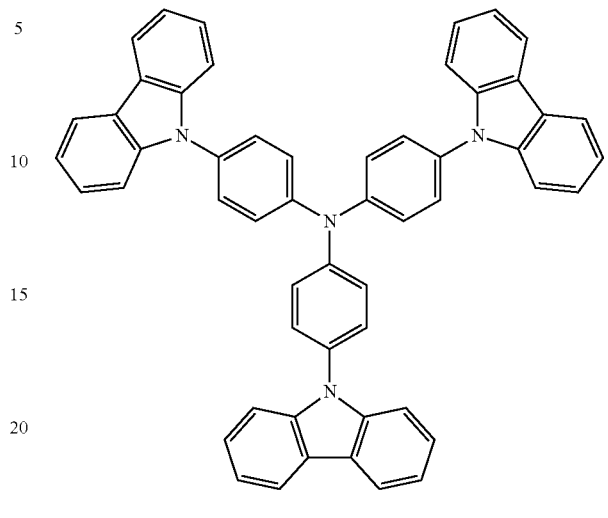
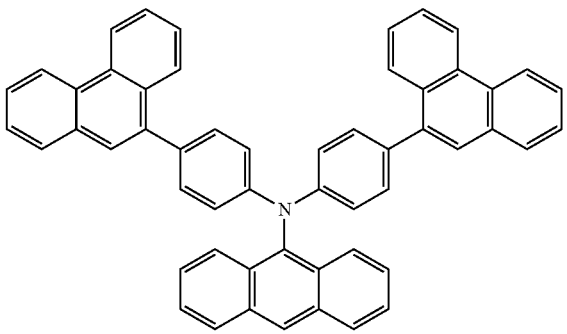
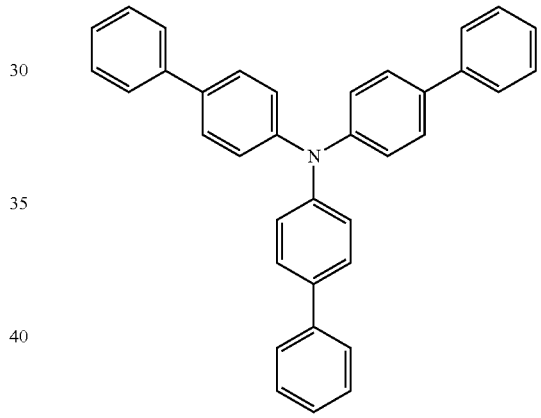
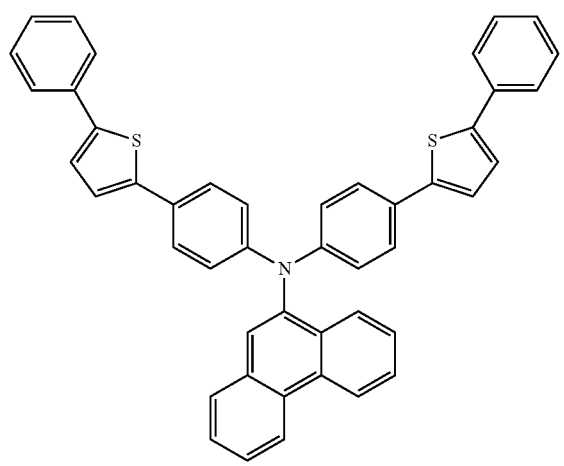
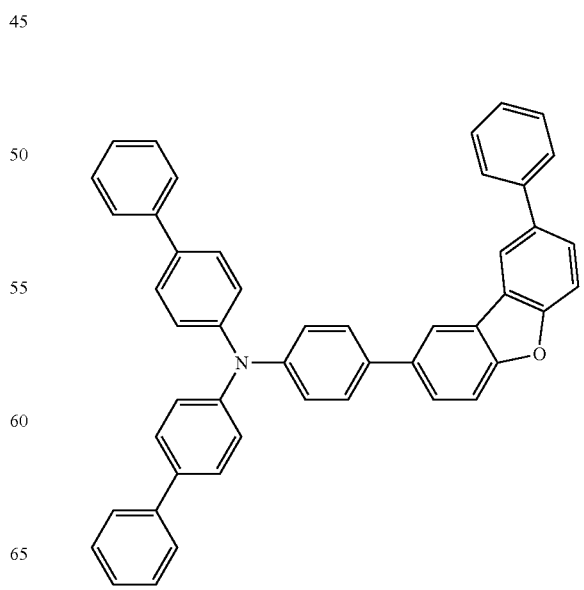

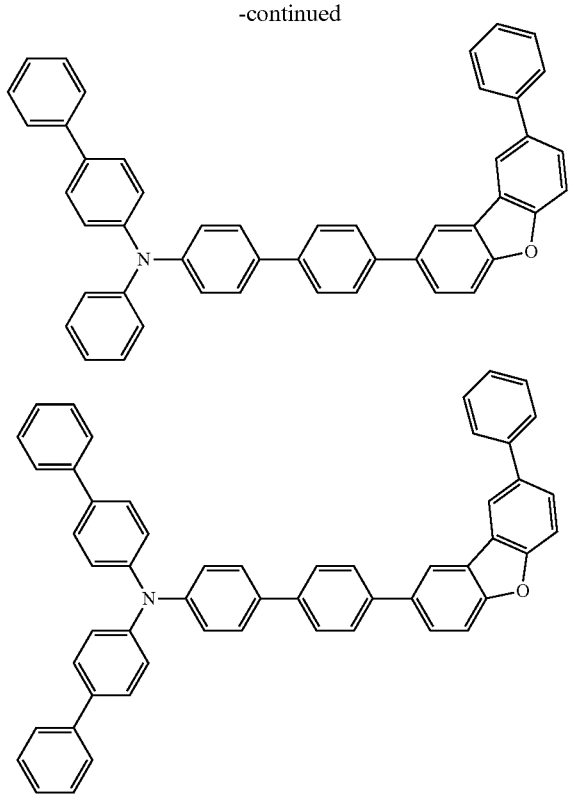

The hole transporting layer of the organic EL device of the invention may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is attached to the anode side of each of the hole transporting layer and the first hole transporting layer. With such a layer, it is expected that the driving voltage is lowered and the production cost is reduced.

The acceptor material is preferably a compound represented by the formula (K):

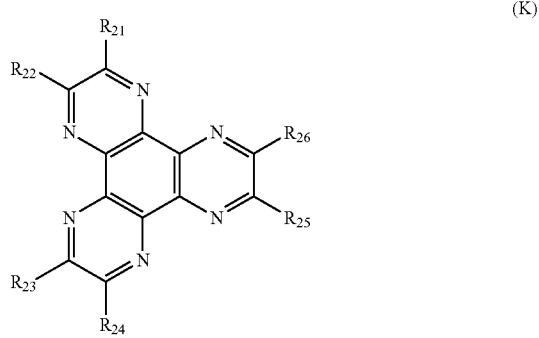

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include methyl group, ethyl group, n-propyl group, isopropyl group, n-butyl group, isobutyl group, t-butyl group, cyclopentyl group, and cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled by, as described in JP 3695714B, the doping (n) with a donor material or the doping (p) with an acceptor material.

A typical example of the n-doping is an electron transporting material doped with a metal, such as Li and Cs, and a typical example of the p-doping is a hole transporting material doped with an acceptor material such as, $F_4TCNQ$ (2,3,5,6-tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device of the invention is also usable as the material for the hole blocking layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T{}_d < E^T{}_{TB}$, the triplet excitons may move into other molecules if the energy difference ($\Delta E^T = E^T{}_{TB} - E^T{}_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

EXAMPLES

The present invention will be described in more detail with reference to the examples. However, it should be noted that the scope of the invention is not limited to the following examples.

Synthesis of Material for Organic EL Device

Synthesis Example 1

Synthesis of Compound H1

Synthesis Example (1-1)

Synthesis of Intermediate 1

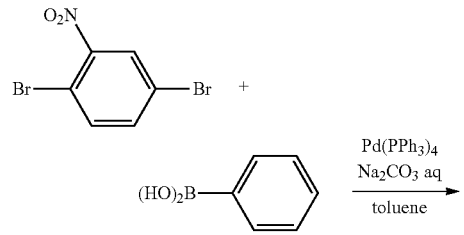

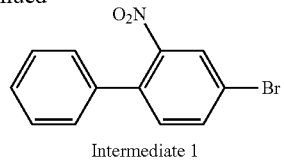

Intermediate 1

In argon stream, a mixture obtained by successively mixing 2-nitro-1,4-dibromobenzene (11.2 g, 40 mmol), phenylboronic acid (4.9 g, 40 mmol), tetrakis(triphenylphosphine)palladium (1.39 g, 1.2 mmol), toluene (120 mL), and a 2M aqueous solution of sodium carbonate (60 mL) was refluxed under heating for 8 h.

After cooling the reaction liquid to room temperature, the organic layer was separated and the organic solvent was removed from the organic layer by distillation under reduced pressure. The obtained residue was purified by a silica gel column chromatography to obtain the intermediate 1 (6.6 g, yield: 59%). The identification of the intermediate 1 was made by FD-MS (field desorption mass spectrometry) analysis.

Synthesis Example (1-2)

Synthesis of Intermediate 2

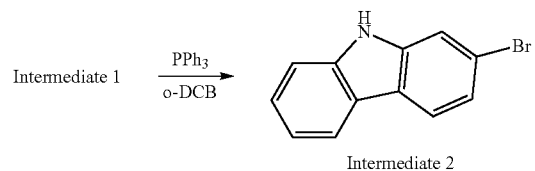 [SMILES: Brc1ccc2c(c1)[nH]c1ccccc12 ; "PPh3"]

Intermediate 2

In argon stream, a mixture obtained by successively mixing the intermediate 1 (6.6 g, 23.7 mmol), triphenylphosphine (15.6 g, 59.3 mmol), and o-dichlorobenzene (24 mL) was heated at 180° C. for 8 h.

After cooling the reaction liquid to room temperature, the reaction product was purified by a silica gel column chromatography to obtain the intermediate 2 (4 g, yield: 68%). The identification of the intermediate 2 was made by FD-MS (field desorption mass spectrometry) analysis.

Synthesis Example (1-3)

Synthesis of Intermediate 3

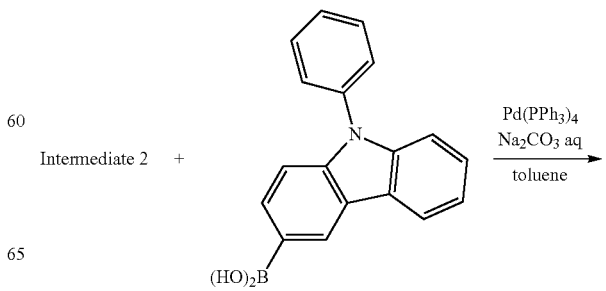

-continued

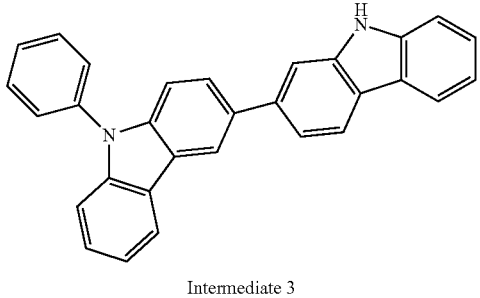

Intermediate 3

The procedure of Synthesis of Intermediate 1 was repeated except for using the intermediate 2 in place of 2-nitro-1,4-dibromobenzene and using 9-phenylcarbazole-3-ylboronic acid in place of phenylboronic acid. The obtained compound was identified as the intermediate 3 by FD-MS (field desorption mass spectrometry) analysis.

Synthesis Example (1-4)

Synthesis of Compound H1

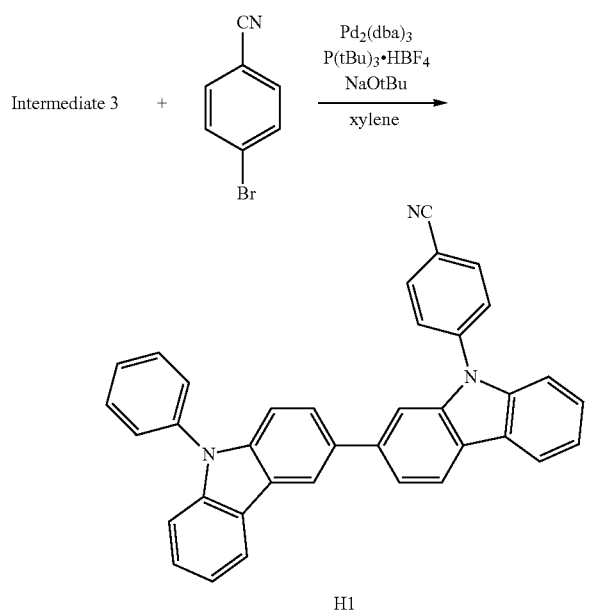

H1

In argon stream, a mixture obtained by successively mixing the intermediate 3 (1.6 g, 3.9 mmol), 4-bromobenzonitrile (0.71 g, 3.9 mmol), tris(dibenzylideneacetone)dipalladium (0.071 g, 0.078 mmol), tri-t-butylphosphonium tetrafluoroborate (0.091 g, 0.31 mmol), sodium t-butoxide (0.53 g, 5.5 mmol), and dry toluene (20 mL) was refluxed under heating for 8 h.

After cooling the reaction liquid to room temperature, the organic layer was separated and the organic solvent was removed from the organic layer by distillation under reduced pressure. The obtained residue was purified by a silica gel column chromatography to obtain 0.79 g of white solid (H1).

The obtained compound was measured for FD-MS (field desorption mass spectrometry), maximum ultraviolet absorption wavelength (UV(PhMe) λmax) in toluene, and maximum fluorescence wavelength (FL(PhMe, λex=300 nm) λmax) in toluene. The results are shown below.

FDMS: calcd. for $C_{37}H_{23}N_3$=509. found m/z=509 (M+)
(UV(PhMe) λmax: 324 nm
FL(PhMe, λex=300 nm) λmax: 376 nm Synthesis Example 2

Synthesis of Compound H2

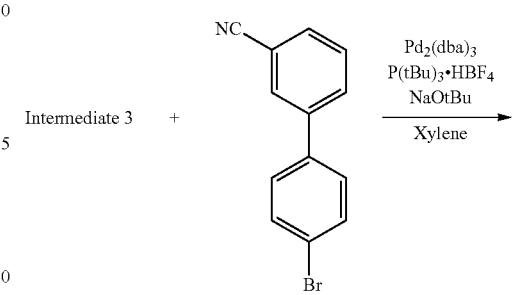

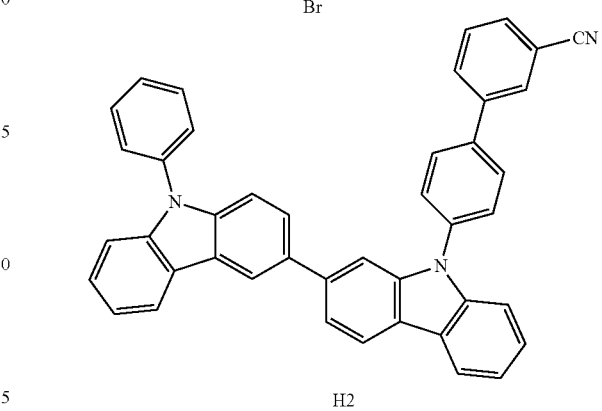

H2

The procedure of Synthesis of Compound H1 was repeated except for using 4'-bromobiphenyl-3-carbonitrile in place of 4-bromobenzonitrile.

The obtained compound was measured for FD-MS (field desorption mass spectrometry), maximum ultraviolet absorption wavelength ((UV(PhMe) λmax) in toluene, and maximum fluorescence wavelength (FL(PhMe, λex=300 nm) λmax) in toluene. The results are shown below.

FDMS: calcd. for $C_{43}H_{27}N_3$=585. found m/z=585 (M+)
(UV(PhMe) λmax: 322 nm
FL(PhMe, λex=300 nm) λmax: 375 nm Synthesis Example 3

Synthesis of Compound H3

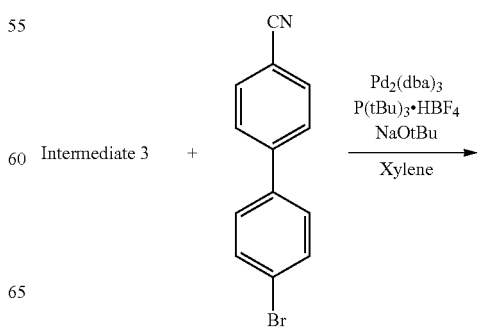

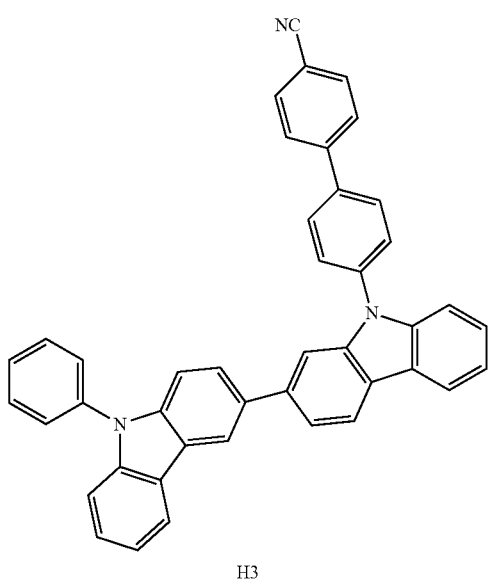

H3

The procedure of Synthesis of Compound H1 was repeated except for using 4'-bromobiphenyl-4-carbonitrile in place of 4-bromobenzonitrile.

The obtained compound was measured for FD-MS (field desorption mass spectrometry), maximum ultraviolet absorption wavelength ((UV(PhMe) λmax) in toluene, and maximum fluorescence wavelength (FL(PhMe, λex=300 nm) λmax) in toluene. The results are shown below.

FDMS: calcd. for $C_{43}H_{27}N_3$=585. found m/z=585 (M+)

(UV(PhMe) λmax: 324 nm

FL(PhMe, λex=300 nm) λmax: 393 nm

Synthesis Example 4

Synthesis of Compound H4

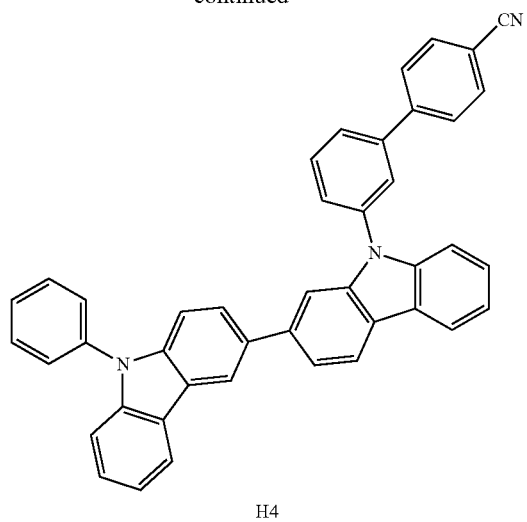

H4

The procedure of Synthesis of Compound H1 was repeated except for using 3'-bromobiphenyl-4-carbonitrile in place of 4-bromobenzonitrile.

The obtained compound was measured for FD-MS (field desorption mass spectrometry), maximum ultraviolet absorption wavelength ((UV(PhMe) λmax) in toluene, and maximum fluorescence wavelength (FL(PhMe, λex=300 nm) λmax) in toluene. The results are shown below.

FDMS: calcd. for $C_{43}H_{27}N_3$=585. found m/z=585 (M+)

(UV(PhMe) λmax: 322 nm

FL(PhMe, λex=300 nm) λmax: 376 nm

Synthesis Example 5

Synthesis of Compound H5

Synthesis Example (5-1)

Synthesis of Intermediate 4

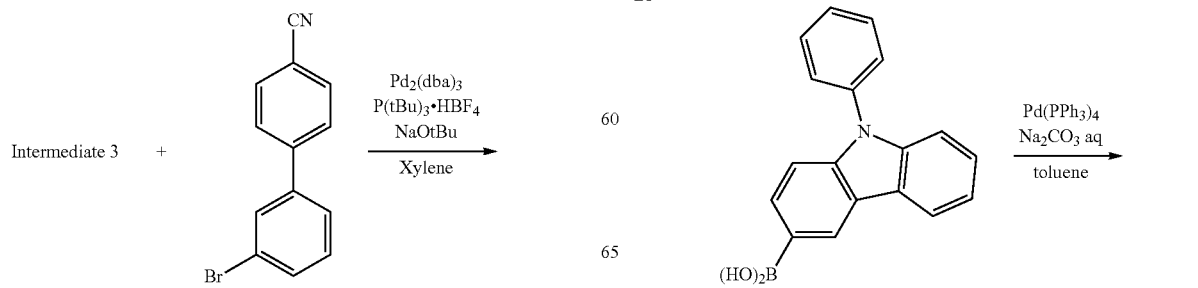

-continued

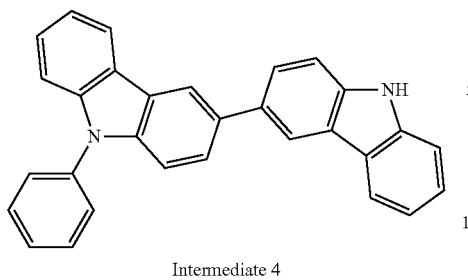

Intermediate 4

The procedure of Synthesis of Intermediate 1 was repeated except for using 3-bromocarbazole in place of 2-nitro-1,4-dibromobenzene and using 9-phenylcarbazole-3-ylboronic acid in place of phenylboronic acid.

The obtained compound was identified as the intermediate 4 by FD-MS (field desorption mass spectrometry) analysis.

Synthesis Example (5-2)

Synthesis of Compound H5

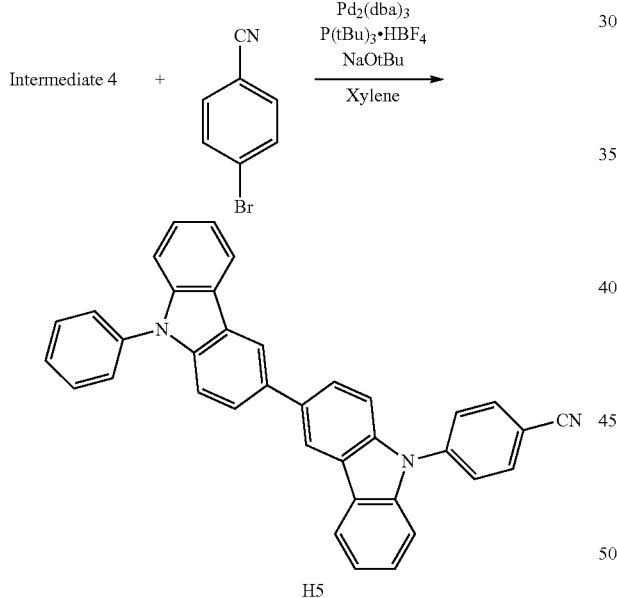

H5

The procedure of Synthesis of Compound H1 was repeated except for using the intermediate 4 in place of the intermediate 3.

The obtained compound was measured for FD-MS (field desorption mass spectrometry), maximum ultraviolet absorption wavelength ((UV(PhMe) λmax) in toluene, and maximum fluorescence wavelength (FL(PhMe, λex=300 nm) max) in toluene. The results are shown below.

FDMS: calcd. for $C_{37}H_{23}N_3$=509. found m/z=509 (M+)

(UV(PhMe) λmax: 339 nm

FL(PhMe, λex=300 nm) λmax: 404 nm

Synthesis Example 6

Synthesis of Compound H6

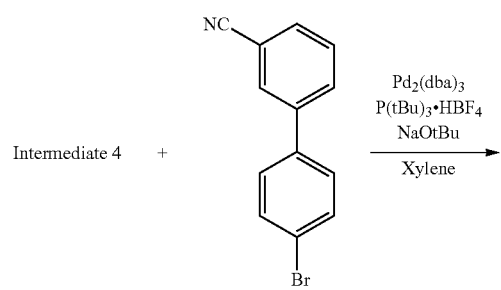

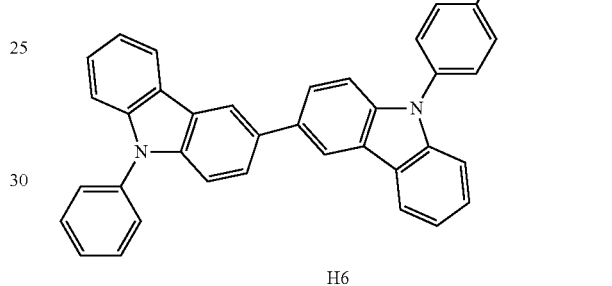

H6

The procedure of Synthesis of Compound H1 was repeated except for using 4'-bromobiphenyl-3-carbonitrile in place of 4-bromobenzonitrile and using the intermediate 4 in place of the intermediate 3.

The obtained compound was measured for FD-MS (field desorption mass spectrometry). The result is shown below.

FDMS: calcd. for $C_{43}H_{27}N_3$=585. found m/z=585 (M+)

Synthesis Example 7

Synthesis of Compound H7

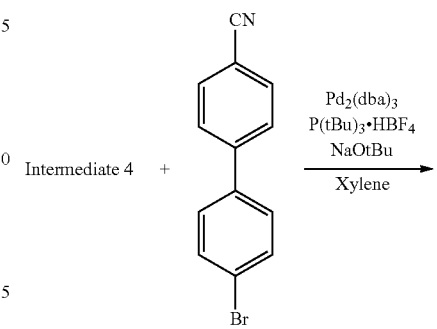

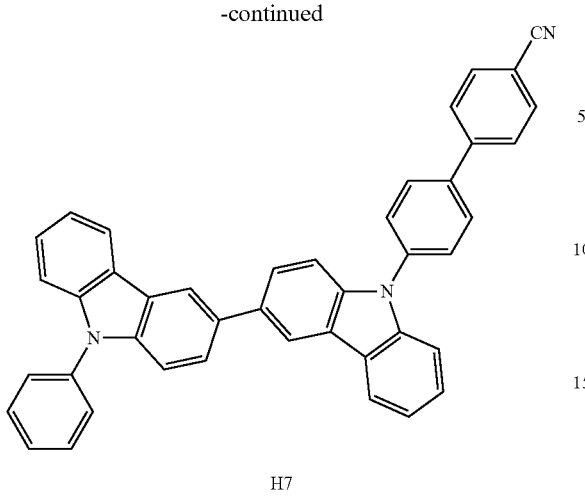

H7

The procedure of Synthesis of Compound H1 was repeated except for using 4'-bromobiphenyl-4-carbonitrile in place of 4-bromobenzonitrile and using the intermediate 4 in place of the intermediate 3.

The obtained compound was measured for FD-MS (field desorption mass spectrometry). The result is shown below.
FDMS: calcd. for $C_{43}H_{27}N_3$=585. found m/z=585 (M+)

Synthesis Example 8

Synthesis of Compound H8

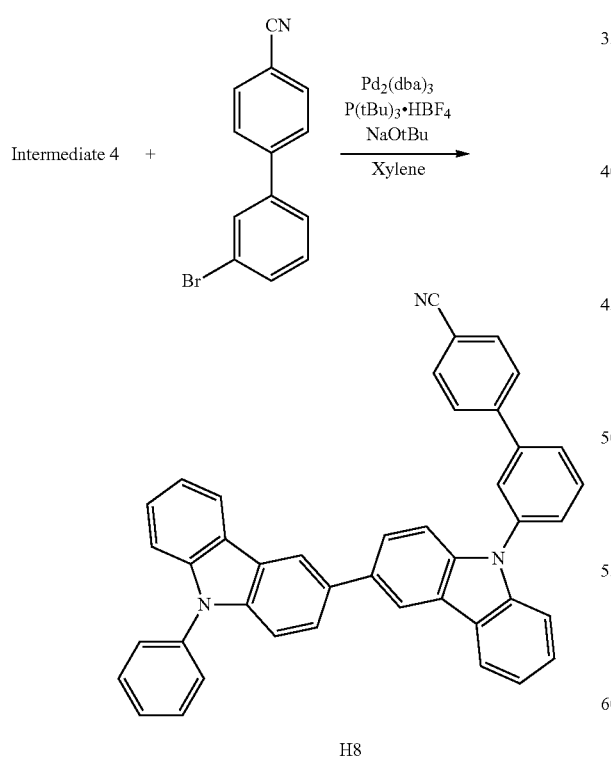

H8

The procedure of Synthesis of Compound H1 was repeated except for using 3'-bromobiphenyl-4-carbonitrile in place of 4-bromobenzonitrile and using the intermediate 4 in place of the intermediate 3.

The obtained compound was measured for FD-MS (field desorption mass spectrometry). The result is shown below.
FDMS: calcd. for $C_{43}H_{27}N_3$=585. found m/z=585 (M+)

Synthesis Example 9

Synthesis of Compound H9

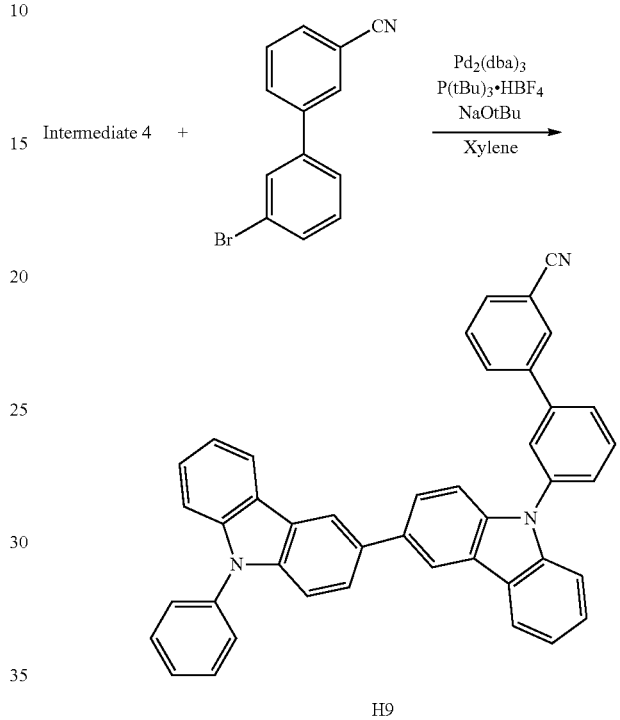

H9

The procedure of Synthesis of Compound H1 was repeated except for using 3'-bromobiphenyl-3-carbonitrile in place of 4-bromobenzonitrile and using the intermediate 4 in place of the intermediate 3.

The obtained compound was measured for FD-MS (field desorption mass spectrometry). The result is shown below.
FDMS: calcd. for $C_{43}H_{27}N_3$=585. found m/z=585 (M+)

Synthesis Example 10

Synthesis of Compound H10

Synthesis Example (10-1)

Synthesis of Intermediate 5

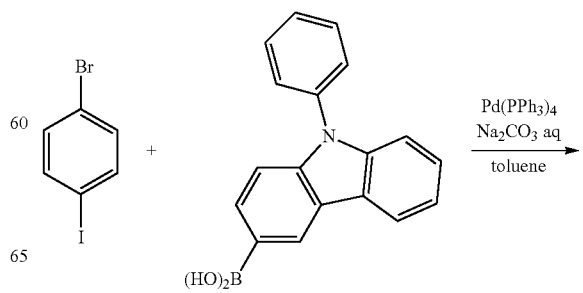

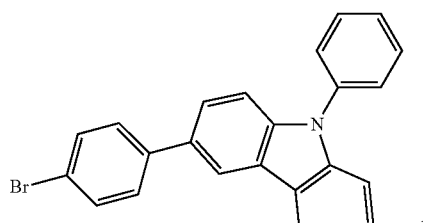

Intermediate 5

The procedure of Synthesis of Intermediate 1 was repeated except for using 1-bromo-4-iodobenzene in place of 2-nitro-1,4-dibromobenzene and using 9-phenylcarbazole-3-ylboronic acid in place of phenylboronic acid.

The obtained compound was identified as the intermediate 5 by FD-MS (field desorption mass spectrometry) analysis.

Synthesis Example (10-2)

Synthesis of Intermediate 6

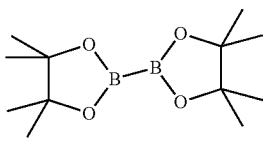

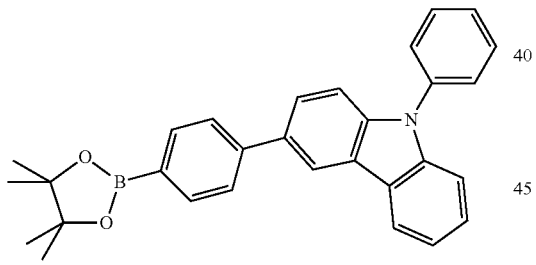

Intermediate 6

In argon stream, a mixture obtained by successively mixing the intermediate 5 (10 g, 25 mmol), bis(pinacolato)diboron (8.3 g, 33 mmol), dichloromethane adduct of [1,1'-bis(diphenylphosphino)ferrocene]palladium(II) dichloride (0.62 g, 0.75 mmol), potassium acetate (7.4 g, 75 mmol), and N,N-dimethylformamide (170 mL) was refluxed under heating for 8 h.

After cooling the reaction liquid to room temperature, the organic layer was separated and the organic solvent was removed from the organic layer by distillation under reduced pressure. The obtained residue was purified by a silica gel column chromatography to obtain the intermediate 6 (10 g, yield: 91%). The identification of the intermediate 6 was made by FD-MS (field desorption mass spectrometry) analysis.

Synthesis Example (10-3)

Synthesis of Intermediate 7

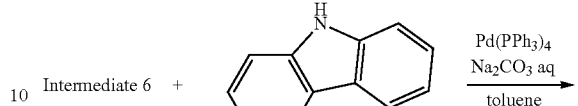

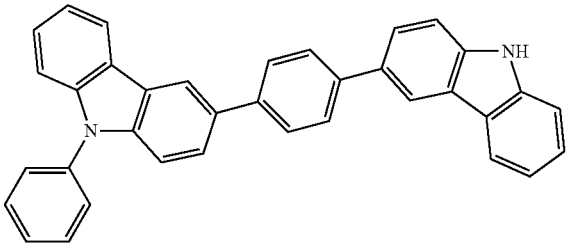

Intermediate 7

The procedure of Synthesis of Intermediate 1 was repeated except for using 3-bromocarbazole in place of 2-nitro-1,4-dibromobenzene and using the intermediate 6 in place of phenylboronic acid. The obtained compound was identified as the intermediate 7 by FD-MS (field desorption mass spectrometry) analysis.

Synthesis Example (10-4)

Synthesis of H10

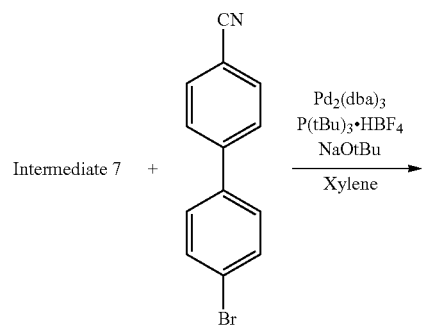

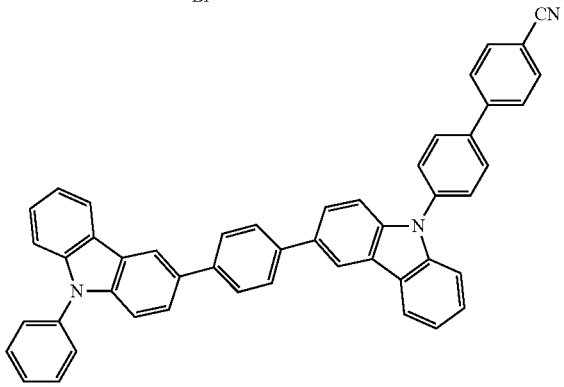

H10

The procedure of Synthesis of Compound H1 was repeated except for using 4'-bromobiphenyl-4-carbonitrile in place of 4-bromobenzonitrile and using the intermediate 7 in place of the intermediate 3.

The obtained compound was measured for FD-MS (field desorption mass spectrometry). The result is shown below.

FDMS: calcd. for $C_{49}H_{31}N_3$=661. found m/z=661 (M+)

Synthesis Example 11

Synthesis of Compound H11

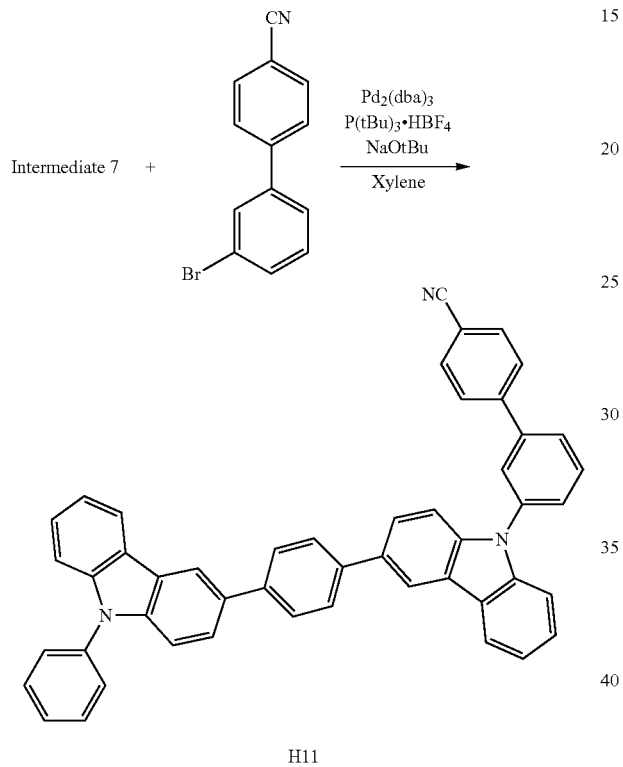

H11

The procedure of Synthesis of Compound H1 was repeated except for using 3'-bromobiphenyl-4-carbonitrile in place of 4-bromobenzonitrile and using the intermediate 7 in place of the intermediate 3.

The obtained compound was measured for FD-MS (field desorption mass spectrometry). The result is shown below.

FDMS: calcd. for $C_{49}H_{31}N_3$=661. found m/z=661 (M+)

Synthesis Example 12

Synthesis of Compound H12

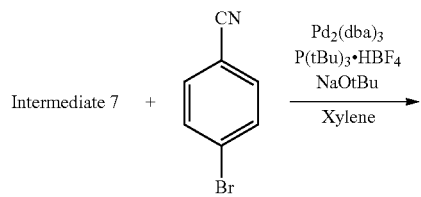

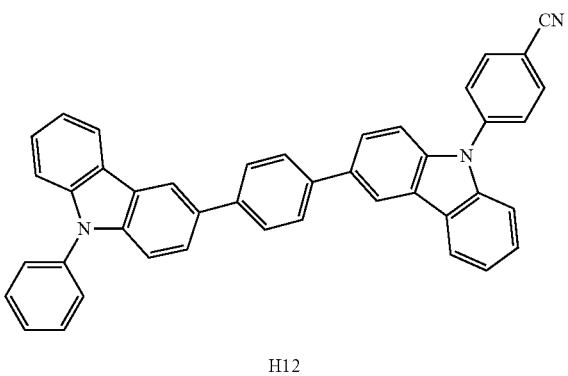

H12

The procedure of Synthesis of Compound H1 was repeated except for using the intermediate 7 in place of the intermediate 3.

The obtained compound was measured for FD-MS (field desorption mass spectrometry). The result is shown below.

FDMS: calcd. for $C_{43}H_{27}N_3$=585. found m/z=585 (M+)

Synthesis Example 13

Synthesis of Compound H13

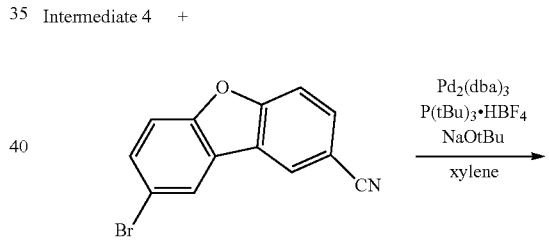

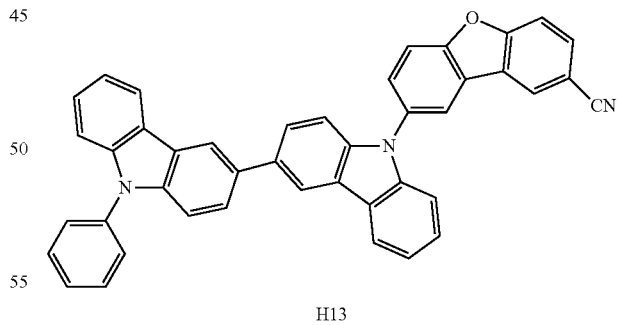

H13

The procedure of Synthesis of Compound H1 was repeated except for using 2-bromo-8-cyanodibenzofuran in place of 4-bromobenzonitrile and using the intermediate 4 in place of the intermediate 3.

The obtained compound was measured for FD-MS (field desorption mass spectrometry). The result is shown below.

FDMS: calcd. for $C_{43}H_{25}N_3O$=599. found m/z=599 (M+)

Synthesis Example 14

Synthesis of Compound H14

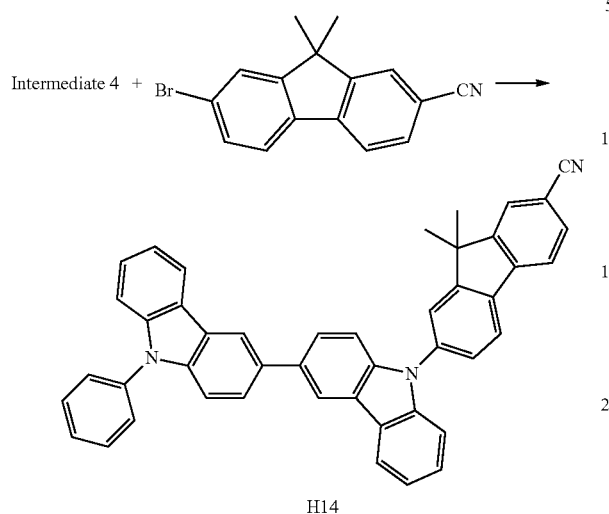

H14

The procedure of Synthesis of Compound H1 was repeated except for using 2-bromo-7-cyano-9,9-dimethylfluorene in place of 4-bromobenzonitrile and using the intermediate 4 in place of the intermediate 3.

The obtained compound was measured for FD-MS (field desorption mass spectrometry). The result is shown below.

FDMS: calcd. for $C_{46}H_{31}N_3$=625. found m/z=625 (M+)

Synthesis Example 15

Synthesis of Compound H15

Synthesis Example (15-1)

Synthesis of Intermediate 8

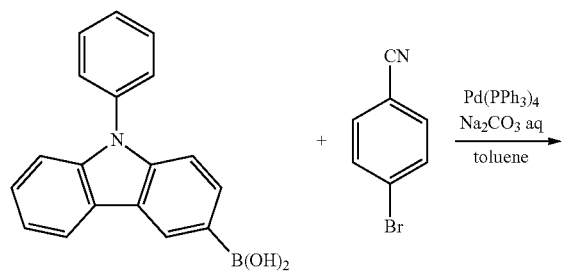

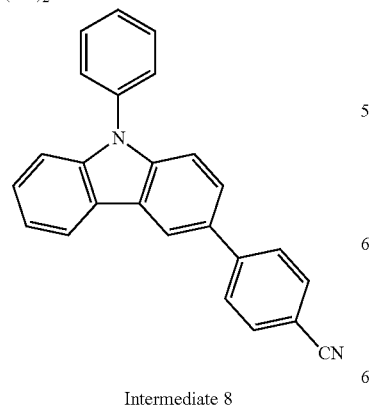

Intermediate 8

The procedure of Synthesis of Intermediate 1 was repeated except for using 4-bromobenzonitrile in place of 2-nitro-1,4-dibromobenzene and using 9-phenylcarbazole-3-ylboronic acid in place of phenylboronic acid.

The obtained compound was identified as the intermediate 8 by FD-MS (field desorption mass spectrometry) analysis.

Synthesis Example (15-2)

Synthesis of Intermediate 9

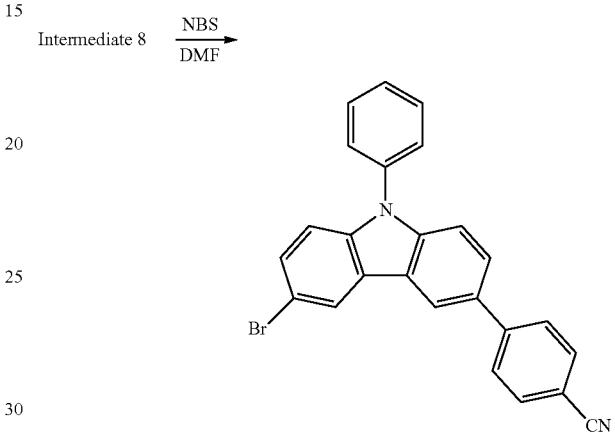

Intermediate 9

In argon stream, a mixture obtained by successively mixing N,N-dimethylformamide (80 mL), the intermediate 8 (5.6 g, 16.3 mmol), and N-bromosuccinimide (3.5 g, 19.5 mmol) was stirred at 0° C. for 8 h.

After returning the temperature to room temperature, the reaction liquid was added with distilled water and then filtered. The obtained solid was purified by silica gel column chromatography to obtain the intermediate 9 (6.2 g, yield: 90%). The identification of the intermediate 9 was made by FD-MS (field desorption mass spectrometry) analysis.

Synthesis Example (15-3)

Synthesis of Compound H15

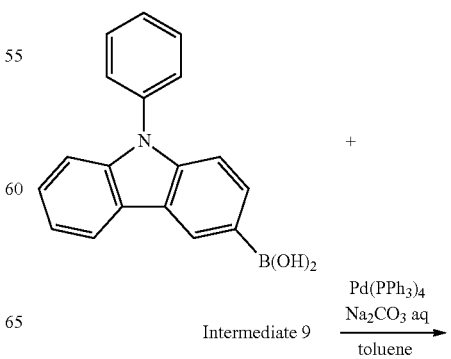

Intermediate 9

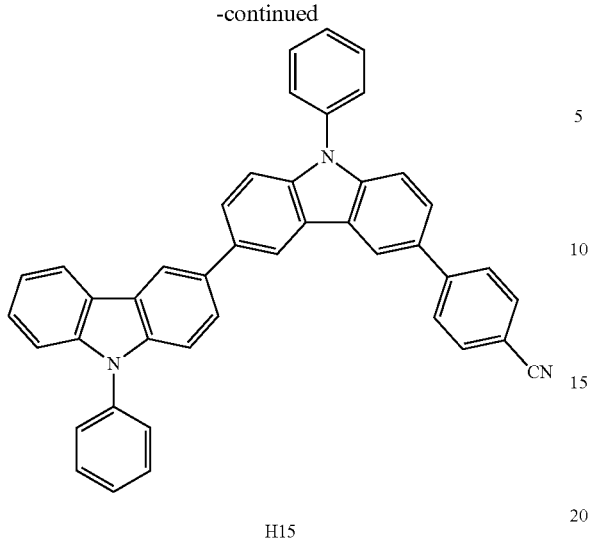

H15

The procedure of Synthesis of Intermediate 1 was repeated except for using the intermediate 9 in place of 2-nitro-1,4-dibromobenzene and using 9-phenylcarbazole-3-ylboronic acid in place of phenylboronic acid.

The obtained compound was measured for FD-MS (field desorption mass spectrometry). The result is shown below.

FDMS: calcd. for $C_{43}H_{27}N_3$=585. found m/z=585 (M+)

Synthesis Example 16

Synthesis of Compound H16

Synthesis Example (16-1)

Synthesis of Intermediate 10

Intermediate 2 →(PdCl$_2$(dppf)·CH$_2$Cl$_2$, KOAc, DMF(0.15M), 80° C.)→ Intermediate 10

The procedure of Synthesis of Intermediate 6 was repeated except for using the intermediate 2 in place of the intermediate 5. The obtained compound was identified as the intermediate 10 by FD-MS (field desorption mass spectrometry) analysis.

Synthesis Example (16-2)

Synthesis of Intermediate 11

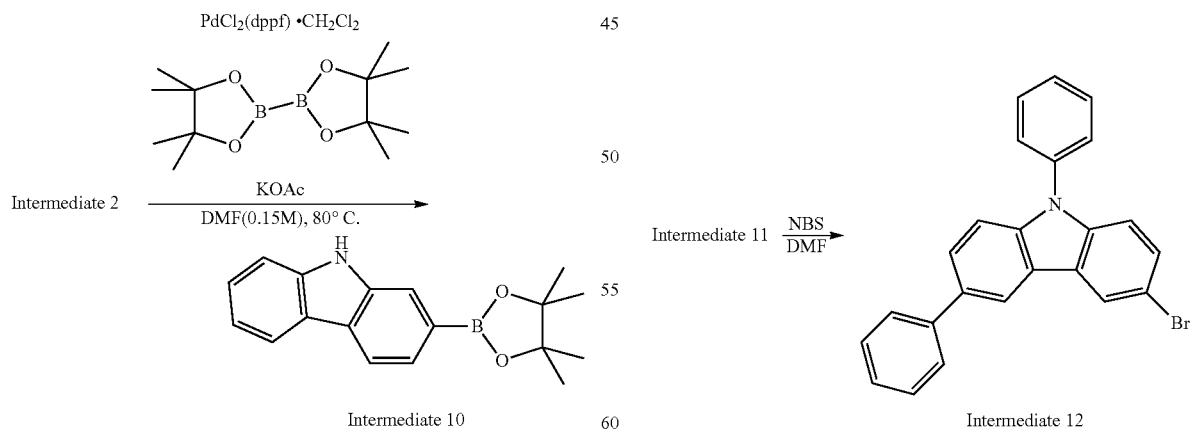

Intermediate 11

The procedure of Synthesis of Intermediate 1 was repeated except for using 3-bromo-9-phenylcarbazole in place of 2-nitro-1,4-dibromobenzene. The obtained compound was identified as the intermediate 11 by FD-MS (field desorption mass spectrometry) analysis.

Synthesis Example (16-3)

Synthesis of Intermediate 12

Intermediate 11 →(NBS/DMF)→ Intermediate 12

The procedure of Synthesis of Intermediate 9 was repeated except for using the intermediate 11 in place of the intermediate 8. The obtained compound was identified as the intermediate 12 by FD-MS (field desorption mass spectrometry) analysis.

Synthesis Example (16-4)

Synthesis of Intermediate 13

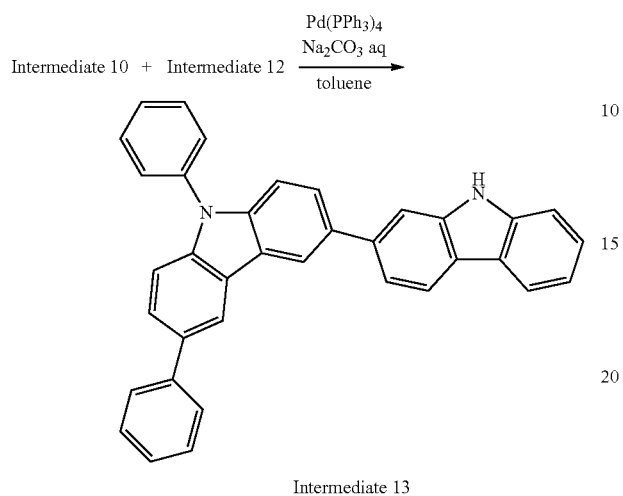

Intermediate 13

The procedure of Synthesis of Intermediate 1 was repeated except for using the intermediate 12 in place of 2-nitro-1,4-dibromobenzene and using the intermediate 10 in place of phenylboronic acid. The obtained compound was identified as the intermediate 13 by FD-MS (field desorption mass spectrometry) analysis.

Synthesis Example (16-5)

Synthesis of Compound H16

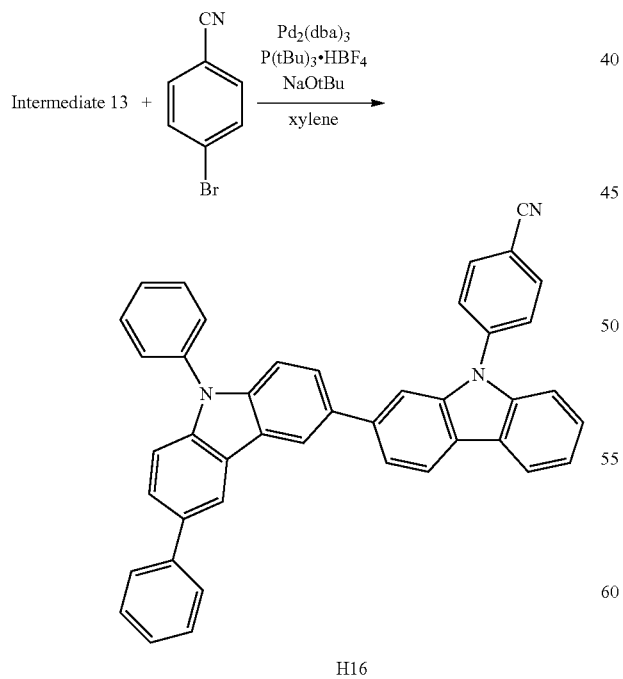

H16

The procedure of Synthesis of Compound H1 was repeated except for using the intermediate 13 in place of the intermediate 3.

The obtained compound was measured for FD-MS (field desorption mass spectrometry), maximum ultraviolet absorption wavelength λmax in toluene, and maximum fluorescence wavelength in toluene. The results are shown below.

FDMS: calcd. for $C_{43}H_{27}N_3$=585. found m/z=585 (M+)
(UV(PhMe) λmax: 310 nm
FL(PhMe, λex=300 nm) λmax: 379 nm

Synthesis Example 17

Synthesis of Compound H17

Synthesis Example (17-1)

Synthesis of Intermediate 14

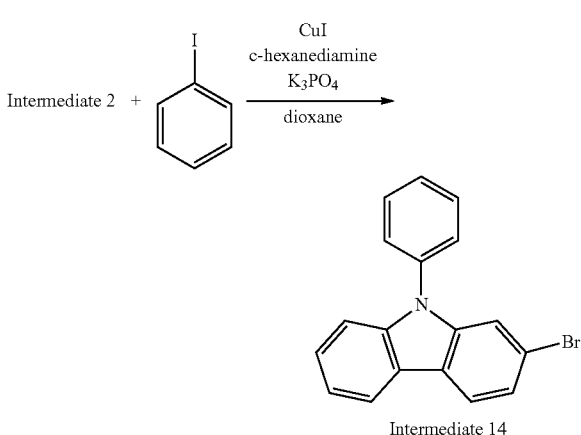

Intermediate 14

In argon stream, a mixture obtained by successively mixing the intermediate 2 (20 g, 81 mmol), iodobenzene (18.1 g, 89 mmol), copper iodide (1.5 g, 8 mmol), tripotassium phosphate (34.5 g, 163 mmol), dry dioxane (100 mL), and cyclohexanediamine (1.8 g, 16 mmol) was stirred at 80° C. for 8 h.

After cooling the reaction liquid to room temperature, the organic layer was separated and the organic solvent was removed from the organic layer by distillation under reduced pressure. The obtained residue was purified by a silica gel column chromatography to obtain the intermediate 14 (18.3 g, yield: 70%). The identification of the intermediate 14 was made by FD-MS (field desorption mass spectrometry) analysis.

Synthesis Example (17-2)

Synthesis of Intermediate 15

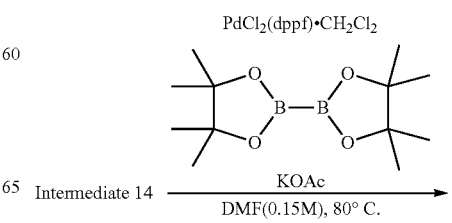

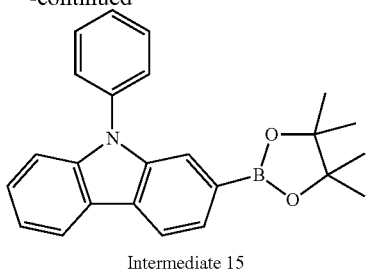

Intermediate 15

The procedure of Synthesis of Intermediate 6 was repeated except for using the intermediate 14 in place of the intermediate 5. The obtained compound was identified as the intermediate 15 by FD-MS (field desorption mass spectrometry) analysis.

Synthesis Example (17-3)

Synthesis of Intermediate 16

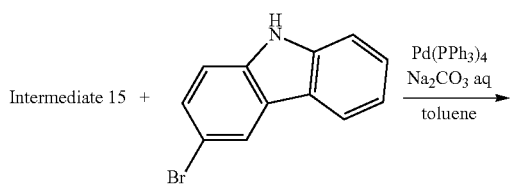

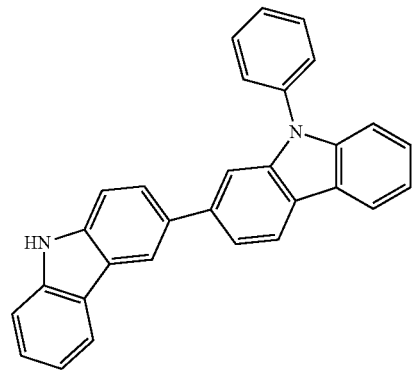

Intermediate 16

The procedure of Synthesis of Intermediate 1 was repeated except for using 3-bromocarbazole in place of 2-nitro-1,4-dibromobenzene and using the intermediate 15 in place of phenylboronic acid. The obtained compound was identified as the intermediate 16 by FD-MS (field desorption mass spectrometry) analysis.

Synthesis Example (17-4)

Synthesis of Compound H17

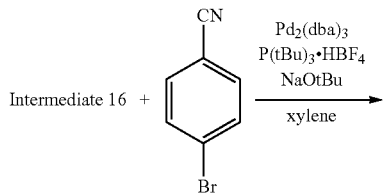

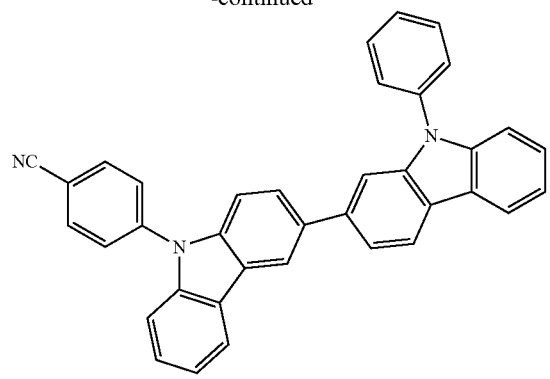

H17

The procedure of Synthesis of Compound H1 was repeated except for using the intermediate 16 in place of the intermediate 3.

The obtained compound was measured for FD-MS (field desorption mass spectrometry), maximum ultraviolet absorption wavelength λmax in toluene, and maximum fluorescence wavelength in toluene. The results are shown below.

FDMS: calcd. for $C_{37}H_{23}N_3$=509. found m/z=509 (M+)

(UV(PhMe) λmax: 324 nm

FL(PhMe, λex=300 nm) λmax: 376 nm

Synthesis Example 18

Synthesis of Compound H18

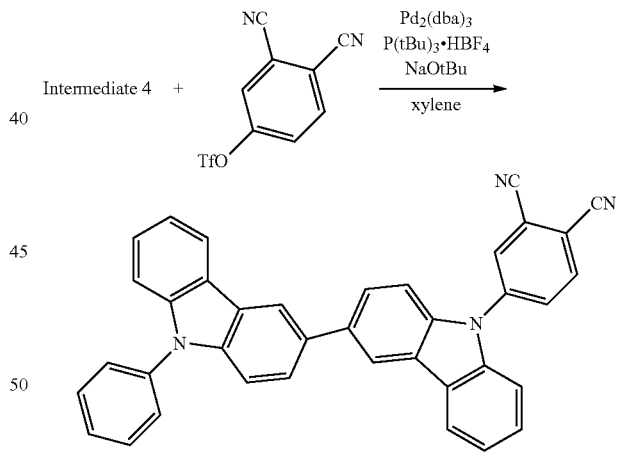

H18

The procedure of Synthesis of Compound H1 was repeated except for using the intermediate 4 in place of the intermediate 3 and using 3,4-dicyanophenyl trifluoromethanesulfonate in place of 4-bromobenzonitrile.

The obtained compound was measured for FD-MS (field desorption mass spectrometry), maximum ultraviolet absorption wavelength λmax in toluene, and maximum fluorescence wavelength in toluene. The results are shown below.

FDMS: calcd. for $C_{38}H_{22}N_4$=534. found m/z=534 (M+)

(UV(PhMe) λmax: 377 nm

FL(PhMe, λex=350 nm): λmax: 488 nm

Synthesis Example 19

Synthesis of Compound H19

Synthesis Example (19-1)

Synthesis of Intermediate 17

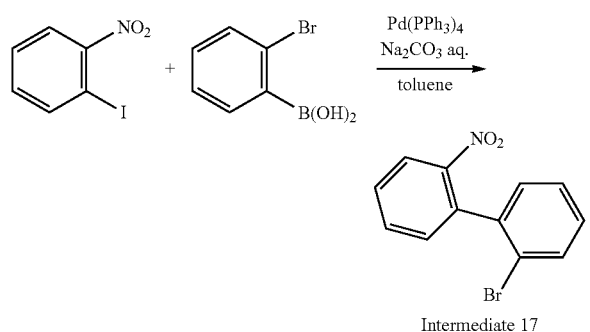

Intermediate 17

The procedure of Synthesis of Intermediate 1 was repeated except for using 2-iodonitrobenzene in place of 2-nitro-1,4-dibromobenzene and using 2-bromophenylboronic acid in place of phenylboronic acid. The obtained compound was identified as the intermediate 17 by FD-MS (field desorption mass spectrometry) analysis.

Synthesis Example (19-2)

Synthesis of Intermediate 18

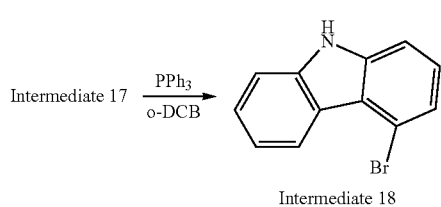 [SMILES: Brc1cccc2[nH]c3ccccc3c12 ; "PPh3"]

Intermediate 18

The procedure of Synthesis of Intermediate 2 was repeated except for using the intermediate 17 in place of the intermediate 1. The obtained compound was identified as the intermediate 18 by FD-MS (field desorption mass spectrometry) analysis.

Synthesis Example (19-3)

Synthesis of Intermediate 19

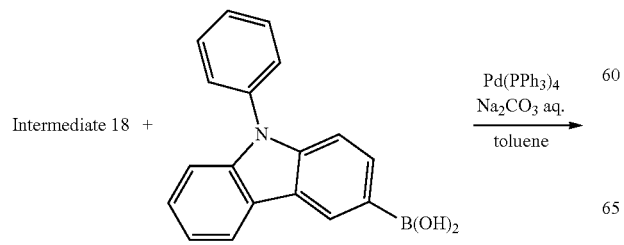

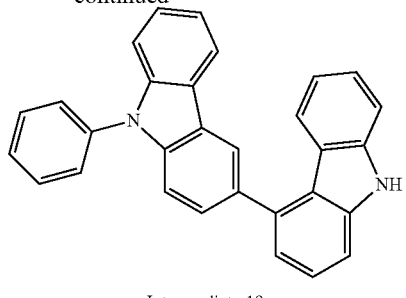

Intermediate 19

The procedure of Synthesis of Intermediate 3 was repeated except for using the intermediate 18 in place of the intermediate 2. The obtained compound was identified as the intermediate 19 by FD-MS (field desorption mass spectrometry) analysis.

Synthesis Example (19-4)

Synthesis of Compound H19

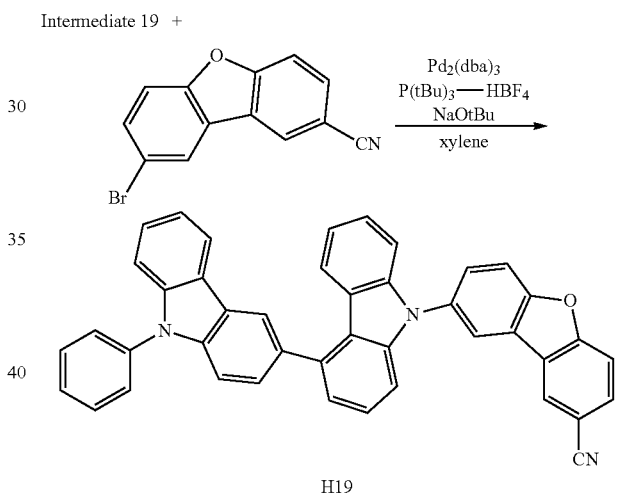

H19

The procedure of Synthesis of Compound H13 was repeated except for using the intermediate 19 in place of the intermediate 4. The obtained compound was identified as the compound H19 by FD-MS (field desorption mass spectrometry) analysis.

FDMS: calcd. for $C_{43}H_{25}N_3O$=599. found m/z=599 (M+)

Synthesis Example 20

Synthesis of Compound H20

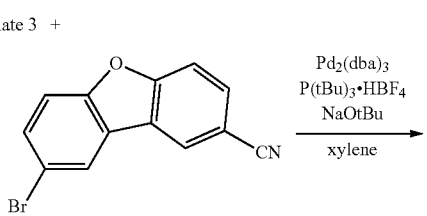

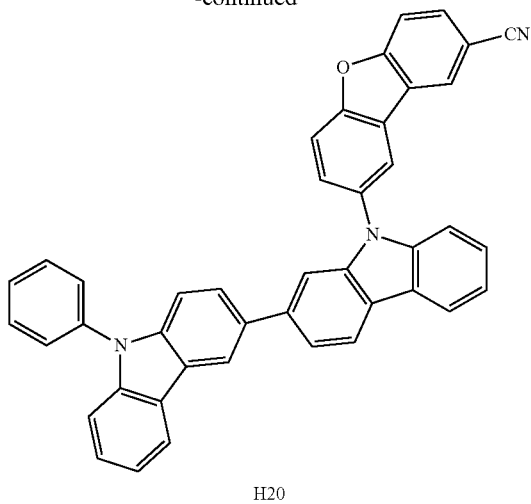

H20

The procedure of Synthesis of Compound H1 was repeated except for using 2-bromo-8-cyanodibenzofuran in place of 4-bromobenzonitrile. The obtained compound was measured for FD-MS (field desorption mass spectrometry). The result is shown below.

FDMS: calcd. for $C_{43}H_{25}N_3O=599$. found m/z=599 (M+)

Synthesis Example 21

Synthesis of Compound H21

Intermediate 3 +

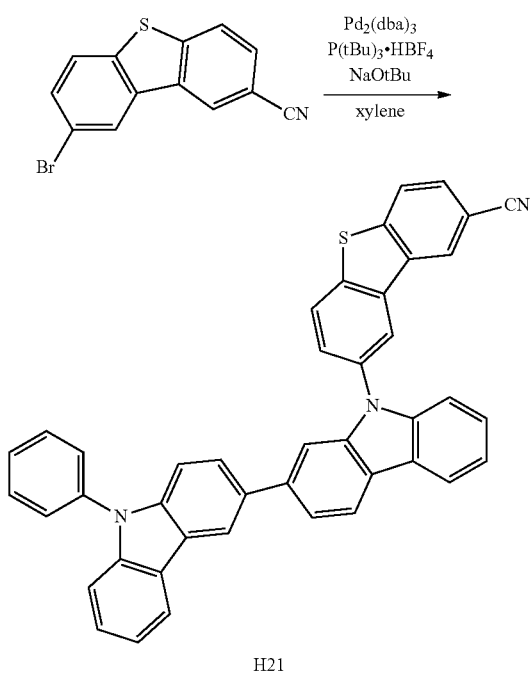

H21

The procedure of Synthesis of Compound H1 was repeated except for using 2-bromo-8-cyanodibenzothiophene in place of 4-bromobenzonitrile. The obtained compound was measured for FD-MS (field desorption mass spectrometry). The result is shown below.

FDMS: calcd. for $C_{43}H_{25}N_3S=615$. found m/z=615 (M+)

Synthesis Example 22

Synthesis of Compound H22

Intermediate 4 +

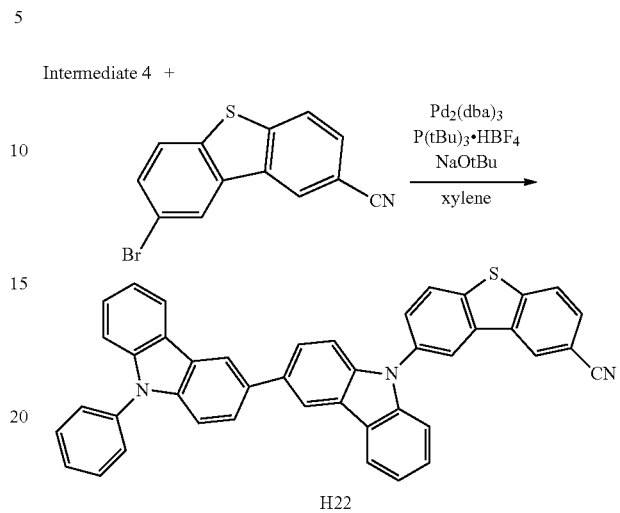

H22

The procedure of Synthesis of Compound H1 was repeated except for using 2-bromo-8-cyanodibenzothiophene in place of 4-bromobenzonitrile and using the intermediate 4 in place of the intermediate 3. The obtained compound was measured for FD-MS (field desorption mass spectrometry). The result is shown below.

FDMS: calcd. for $C_{43}H_{25}N_3S=615$. found m/z=615 (M+)

Production of Organic EL Device and Evaluation of Emission Performance

Example 1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate was mounted to a substrate holder of a vacuum vapor deposition apparatus. The electron accepting compound C-1 (acceptor) shown below was vapor-deposited so as to cover the transparent electrode to form a compound C-1 film with a thickness of 5 nm. On the compound C-1 film, a first hole transporting material (aromatic amine derivative (compound X1) shown below) was vapor-deposited to form a first hole transporting layer with a thickness of 65 nm. Successively after forming the first hole transporting layer, a second hole transporting material (aromatic amine derivative (compound X2) shown below) was vapor-deposited to form a second hole transporting layer with a thickness of 10 nm.

On the second hole transporting layer, the compound H1 (host material) obtained in Synthesis Example 1 and Ir(bzq)$_3$ (phosphorescent material) shown below were co-deposited to form a phosphorescent light emitting layer with a thickness of 25 nm. The concentration of Ir(bzq)$_3$ in the light emitting layer was 10.0% by mass. The co-deposited film works as a light emitting layer.

Successively after forming the light emitting layer, the compound ET shown below was vapor-deposited into a film with a thickness of 35 nm. The compound ET film works as an electron transporting layer.

Then, LiF was vapor-deposited into a film with a thickness of 1 nm at a film-forming speed of 0.1 Å/min to form an electron injecting electrode (cathode). On the LiF film, metallic Al was vapor-deposited to form a metallic cathode with a thickness of 80 nm, thereby obtaining an organic EL device.

The compounds used in the examples and comparative examples are shown below.

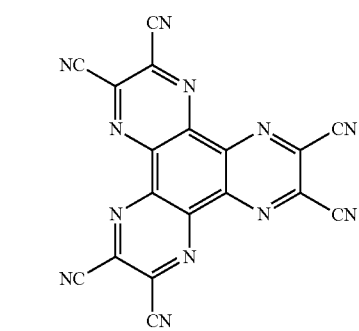

Compound C-1

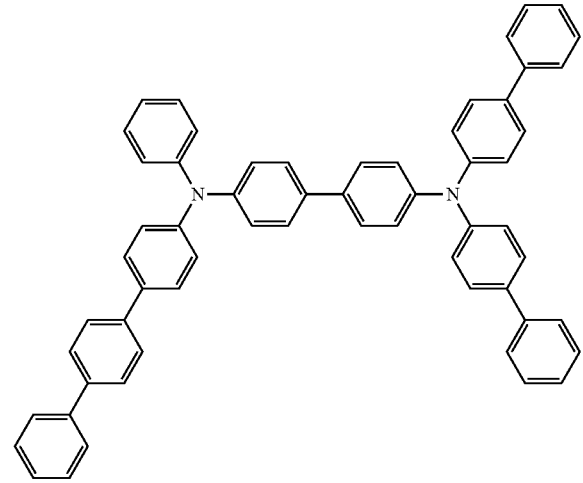

Compound X1

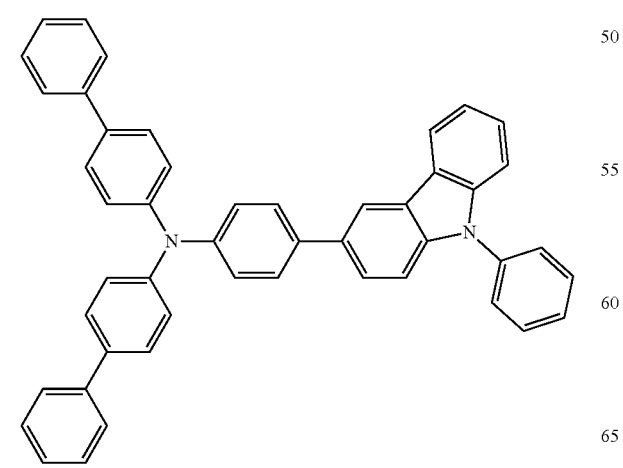

Compound X2

-continued

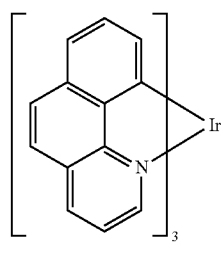

Ir(bzq)$_3$

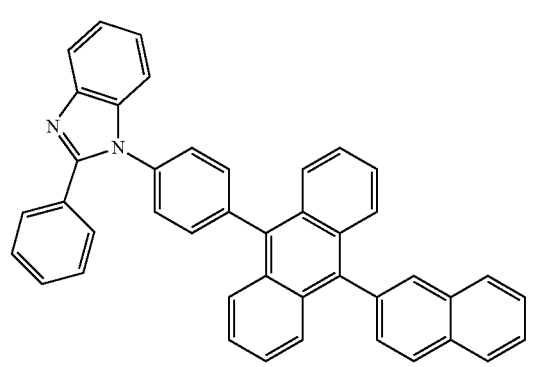

Compound ET

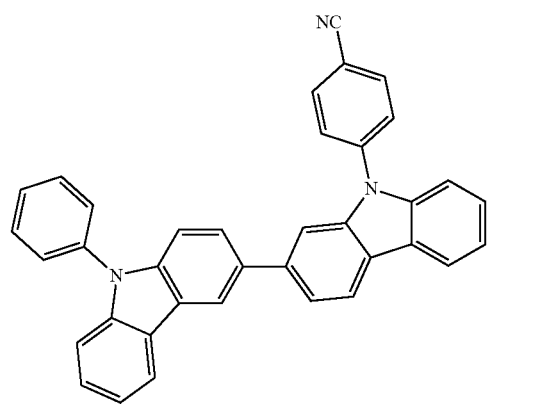

Compound H1

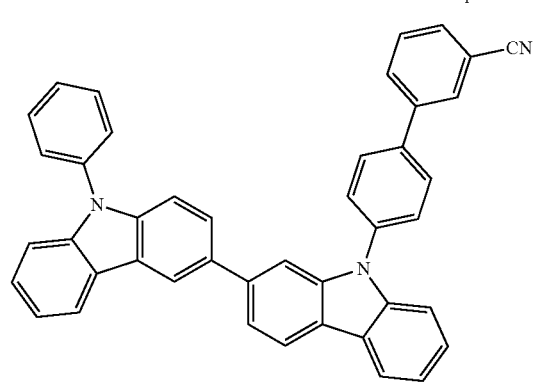

Compound H2

-continued
Compound H3
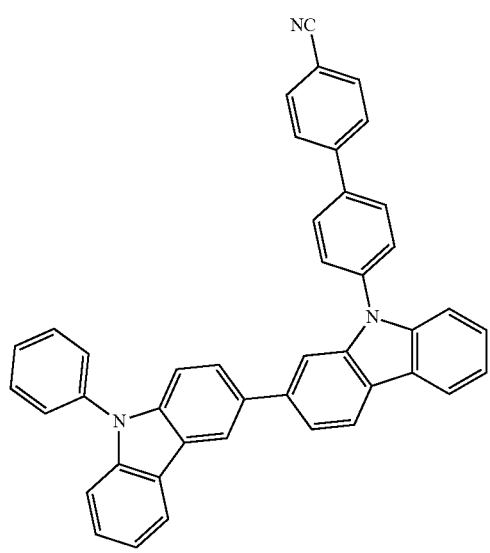
Compound H4
Compound H5
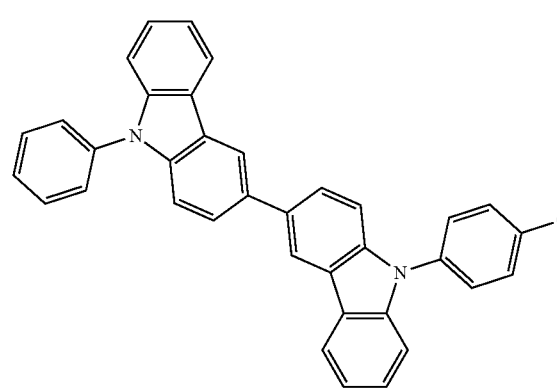
-continued
Compound H6
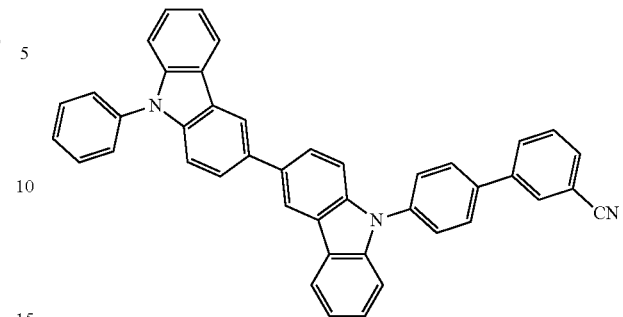
Compound F1
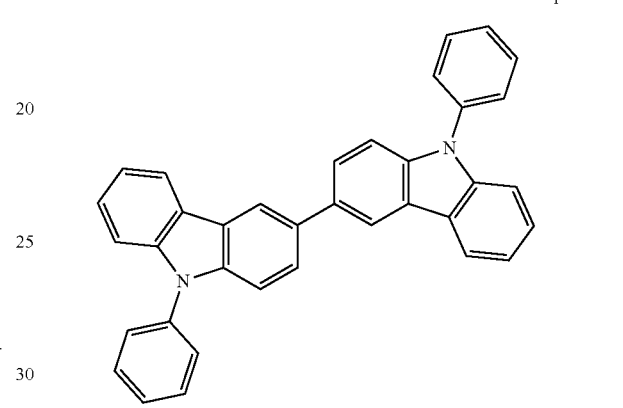
Compound F2
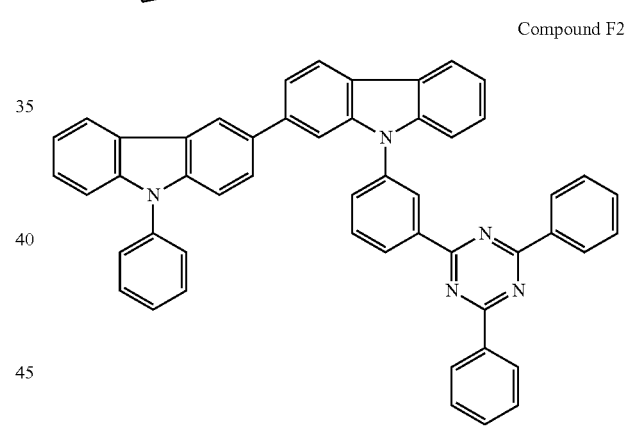
Compound F3
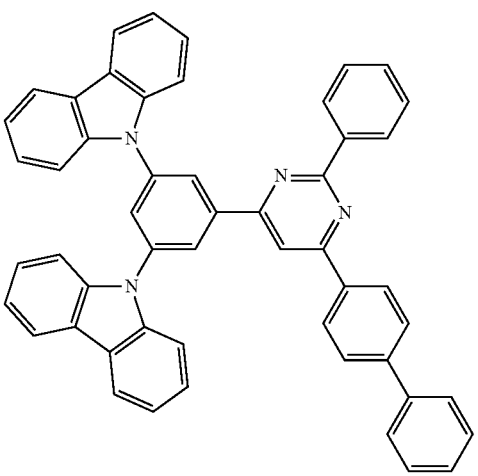

-continued

Compound BH1

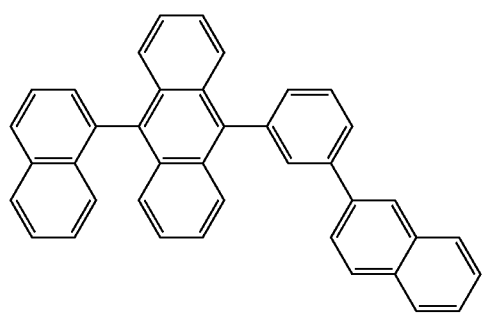

Compound BD1

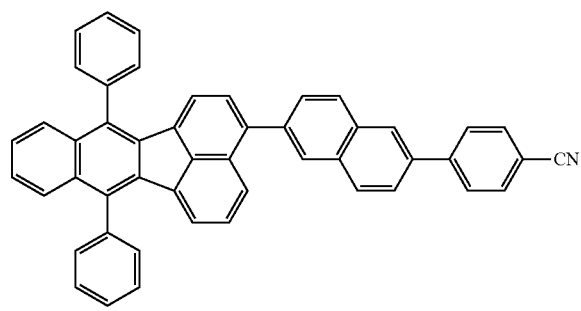

Evaluation of Emission Performance of Organic EL Device

The obtained organic EL device was measured for the emission efficiency at room temperature by driving the device at constant DC current (current density: 1 mA/cm$^2$). The results are shown in Table 1.

Examples 2-6 and Comparative Example 1

In the same manner as in Example 1 except for forming the light emitting layer by using each compound shown in Table 1 in place of the host compound H1, each organic EL device was produced. The results of measuring the emission efficiency are shown in Table 1.

TABLE 1

| | Host material of light emitting layer | Emission efficiency (cd/A) |
| --- | --- | --- |
| Example 1 | compound H1 | 59 |
| Example 2 | compound H2 | 59 |
| Example 3 | compound H3 | 61 |
| Example 4 | compound H4 | 62 |
| Example 5 | compound H5 | 58 |
| Example 6 | compound H6 | 45 |
| Comparative Example 1 | compound F1 | 10 |

As seen from Table 1, the organic EL devices of Examples 1 to 6, wherein each of the compounds H1 to H5 each having a cyano-substituted group at the terminal end of the central skeleton comprising the carbazole derivative was used as the host material of the light emitting layer, showed high emission efficiency as compared with the organic EL device of Comparative Example 1 which employed the compound F1 having a similar central skeleton but having no cyano-substituted group at its terminal end.

Example 7-10 and Comparative Example 2

Each organic EL device was produced in the same manner as in Example 1 except for forming the light emitting layer by using the host material 1 and the host material 2 listed in Table 2 as the host material of the light emitting layer in place of the compound H1. Each concentration in the light emitting layer was 10.0% by mass for Ir(bzq)$_3$, 45.0% by mass for the host material 1, and 45.0% by mass for the host material 2.

Each of the obtained organic EL device was measured for the emission efficiency at room temperature by driving the device at constant DC current (current density: 1 mA/cm$^2$) and measured for 80% lifetime at an initial luminance of 10,000 cd/m$^2$ (time taken until the luminance was reduced to 80% of the initial luminance when driving the device at constant current). The results are shown in Table 2.

TABLE 2

| | Light emitting layer | | Emission efficiency (cd/A) | 80% Lifetime (h) |
| --- | --- | --- | --- | --- |
| | Host material 1 | Host material 2 | | |
| Example 7 | compound H1 | compound F2 | 68 | 1040 |
| Example 8 | compound H1 | compound F3 | 68 | 800 |
| Example 9 | compound H3 | compound F2 | 66 | 800 |
| Example 10 | compound H4 | compound F2 | 70 | 1120 |
| Example 11 | compound H5 | compound F2 | 60 | 1040 |
| Comparative Example 2 | compound F1 | compound F3 | 50 | 480 |

As seen from Table 2, the organic EL devices of Examples 7 to 11, wherein the combination of the compounds H1 and H3 to H5 each having a cyano-substituted group at the terminal end of the central skeleton comprising the carbazole derivative with the compound F2 or F3 was used as the host material (co-host) of the light emitting layer, showed good emission efficiency. In addition, the organic EL devices of Examples 7 to 11 showed longer lifetime as compared with the organic EL device of Comparative Example 2 which employed the compound F1 and the compound F3 each having a similar central skeleton but having no cyano-substituted group at its terminal end.

Example 12

An organic EL device having the following layered structure was produced:
ITO (130 nm)/C-1 (5 nm)/X1 (80 nm)/X2 (15 nm)/BH1: BD1 (25 nm, 5% by mass)/H3 (5 nm)/ET (20 nm)/LiF (1 nm)/Al (80 nm),
wherein each numeral in the parentheses represents the thickness and represent the content (% by mass) of the dopant materials for the light emitting layer.

The organic EL device of Example 12 was produced in the following manner.

A glass substrate of 25 mm×75 mm×0.7 mm thickness having an ITO transparent electrode (anode) (product of Geomatec Company) was cleaned by ultrasonic cleaning in isopropyl alcohol for 5 min and then UV ozone cleaning for 30 min.

The cleaned glass substrate was mounted to a substrate holder of a vacuum vapor deposition apparatus. The compound C-1 was vapor-deposited so as to cover the transparent electrode to form a compound C-1 film with a thickness of 5 nm, which works as a hole injecting layer.

Successively after forming the compound C-1 film, the compound X1 was vapor-deposited to form a compound X1 film with a thickness of 80 nm on the compound C-1 film. The compound X1 film works as a first hole transporting layer.

Successively after forming the compound X1 film, the compound X2 was vapor-deposited to form a compound X2 film with a thickness of 15 nm on the compound X1 film. The compound X2 film works as a second hole transporting layer.

On the compound X2 film, the compound BH1 (host material) and the compound BD1 (dopant material) were co-deposited in a ratio of 20:1 by mass to form a light emitting layer with a thickness of 25 nm.

On the light emitting layer, the compound H3 was vapor-deposited to form a blocking layer with a thickness of 5 nm.

On the blocking layer, the compound ET (electron transporting material) was vapor-deposited to form an electron injecting layer with a thickness of 20 nm.

On the electron injecting layer, LiF was vapor-deposited to form a LiF film with a thickness of 1 nm.

On the LiF film, metallic aluminum (Al) was vapor-deposited to form a metallic cathode with a thickness of 80 nm.

Thus, the organic EL device of Example 12 was produced.

The obtained organic EL device was measured for the spectral radiance of EL emission at room temperature by driving the device at constant DC current (current density: 1 mA/cm$^2$) using a spectroradiometer (CS-1000 manufactured by Konica Minolta). The chromaticity (CIEx, CIEy), the emission efficiency (external quantum efficiency), and the main peak wavelength were determined from the obtained spectral radiance. The results are shown in Table 3.

TABLE 3

| | CIEx | CIEy | External quantum yield (%) | Main peak wavelength (nm) |
|---|---|---|---|---|
| Example 12 | 0.141 | 0.130 | 8.60 | 453 |

As seen from Table 3, a high emission efficiency expressed by the external quantum yield as high as 8.60% was obtained by using the material for organic EL device of the invention (compound H3) as the material for the blocking layer of fluorescent device.

Examples 13 to 20

Each organic EL device was produced in the same manner as in Example 1 except for forming the light emitting layer by using each compound listed in Table 4 in place of the host compound H1. The results of measuring the emission efficiency are shown in Table 4.

TABLE 4

| | Host material of light emitting layer | Emission efficiency (cd/A) |
|---|---|---|
| Example 13 | compound H7 | 68 |
| Example 14 | compound H10 | 67 |
| Example 15 | compound H12 | 56 |
| Example 16 | compound H13 | 55 |
| Example 17 | compound H14 | 55 |
| Example 18 | compound H15 | 55 |
| Example 19 | compound H16 | 56 |
| Example 20 | compound H18 | 45 |

As seen from Table 4, the organic EL devices of Examples 13 to 20, wherein each of the compounds H7, H10, H12 to H16, and H18 each having a cyano-substituted group at the terminal end of the central skeleton comprising the carbazole derivative was used as the host material of the light emitting layer, showed high emission efficiency as compared with the organic EL device of Comparative Example 1 which employed the compound F1 having a similar central skeleton but having no cyano-substituted group at its terminal end.

Example 21

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate was mounted to a substrate holder of a vacuum vapor deposition apparatus. The compound C-2 shown below was vapor-deposited so as to cover the transparent electrode to form a compound C-2 film with a thickness of 20 nm. On the compound C-2 film, an aromatic amine derivative (compound X1) used above was vapor-deposited to form a hole transporting layer with a thickness of 60 nm.

On the hole transporting layer, the compound F4 (host material) shown below and the compound BD2 (phosphorescent material) shown below were co-deposited to form a phosphorescent light emitting layer with a thickness of 50 nm. The concentration in the phosphorescent light emitting layer was 80% by mass for the compound F4 and 20% by mass for the compound BD2. The co-deposited film works as a light emitting layer.

Successively after forming the light emitting layer, the compound H13 obtained in Synthesis Example 13 was vapor-deposited into a film with a thickness of 10 nm. The compound H13 film works as a first electron transporting layer. Then, the compound ET was vapor-deposited into a film with a thickness of 10 nm. The compound ET film works as a second electron transporting layer.

Then, LiF was vapor-deposited into a film with a thickness of 1 nm at a film-forming speed of 0.1 Å/min to form an electron injecting electrode (cathode). On the LiF film, metallic Al was vapor-deposited to form a metallic cathode with a thickness of 80 nm, thereby obtaining an organic EL device.

Example 22 and Comparative Example 3

Each organic EL device was produced in the same manner as in Example 21 except for forming the first electron transporting layer by using each compound listed in Table 5 in place of the compound H13.

The compounds used in Example 21, Example 22, and Comparative Example 3 are shown below.

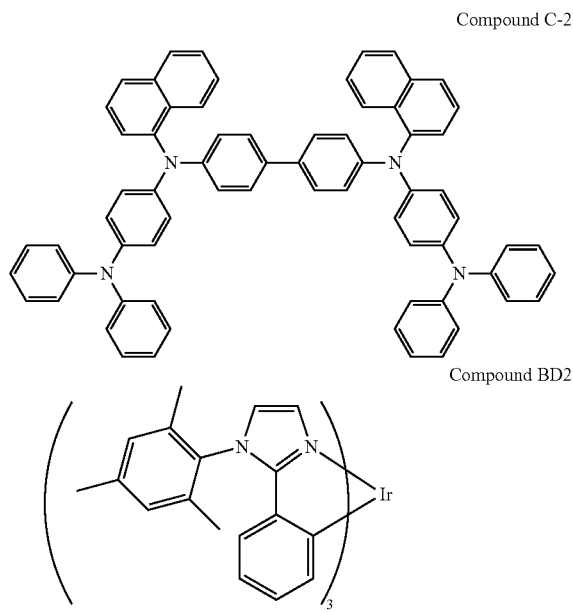

Compound C-2

Compound BD2

-continued

Compound F4

Each of the obtained organic EL devices was measured for the voltage and the emission efficiency (external quantum yield) at room temperature by driving the device at constant DC current (current density: 1 mA/cm²). The results are shown in Table 5.

TABLE 5

| | Material of first electron transporting layer | Voltage (V) | External quantum yield (%) |
|---|---|---|---|
| Example 21 | compound H13 | 4.0 | 18.4 |
| Example 22 | compound H19 | 3.7 | 19.8 |
| Comparative example 3 | compound F4 | 5.1 | 17.5 |

As seen from Table 5, the organic EL devices of Examples 21 and 22, wherein each of the compounds H13 and H19 each having a cyano-substituted group at the terminal end of the central skeleton comprising the carbazole derivative was used in the electron transporting layer adjacent to the light emitting layer, showed an improved emission efficiency and a low driving voltage, as compared with the organic EL device of Comparative Example 3 which employed the compound F4 having a similar central skeleton but having no cyano-substituted group at its terminal end.

INDUSTRIAL APPLICABILITY

As described above, the material for organic EL device of the invention is useful as a material for realizing an organic EL device with good emission efficiency.

REFERENCE NUMERALS

1: Organic electroluminescence device
2: Substrate
3: Anode
4: Cathode
5: Phosphorescent light emitting layer
6: Hole injecting/transporting layer
7: Electron injecting/transporting layer
10: Organic thin film layer

What is claimed is:

1. A material for organic electroluminescence device represented by formula (I):

(I)

wherein:
each of $A^1$ and $A^2$ independently represents a substituted or unsubstituted aromatic hydrocarbon group having 6 to 30 ring carbon atoms or a substituted or unsubstituted heterocyclic group having 5 to 30 ring atoms, wherein the heterocyclic group is selected from the group consisting of a dibenzofuran ring residue and a dibenzothiophene ring residue;
$A^3$ represents a substituted or unsubstituted monocyclic hydrocarbon group having 6 or less ring carbon atoms or a substituted or unsubstituted monocyclic heterocyclic group having 6 or less ring atoms;
each of $A^1$, $A^2$, and $A^3$ is optionally substituted with at least one group selected from the group consisting of a cyano group, a halogen atom, an alkyl group having 1 to 20 carbon atoms, a cycloalkyl group having 3 to 20 carbon atoms, an alkoxyl group having 1 to 20 carbon atoms, a haloalkyl group having 1 to 20 carbon atoms, a haloalkoxyl group having 1 to 20 carbon atoms, an alkylsilyl group having 1 to 10 carbon atoms, an aryloxy group having 6 to 30 ring carbon atoms, an arylsilyl group having 6 to 30 carbon atoms, an aralkyl group having 6 to 30 carbon atoms, a heteroaryl group having 5 to 30 ring atoms, a phenyl group, a naphthyl group, a biphenyl group, a terphenyl group, a phenanthryl group, a triphenylenyl group, a fluorenyl group, a spirobifluorenyl group, and a fluoranthenyl group, the at least one optional group being optionally further substituted with at least one of the optional groups;
m represents an integer of 0 to 3;
each of $X^1$ to $X^8$ and $Y^1$ to $Y^8$ independently represents N or $CR^a$;
each $R^a$ independently represents a hydrogen atom, a substituted or unsubstituted aromatic hydrocarbon group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted silyl group, or a halogen atom, provided that one of $X^5$ to $X^8$ and one of $Y^1$ to $Y^4$ are bonded to each other via $A^3$ or directly; and the formula (I) satisfies at least one of the following requirements (i) and (ii):
(i) at least one of $A^1$ and $A^2$ represents a cyano-substituted aromatic hydrocarbon group having 6 to 30 ring carbon atoms or a cyano-substituted heterocyclic group having 5 to 30 ring atoms, wherein the heterocyclic group is selected from the group consisting of a dibenzofuran ring residue and a dibenzothiophene ring residue; and
(ii) at least one of $X^1$ to $X^4$ and $Y^5$ to $Y^8$ represents $CR^a$, and at least one of $R^a$ in $X^1$ to $X^4$ and $Y^5$ to $Y^8$ represents a cyano-substituted aromatic hydrocarbon group having 6 to 30 ring carbon atoms or a cyano-substituted heterocyclic group having 5 to 30 ring atoms, provided that when two or more $R^a$ groups exist, the $R^a$ groups may be the same or different.

2. The material for organic electroluminescence device according to claim 1, which satisfies the requirement (i) but does not satisfy the requirement (ii).

3. The material for organic electroluminescence device according to claim 1, which satisfies the requirement (ii) but does not satisfy the requirement (i).

4. The material for organic electroluminescence device according to claim 1, which satisfies both the requirements (i) and (ii).

5. The material for organic electroluminescence device according to claim 1, wherein at least one of $A^1$ and $A^2$ represents a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group.

6. The material for organic electroluminescence device according to claim 1, wherein $A^1$ is substituted by a cyano group, and $A^2$ is not substituted by a cyano group.

7. The material for organic electroluminescence device according to claim 1, wherein at least one of $X^1$ to $X^4$ and $Y^5$ to $Y^8$ represents $CR^a$, and at least one of $R^a$ in $X^1$ to $X^4$ and $Y^5$ to $Y^8$ represents a cyano-substituted phenyl group, a cyano-substituted naphthyl group, a cyano-substituted phenanthryl group, a cyano-substituted dibenzofuranyl group, a cyano-substituted dibenzothiophenyl group, a cyano-substituted biphenyl group, a cyano-substituted terphenyl group, a cyano-substituted 9,9-diphenylfluorenyl group, a cyano-substituted 9,9'-spirobi[9H-fluorene]-2-yl group, a cyano-substituted 9,9-dimethylfluorenyl group, or a cyano-substituted triphenylenyl group.

8. The material for organic electroluminescence device according to claim 1, wherein $X^6$ and $Y^3$ are bonded to each other via $A^3$ or directly.

9. The material for organic electroluminescence device according to claim 1, wherein $X^6$ and $Y^2$ are bonded to each other via $A^3$ or directly.

10. The material for organic electroluminescence device according to claim 1, wherein $X^7$ and $Y^3$ are bonded to each other via $A^3$ or directly.

11. The material for organic electroluminescence device according to claim 1, wherein m represents 0.

12. The material for organic electroluminescence device according to claim 1, wherein m represents 1.

13. An organic electroluminescence device comprising an organic thin film layer comprising one or more layers between a cathode and an anode, wherein the organic thin film layer comprises a light emitting layer, and at least one layer of the organic thin film layer comprises the material for organic electroluminescence device according to claim 1.

14. The organic electroluminescence device according to claim 13, wherein the light emitting layer comprises the material for organic electroluminescence device.

15. The organic electroluminescence device according to claim 13, wherein the light emitting layer comprises a phosphorescent material selected from ortho metallated complexes of a metal selected from iridium (Ir), osmium (Os), and platinum (Pt).

16. The organic electroluminescence device according to claim 1, which further comprises a layer adjacent to the light emitting layer between the cathode and the light emitting layer, and the layer adjacent to the light emitting layer comprises the material for organic electroluminescence device.

17. The organic electroluminescence device according to claim 1, which further comprises a blocking layer adjacent to the light emitting layer between the cathode and the light emitting layer, and the blocking layer comprises the material for organic electroluminescence device.

18. The material for organic electroluminescence device according to claim 1, wherein the monocyclic hydrocarbon group having 6 or less ring carbon atoms is selected from the group consisting of a phenylene group, a cyclopentenylene group, a cyclopentadienylene group, a cyclohexylene group, and a cyclopentylene group.

19. The material for organic electroluminescence device according to claim 1, wherein the monocyclic heterocyclic group having 6 or less ring atoms is selected from the group consisting of a pyrrolylene group, a pyrazinylene group, a pyridinylene group, a furylene group, and a thiophenylene group.

20. The material for organic electroluminescence device according to claim 1, wherein at least one of $A^1$ and $A^2$ is a dibenzofuran-2-yl group or a dibenzofuran-4-yl group.

21. The material for organic electroluminescence device according to claim 1, wherein at least one of $A^1$ and $A^2$ is a dibenzothiophene-2-yl group or a dibenzothiophene-4-yl group.

22. The material for organic electroluminescence device according to claim 1, wherein at least one of $A^1$ and $A^2$ is selected from the group consisting of a dibenzofuran ring residue and a dibenzothiophene ring residue.

23. The material for organic electroluminescence device according to claim 1, wherein each of $A^1$ and $A^2$ of formula (I) independently represents a dibenzofuran ring residue, a dibenzothiophene ring residue, a phenyl group, a naphthyl group, a phenanthryl group, a biphenyl group, a terphenyl group, a quaterphenyl group, a fluoranthenyl group, a triphenylenyl group, a phenanthrenyl group, a fluorenyl group, a spirofluorenyl group, a 9,9-diphenylfluorenyl group, a 9,9'-spirobi[9H-fluorene]-2-yl group, a 9,9-dimethylfluorenyl group, a benzo[c]phenanthrenyl group, a benzo[a]triphenylenyl group, a naphtha[1,2-c]phenanthryl group, a naphtho[1,2-a]triphenylenyl group, a dibenzo[a,c]triphenylenyl group, or a benzo[b]fluoranthenyl group.

24. The material for organic electroluminescence device according to claim 1, wherein each $R^a$ independently represents:
   an aromatic hydrocarbon group selected from the group consisting of a phenyl group, a naphthyl group, a phenanthryl group, a biphenyl group, a terphenyl group, a quaterphenyl group, a fluoranthenyl group, a triphenylenyl group, a phenanthrenyl group, a fluorenyl group, a spirofluorenyl group, a 9,9-diphenylfluorenyl group, a 9,9'-spirobi[9H-fluorene]-2-yl group, a 9,9-dimethylfluorenyl group, a benzo[c]phenanthrenyl group, a benzo[a]triphenylenyl group, a naphtha[1,2-c]phenanthryl group, a naphtho[1,2-a]triphenylenyl group, a dibenzo[a,c]triphenylenyl group, and a benzo[b]fluoranthenyl group;
   a heterocyclic group selected from the group consisting of a pyrrole ring residue, an isoindole ring residue, a benzofuran ring residue, an isobenzofuran ring residue, a dibenzothiophene ring residue, an isoquinoline ring residue, a quinoxaline ring residue, a phenanthridine ring residue, a phenanthroline ring residue, a pyridine ring residue, a pyrazine ring residue, a pyrimidine ring residue, a pyridazine ring residue, a triazine ring residue, an indole ring residue, a quinoline ring residue, an acridine ring residue, a pyrrolidine ring residue, a dioxane ring residue, a piperidine ring residue, a morpholine ring residue, a piperazine ring residue, a furan ring residue, a thiophene ring residue, an oxazole ring residue, a oxadiazole ring residue, a benzoxazole ring residue, a thiazole ring residue, a thiadiazole ring residue, a benzothiazole ring residue, a triazole ring residue, a imidazole ring residue, a benzimidazole ring residue, a pyran ring residue, a dibenzofuran ring residue, and a benzo[c]dibenzofuran ring residue;
   an alkyl group selected from the group consisting of a methyl group, an ethyl group, an n-propyl group, an isopropyl group, an n-butyl group, an s-butyl group, an isobutyl group, a t-butyl group, a cyclopentyl group, and a cyclohexyl group; or a silyl group selected from the group consisting of a trimethylsilyl group, a triethylsilyl group, a t-butyldimethylsilyl group, a vinyldimethylsilyl group, and a propyldimethylsilyl group.

25. The material for organic electroluminescence device according to claim 1, wherein $A^1$, $A^2$, and $A^3$ are not substituted with the at least one optional group.

* * * * *